US012779015B2

(12) United States Patent
Bryla et al.

(10) Patent No.: US 12,779,015 B2
(45) Date of Patent: Nov. 3, 2026

(54) COMPOSITIONS OF GROWTH FACTOR FOR THE TREATMENT OF EYE DISEASE

(71) Applicant: Claris Biotherapeutics, Inc., Jersey City, NJ (US)

(72) Inventors: Piotr Bryla, Jersey City, NJ (US); A. Clarke Atwell, Jersey City, NJ (US)

(73) Assignee: Claris Biotherapeutics, Inc., Jersey City, NJ (US)

( * ) Notice: Subject to any disclaimer, the term of this patent is extended or adjusted under 35 U.S.C. 154(b) by 842 days.

(21) Appl. No.: 17/743,488

(22) Filed: May 13, 2022

(65) Prior Publication Data

US 2023/0022990 A1 Jan. 26, 2023

Related U.S. Application Data

(60) Provisional application No. 63/188,816, filed on May 14, 2021.

(51) Int. Cl.
*A61K 38/18* (2006.01)
*A61P 27/02* (2006.01)

(52) U.S. Cl.
CPC ...... *A61K 38/1833* (2013.01); *A61K 38/1825* (2013.01); *A61P 27/02* (2018.01)

(58) Field of Classification Search
CPC .. A61K 38/1833; A61K 38/1825; A61P 27/02
See application file for complete search history.

(56) References Cited

U.S. PATENT DOCUMENTS

| | | | |
|---|---|---|---|
| 3,773,919 | A | 11/1973 | Boswell et al. |
| 4,485,045 | A | 11/1984 | Regen |
| 4,544,545 | A | 10/1985 | Ryan et al. |
| 5,103,047 | A | 4/1992 | Viso et al. |
| 5,510,329 | A | 4/1996 | Belkin et al. |
| 5,589,451 | A | 12/1996 | Wilson |
| 5,703,047 | A | 12/1997 | Wilson |
| 5,776,464 | A | 7/1998 | Nakamura |
| 5,821,223 | A | 10/1998 | Rubin et al. |
| 6,423,691 | B1 | 7/2002 | Azuma et al. |
| 6,699,837 | B2 | 3/2004 | Nakamura |
| 6,869,609 | B1 | 3/2005 | Yamazaki et al. |
| 7,173,008 | B2 | 2/2007 | Tanaka et al. |
| 8,039,445 | B2 | 10/2011 | Behar-Cohen et al. |
| 8,383,588 | B2 | 2/2013 | Amano et al. |
| 8,461,112 | B2 | 6/2013 | Adachi et al. |
| 9,061,050 | B2 | 6/2015 | Gobin et al. |
| 9,556,248 | B2 | 1/2017 | Cochran et al. |
| 9,610,245 | B2 | 4/2017 | Steele |
| 9,884,078 | B2 | 2/2018 | Harrell |
| 10,098,927 | B2 | 10/2018 | Bartorelli et al. |
| 10,117,906 | B2 | 11/2018 | Dana et al. |
| 10,213,485 | B2 | 2/2019 | Fukuta et al. |
| 10,435,444 | B2 | 10/2019 | Usui et al. |
| 10,449,234 | B2 | 10/2019 | Chauhan et al. |
| 11,759,499 | B2 | 9/2023 | Chauhan et al. |
| 2006/0229245 | A1 | 10/2006 | Tanaka et al. |
| 2007/0167935 | A1 | 7/2007 | Serdarevic |
| 2008/0108045 | A1 | 5/2008 | Ghinelli |
| 2009/0209463 | A1 * | 8/2009 | Nakamura .............. A61P 35/00 435/68.1 |
| 2010/0322998 | A1 | 12/2010 | Nakamura et al. |
| 2011/0269944 | A1 | 11/2011 | Nakamura et al. |
| 2012/0190621 | A1 | 7/2012 | Tabata et al. |
| 2014/0378391 | A1 | 12/2014 | Horn |
| 2016/0129154 | A1 | 5/2016 | Hopkinson et al. |
| 2016/0250291 | A1 | 9/2016 | Jeong |
| 2017/0189487 | A1 | 7/2017 | Ohori et al. |
| 2017/0305985 | A1 | 10/2017 | Cochran et al. |
| 2017/0333527 | A1 | 11/2017 | Fukuta et al. |
| 2018/0311283 | A1 | 11/2018 | Daniel et al. |
| 2019/0022220 | A1 | 1/2019 | Goldberg et al. |
| 2020/0038484 | A1 | 2/2020 | Myung et al. |
| 2020/0190158 | A1 | 6/2020 | Eveleth et al. |
| 2021/0299219 | A1 | 9/2021 | Chauhan et al. |

FOREIGN PATENT DOCUMENTS

| | | |
|---|---|---|
| DE | 3218121 | 11/1983 |
| EP | 0036676 | 9/1981 |
| EP | 0052322 | 5/1982 |
| EP | 0058481 | 8/1982 |
| EP | 0088046 | 9/1983 |
| EP | 0102324 | 3/1984 |
| EP | 0133988 | 3/1985 |
| EP | 0142641 | 5/1985 |
| EP | 0143949 | 6/1985 |
| EP | 1180368 | 2/2002 |
| EP | 2025342 | 2/2009 |
| JP | H 09-25241 | 1/1997 |

(Continued)

OTHER PUBLICATIONS

A classic sugar, trehalose offers new solutions, from https://www.nature.com/articles/d42473-020-00416-1, accessed 2025, pp. 1-5.*
Citric acid and sodium citrate, from https://www.cspinet.org/article/citric-acid-sodium-citrate, accessed 2025, pp. 1-2.*
What are the five natural surfactants?, from https://www.aatbio.com/resources/faq-frequently-asked-questions/What-are-the-five-natural-surfactants, 2021, pp. 1-2.*
Omoto et al., "Hepatocyte Growth Factor Suppresses Inflammation and Promotes Epithelium Repair in Corneal Injury," Molecular Therapy, Aug. 2017, 25(8):1881-1888.
PCT International Preliminary Report on Patentability in International Appln. No. PCT/US2022/072302, mailed on Nov. 23, 2023, 23 pages.
Abdelkader et al., "New therapeutic approaches in the treatment of diabetic keratopathy: a review" Clin Exp Ophthalmol., Apr. 2011, 39(3):259-270.

(Continued)

*Primary Examiner* — Li N Komatsu
(74) *Attorney, Agent, or Firm* — Fish & Richardson P.C.

(57) ABSTRACT

The present disclosure relates to pharmaceutical compositions comprising a growth factor and methods of treating or preventing of eye diseases using the growth factor and compositions thereof.

13 Claims, 5 Drawing Sheets

Specification includes a Sequence Listing.

(56) References Cited

FOREIGN PATENT DOCUMENTS

| | | |
|---|---|---|
| JP | 2000-344680 | 12/2000 |
| WO | WO 90/10651 | 9/1990 |
| WO | WO 00/72873 | 12/2000 |
| WO | WO 2005/023287 | 3/2005 |
| WO | WO 2008/102849 | 8/2008 |
| WO | WO 2016/039163 | 3/2016 |
| WO | WO 2017/044743 | 3/2017 |
| WO | WO 2018/201002 | 11/2018 |
| WO | WO 2018/204847 | 11/2018 |
| WO | WO 2021/263134 | 12/2021 |

OTHER PUBLICATIONS

Anitua et al., "Plasma rich in growth factors (PRGF-Endoret) stimulates corneal wound healing and reduces haze formation after PRK surgery," Exp Eye Res., Oct. 2013, 115:153-61.

Anitua et al., "Differential profile of protein expression on human keratocytes treated with autologous serum and plasma rich in growth factors (PRGF)," PLoS One, Oct. 12, 2018, 13(10):e0205073 (14 pages).

Bottaro et al., "Identification of the Hepatocyte Growth Factor Receptor as the c-met Proto-Oncogene Product," Science, Feb. 15, 1991, 251(4995):802-804.

Calvo et al., "Comparative in vitro evaluation of several colloidal systems, nanoparticles, nanocapsules, and nanoemulsions, as ocular drug carriers," Journal of Pharmaceutical Sciences, May 1996, 85(5):530-536.

Chan et al., "Identification of a Competitive HGF Antagonist Encoded by an Alternative Transcript," Science, Nov. 29, 1991, 254(5036):1382-1385.

Cioce et al., "Hepatocyte Growth Factor (HGF)/NK1 Is a Naturally Occurring HGF/Scatter Factor Variant with Partial Agonist/Antagonist Activity," J Biol. Chem., May 31, 1996, 271(22): 13110-13115.

Creighton et al., "Proteins: Structures and Molecular Properties," Biochemistry and Molecular Biology, Apr. 1985, 13(2):88.

De Pascale et al., "Human Serum Eye Drops in Eye Alterations: An Insight and a Critical Analysis," J Ophthalmol., 2015, 396410 (15 pages).

Deshmukh et al., "Management of corneal perforations: An update," Indian J Ophthalmol., 2020, 68(1):7-14.

Eppstein et al., "Biological activity of liposome-encapsulated murine interferon y is mediated by a cell membrane receptor," Proc. Natl. Acad Sci. US.A., Jun. 1985, 82:3688-3692.

Fantes et al., "Wound healing after excimer laser keratomileusis photorefractive keratectomy) in monkeys," Archives of Ophthalmology, 1990, 108(5):665-675.

Gambato et al., "Mitomycin C modulation of corneal wound healing after photorefractive keratectomy in highly myopic eyes," Ophthalmology, Feb. 2005, 112(2):208-18.

Gurny, "Ocular therapy with nanoparticles," Polymeric Nanoparticles and Microspheres, 1986, pp. 127-136.

Gurny, "Preliminary study of prolonged acting drug delivery system for the treatment of glaucoma," Pharm Acta Helv., 1981, pp. 130-132.

Hwang et al., "Hepatic uptake and degradation of unilamellar sphingomyelin/cholesterol liposomes: a kinetic study," Proc. Natl. Acad Sci. US.A., Jul. 1980, 77(7):4030-4034.

Jiang et al., "HGF suppresses the production of collagen type III and alpha-SMA induced by TGF-betal in healing fibroblasts," Eur J Appl Physiol., Jul. 2008, 103(5):489-93.

Jones II, et al., "Engineering hepatocyte growth factor fragments with high stability and activity as Met receptor agonists and antagonists," Proc. Natl. Acad Sci., Jul. 25, 2011, 108:13035-13040.

Kakazu et al., "HGF Protects Corneal Epithelial Cells from Apoptosis by the PI-3K/Akt-1/Bad—but not the ERK1/2-mediated Signaling Pathway," Investigative Opthalmology and Visual Science, Oct. 1, 2004, 45(10):3485-3492.

Kojima et al., "Autologous serum eye drops for the treatment of dry eye diseases," Cornea, Sep. 2008, 27(Suppl. 1):S25-S30.

Kompella et al., "Recent advances in ophthalmic drug delivery," Therapeutic Delivery, Sep. 2010, 1(3):435-456.

Kowtharapu et al., "Corneal Cells: Fine-tuning Nerve Regeneration," Current Eye Research, 2020, 45(3):291-302.

Kreuter, "Nanoparticles," Colloidal Drug Delivery Systems, 1995, Chapter 5, pp. 219-342.

Lambiase et al., "Capsaicin-Induced Corneal Sensory Denervation and Healing Impairment Are Reversed by NGF Treatment," IOVS, Dec. 2012, 53(13): 8280-8287.

Lambiase et al., "Nerve Growth Factor Promotes Corneal Healing: Structural, Biochemical, and Molecular Analyses of Rat and Human Corneas," IOVS, Apr. 2000, 41(5):1063-1069.

Langer et al., "Biocompatibility of polymeric delivery systems for macromolecules," J Biomed Mater. Res., Mar. 1981, 15(2):267-277.

Li et al., "Hepatocyte Growth Factor and Hepatocyte Growth Factor Receptor in the Lacrimal Gland, Tears, and Cornea," Invest. Ophthalmol. Vis. Sci., Apr. 1996, 37(5):727-739.

Liu et al., "An engineered dimeric fragment of hepatocyte growth factor is a potent c-MET agonist," FEBS Letters, Dec. 20, 2014, 588(24):4831-4837.

Lokker et al., "Structure-function analysis of hepatocyte growth factor: identification of variants that lack mitogenic activity yet retain high affinity receptor binding," The EMBO Journal, 1992, 11(7):2503-2510.

López-Plandolit et al., "Plasma rich in growth factors as a therapeutic agent for persistent corneal epithelial defects," Cornea, 2010, 29(8):843-848.

Masumoto et al., "Sequestration of a hepatocyte growth factor in extracellular matrix in normal adult rat liver," Biochem. Biophys. Res. Commun., Jan. 15, 1991, 174(1):90-95.

Matsumoto et al., "HGF-Met Pathway in Regeneration and Drug Discovery," Biomedicines, Oct. 2014, 2(4):275-300.

Mccann, "Advances and Challenges in Topical Ocular Medications," Advanced. Ocular Care, 2011, pp. 23-25.

Mishra et al., "Recent applications of liposomes in ophthalmic drug delivery," Journal of Drug Delivery, 2011, 2011:863734, 14 pages.

Mitchell et al., "Engineering a potent inhibitor of matriptase from the natural hepatocyte growth factor activator inhibitor type-1 (HAI-1) protein," J Biol Chem., Apr. 6, 2018, 293(14):4969-4980.

Mittal et al., "Restoration of Corneal Transparency by Mesenchymal Stem Cells," Stem Cell Reports, Oct. 2016, 7(4):583-590.

Miyagi et al., "The role of hepatocyte growth factor in corneal wound healing," Experimental Eye Research, Oct. 2017, 166:49-55 pp. 49-55.

Miyazawa et al., "An alternatively processed mRNA generated from human hepatocyte growth factor gene," Eur. J Biochem., 1991, 197:15-22.

Moiseev et al., "Penetration Enhancers in Ocular Drug Delivery," Pharmaceutics, Jul. 9, 2019, 11(7):321 (33 pages).

Montesano et al., "Differential effects of hepatocyte growth factor isoforms on epithelial and endothelial tubulogenesis," May 1, 1998, Cell Growth Differ., 9(5):355-365.

Nakamura et al., "Molecular cloning and expression of human hepatocyte growth factor," Nature, Nov. 1989, 342:440-443.

Nakamura, Toshikazu, "Structure and function of hepatocyte growth factor," Prog. Growth Factor Res., 1991, 3(1):67-85.

National Center for Biotechnology Information, "Human hepatocyte growth factor," GenBank Accession No. P14210.2, Jan. 16, 2019, 20 pages.

nei.nih.gov [online], "Facts About Dry Eye," available on or before Sep. 5, 2015, via Internet Archive: Wayback Machine URL<https://web.archive.org/web/20150905104213/https://nei.nih.gov/health/dryeye/dryeye>, URL<https://nei.nih.gov/health/dryeye/dryeye>, 6 pages.

Okada et al., "Neurotrophic keratopathy; its pathophysiology and treatment," Histology and Histopathology, Jun. 2010, 25(6):771-780.

PCT International Search Report and Written Opinion in International Appln. No. PCT/US2022/072302, mailed on Sep. 28, 2022, 31 pages.

(56) References Cited

OTHER PUBLICATIONS

PCT Invitation to Pay Additional Fees in International Appln. No. PCT/US2022/072302, mailed on Aug. 11, 2022, 15 pages.
Rubin et al., "A broad-spectrum human lung fibroblast-derived mitogen is a variant of hepatocyte growth factor.," Proc. Natl. Acad. Sci., Jan. 15, 1991, 88(2):415-419.
Sakata et al., "Heparin Binding and Oligomerization of Hepatocyte Growth Factor/Scatter Factor Isoforms," J Biol. Chem., Apr. 4, 1997, 272(14):9457-9463.
Sharma et al., "Evaluation of umbilical cord serum therapy in acute ocular chemical burns," Investigative Ophthalmology & Visual Science, Feb. 2011, 52(2):1087-1092.
Sidman et al., "Controlled release of macromolecules and pharmaceuticals from synthetic polypeptides based on glutamic acid," Biopolymers, Jan. 1983, 22(1):547-556.
Sigelman et al., "Mitotic and wound-healing activities of the corneal epithelium: effect of sensory denervation," AMA Archives of Ophthalmology, Jul. 1954, 52(1):46-57.
Sigurdardottir et al., "Exploring the chemical space of the lysine-binding pocket of the first kringle domain of hepatocyte growth factor/scatter factor (HGF/SF) yields a new class of inhibitors of HGF/SF-MET binding," Chemical Science, Nov. 2015, 6(11):6147-6157.
Simonneau et al.,"Semi-synthesis of a HGF/SF kringle one (K1) domain scaffold generates a potent in vivo MET receptor agonist," Chemical Science, Mar. 2015, 6(3):2110-2121.
Stahl et al., "Functional and biophysical characterization of recombinant human hepatocyte growth factor isoforms produced in *Escherichia coli*," Biochem. J, 1997, 326(3):763-772.
Steele et al., "A novel protein-engineered hepatocyte growth factor analog released via a shear-thinning injectable hydrogel enhances post-infarction ventricular function," Biotechnology & Bioengineering, Jun. 2, 2017, 114(10): 2379-2389.
Suarez et al., "Degradable acetalated dextran microparticles for tunable release of an engineered hepatocyte growth factor fragment," ACS Biomaterials Science & Engineering, 2016, 2(2):197-204.
Sun et al., "H-RN, a peptide derived from hepatocyte growth factor, inhibits corneal neovascularization by inducing endothelial apoptosis and arresting the cell cycle," BMC Cell Biol., Feb. 2013, 14(8):1-10.
Tatusova et al., "Blast 2 sequences—a new tool for comparing protein and nucleotide sequences," FEMS Microbio Lett., 1999, 174:247-250.
Wilson et al., "Hepatocyte Growth Factor, Keratinocyte Growth Factor, Their Receptors, Fibroblast Growth Factor Receptor-2, and the Cells of the Cornea," Invest. Ophthalmol. Vis. Sci., Jul. 1993, 34(8):2544-2561.
Wilson et al., "Lacrimal Gland HGF, KGF, and EGF mRNA Levels Increase after Corneal Epithelial Wounding," Investigative Ophthamology & Visual Science, Sep. 1999, 40(10):2185-2190.
Woo et al., "Nerve growth factor and corneal wound healing in dogs," Experimental Eye Research, 2005, 80:633-642.
Yoon et al., "Application of umbilical cord serum eyedrops for the treatment of neurotrophic keratitis," Ophthalmology, Sep. 2007, 114(9):1637-1642.
Zambito et al., "Polysaccharides as Excipients for Ocular Topical Formulations," Biomaterials Applications for Nanomedicine, Nov. 2011, pp. 253-284.
Zernii et al., "Therapeutic Proteins for Treatment of Corneal Epithelial Defects," Curr Med Chem., 2019, 26(3):517-545.
Zimmer et al., "Microspheres and nanoparticles used in ocular delivery systems," Advanced Drug Delivery Reviews, Aug. 1995, 16(1):61-73.
Extended European Search Report in European Appln. No. 25163012.5, mailed on Aug. 13, 2025, 18 pages.

* cited by examiner

| Comparison | P-value | Significance |
|---|---|---|
| PBS vs. 0.1% dHGF | 0.0054 | ** |
| PBS vs. 0.2% dHGF | 0.0015 | ** |
| PBS vs. mNGF | 0.0859 | ns |
| PBS vs. mHGF | 0.0027 | ** |
| 0.1% dHGF vs. 0.2% dHGF | 0.7588 | ns |
| mNGF vs. mHGF | 0.0228 | * |

ns = not significant

** =

* =

COMPOSITIONS OF GROWTH FACTOR FOR THE TREATMENT OF EYE DISEASE

CLAIM OF PRIORITY

This application claims the benefit of U.S. Provisional Application Ser. No. 63/188,816, filed on May 14, 2021. The entire contents of the foregoing are incorporated herein by reference.

SEQUENCE LISTING

This application contains a Sequence Listing that has been submitted electronically as an ASCII text file named "49082-0004001." The ASCII text file, created on Jul. 11, 2025, is 174,758 bytes in size. The material in the ASCII text file is hereby incorporated by reference in its entirety.

FIELD OF THE INVENTION

The present disclosure relates to pharmaceutical compositions comprising a growth factor and methods of treating or preventing of eye diseases using the growth factor and compositions thereof.

BACKGROUND OF THE INVENTION

Hepatocyte Growth Factor (HGF) has been investigated for the treatment of corneal haze of scarring. See, U.S. Pat. No. 10,449,234. Other eye injuries and diseases have been identified that could benefit from new treatments. For example, neurotrophic keratitis (also known as neurotrophic keratopathy (NK) or neuroparalytic keratitis) is a corneal disease resulting from either damage to the trigeminal nerve or its pathway to the cornea, or compromised ocular surface, which lead to consequential reduction or loss of corneal sensation. NK was first recognized as a corneal disorder in 1824 by Magendie (Okada et al., 2010, Histol Histopathol, 25:771-780) and its molecular basis subsequently established in an animal model by Sigelman and Friedenwald in 1954 (Sigelman and Friedenwald, 1954, *Arch Ophthalmol,* 53:46-57). The cornea is the transparent "window" of the eye and, together with the sclera, forms the outer shell of the eye ball. As the cornea lacks vascular supply, nutrients and oxygen are supplied to this tissue primarily via tear fluid and limbal vessels anteriorly and aqueous humor posteriorly. The corneal tissue is stratified into five layers: epithelium, Bowman's membrane, stroma, Descemet's membrane, and endothelium, with the epithelium serving as the main barrier that protects the corneal stroma below. The cornea is the most sensitive tissue in the body, innervated by an extensive nerve fiber network across the various layers and dense nerve endings. Sensory innervation of the cornea originates from the ophthalmic branch of the trigeminal nerve which secretes growth factors that are essential for the survival of the epithelium. The trigeminal nerve maintains the stability of the tear film and together, with various physiologically active substances secreted by the epithelium (e.g. cytokines, proteases and neuropeptides), further ensure the vitality of the corneal epithelium and stroma. Impairment to the trigeminal nerve or the epithelium is most commonly caused by infections (e.g. herpes simplex or zoster infections), eye surgeries (e.g. cataract surgery, corneal transplantation, refractive surgery), other systemic diseases such as diabetes, leprosy, orbital tumors and inflammations, or physical trauma including chemical and thermal burns, and the use of contact lenses.

Accordingly, there is an ongoing need for new treatments for eye diseases such as NK, as well as new pharmaceutical formulations that can be administered to the eye. The methods described herein have been developed toward this end.

SUMMARY OF THE INVENTION

The present invention provides methods of treating or preventing neurotrophic keratitis in a subject in need thereof, the method comprising administering to the subject a growth factor such as hepatocyte growth factor (HGF) or fibroblast growth factor (FGF).

The present invention further provides pharmaceutical compositions comprising HGF or FGF for the treatment of eye diseases.

Provided herein, are methods of treating or preventing neurotrophic keratitis in a subject in need thereof, the method comprising administering to the subject a therapeutically effective amount of a hepatocyte growth factor (HGF) or fibroblast growth factor (FGF), e.g., as described herein.

In some embodiments, the HGF or FGF is purified.

In some embodiments, the HGF or FGF is administered in combination with a corneal stroma permeating excipient.

In some embodiments, the HGF of FGF is formulated in a liquid pharmaceutical composition.

In some embodiments, the HGF or FGF is administered to the eye. In some embodiments, the HGF or FGF is topically administered to the eye. In some embodiments, the HGF or FGF is administered to the eye by injection. In some embodiments, the HGF or FGF is administered subconjunctivally. In some embodiments, the HGF or FGF is administered intracamerally.

In some embodiments, the liquid pharmaceutical composition comprises HGF or FGF in a concentration of about 0.01% (w/v) to about 1.0% (w/v). In some embodiments, the liquid pharmaceutical composition comprises HGF or FGF in a concentration of about 0.08% (w/v) to about 0.25% (w/v). In some embodiments, the liquid pharmaceutical composition comprises HGF or FGF in a concentration of about 0.1% (w/v). In some embodiments, the liquid pharmaceutical composition comprises HGF or FGF in a concentration of about 0.2% (w/v).

In some embodiments, the HGF or FGF is administered in combination with a further therapeutic agent. In some embodiments, the further therapeutic agent is a further growth factor.

In some embodiments, the HGF comprises a polypeptide sequence having any one of SEQ ID NOS: 1-27. In some embodiments, the HGF comprises a polypeptide sequence which has 95% sequence identity to SEQ ID NO: 1. In some embodiments, the HGF comprises of a polypeptide sequence having SEQ ID NO: 1.

Also provided herein pharmaceutical compositions comprising: about 0.01% to about 1.0% (w/v) HGF; a buffer that can maintain the pH of the composition at about 5.8 to about 6.2; about 100 to about 300 mM of a stabilizer selected from trehalose, proline, sorbitol, and a mixture thereof; optionally a tonicity modifier that can provide the osmolality of the composition of about 250 mOsm/kg $H_2O$ to about 500 mOsm/kg $H_2O$; and optionally a surfactant.

In some embodiments, the pharmaceutical composition comprises about 0.05% to about 0.5% (w/v) HGF. In some embodiments, the pharmaceutical composition comprises about 0.08% to about 0.25% (w/v) HGF. In some embodiments, the pharmaceutical composition comprises about 0.1% (w/v) HGF. In some embodiments, the pharmaceutical composition comprises about 0.2% (w/v) HGF.

In some embodiments, the composition has a pH of about 6.0.

In some embodiments, the pharmaceutical composition comprises about 150 to about 250 mM of stabilizer. In some embodiments, the pharmaceutical composition comprises about 200 mM of stabilizer. In some embodiments, the stabilizer is trehalose or proline. In some embodiments, the stabilizer is trehalose. In some embodiments, the stabilizer is proline. In some embodiments, the stabilizer is sorbitol.

In some embodiments, the buffer is a citrate buffer. In some embodiments, the buffer is sodium citrate. In some embodiments, the pharmaceutical composition comprises about 10 to about 50 mM of buffer.

In some embodiments, the osmolality of the composition is about 450 mOsm/kg $H_2O$.

In some embodiments, the pharmaceutical composition does not include a tonicity modifier. In some embodiments, the pharmaceutical composition comprises a tonicity modifier which is an alkali metal salt. In some embodiments, the pharmaceutical composition comprises a tonicity modifier which is sodium chloride.

In some embodiments, the pharmaceutical composition comprises a surfactant. In some embodiments, the surfactant is selected from polysorbate 80 (PS80), Polaxomer 188, and Polaxomer 407. In some embodiments, the surfactant is polysorbate 80 (PS80). In some embodiments, the surfactant is present in an amount of about 0.01% to about 0.1% (w/v). In some embodiments, the surfactant is present in an amount of about 0.02% to about 0.8% (w/v). In some embodiments, the surfactant is present in an amount of about 0.05% (w/v).

Also provided herein are aqueous pharmaceutical compositions comprising: about 0.1% (w/v) HGF; about 20 mM sodium citrate; about 200 mM of trehalose, proline, or sorbitol; about 0.05% (w/v) surfactant; wherein the pH of the composition is about 6.0 and the osmolality of the composition is about 350 mOsm/kg $H_2O$.

In some embodiments, the aqueous pharmaceutical composition comprises: about 0.1% (w/v) HGF; about 20 mM sodium citrate; about 200 mM of trehalose; about 0.05% (w/v) of polysorbate 80 (PS80); wherein the pH of the composition is about 6.0 and the osmolality of the composition is about 350 mOsm/kg $H_2O$.

In some embodiments, the aqueous pharmaceutical composition comprises: about 0.1% (w/v) HGF; about 20 mM sodium citrate; about 200 mM of proline; about 0.05% (w/v) of polysorbate 80 (PS80); wherein the pH of the composition is about 6.0 and the osmolality of the composition is about 350 mOsm/kg $H_2O$.

In some embodiments, the aqueous pharmaceutical composition comprises: about 0.1% (w/v) HGF; about 20 mM sodium citrate; about 200 mM of sorbitol; about 0.05% (w/v) of polysorbate 80 (PS80); wherein the pH of the composition is about 6.0 and the osmolality of the composition is about 350 mOsm/kg $H_2O$.

In some embodiments, the aqueous pharmaceutical composition comprises: about 0.2% (w/v) HGF; about 20 mM sodium citrate; about 200 mM of trehalose, proline, or sorbitol;

about 0.05% (w/v) surfactant; wherein the pH of the composition is about 6.0 and the osmolality of the composition is about 450 mOsm/kg $H_2O$.

In some embodiments, the aqueous pharmaceutical composition comprises: about 0.2% (w/v) HGF; about 20 mM sodium citrate; about 200 mM of trehalose; about 0.05% (w/v) of polysorbate 80 (PS80); wherein the pH of the composition is about 6.0 and the osmolality of the composition is about 450 mOsm/kg $H_2O$.

In some embodiments, the aqueous pharmaceutical composition comprises: about 0.2% (w/v) HGF; about 20 mM sodium citrate; about 200 mM of proline; about 0.05% (w/v) of polysorbate 80 (PS80); wherein the pH of the composition is about 6.0 and the osmolality of the composition is about 450 mOsm/kg $H_2O$.

In some embodiments, the aqueous pharmaceutical composition comprises: about 0.2% (w/v) HGF; about 20 mM sodium citrate; about 200 mM of sorbitol; about 0.05% (w/v) of polysorbate 80 (PS80); wherein the pH of the composition is about 6.0 and the osmolality of the composition is about 450 mOsm/kg $H_2O$.

In some embodiments, the HGF comprises a polypeptide sequence of any one of SEQ ID NOS: 1-27. In some embodiments, the HGF comprises a polypeptide sequence which has 95% sequence identity to SEQ ID NO: 1. In some embodiments, the HGF comprises a polypeptide sequence having SEQ ID NO: 1.

Also provided herein are methods of treating or preventing an eye disease in a subject in need thereof, the method comprising administering to the subject a therapeutically effective amount of a pharmaceutical composition described herein.

In some embodiments, the eye disease is a corneal disease selected from neurotrophic keratitis, persistent corneal defect, corneal ulcer, dry eye disease, microbial keratitis, bacterial keratitis, viral keratitis, fungal keratitis, chemical burn, thermal burn, mechanical trauma, corneal abrasion, compromised endothelium, bullous keratopathy, Fuch's corneal dystrophy, corneal scar, Sjogren's syndrome, or post-surgical complications. In some embodiments, the eye disease is corneal haze or scarring. In some embodiments, the eye disease is neurotrophic keratitis. In some embodiments, the composition is administered in combination with a corneal stroma permeating excipient.

In some embodiments, the composition is administered to the eye. In some embodiments, the composition is topically administered to the eye. In some embodiments, the composition is administered to the eye by injection. In some embodiments, the composition is administered subconjunctivally. In some embodiments, the composition is administered intracamerally.

In some embodiments of the methods or compositions described herein, the HGF is activated HGF. In some embodiments, the activated HGF is activated dHGF.

In some embodiments of the methods or compositions described herein, the HGF comprises:

(a) a first polypeptide comprising an amino acid sequence having at least 80%, preferably 90% identity to amino acids 32-494 of SEQ ID NO: 2; and a second polypeptide comprising an amino acid sequence having at least 80%, preferably 90% identity to amino acids 495-728 of SEQ ID NO: 2, optionally wherein the first polypeptide comprises a deletion of the amino acids corresponding to amino acids 161-165 of SEQ ID NO: 2; or (b) a first polypeptide comprising an amino acid sequence having at least 80%, preferably 90% identity to amino acids 32-494 of SEQ ID NO: 7; and a second polypeptide comprising an amino acid sequence having at least 80%, preferably 90% identity to amino acids 495-728 of SEQ ID NO: 7, optionally wherein the first polypeptide comprises a deletion of the amino acids corresponding to amino acids 161-165 of SEQ ID NO: 7; or (c) a first polypeptide comprising an amino acid sequence having at least 80%, preferably 90% identity to amino acids 32-494 of SEQ ID NO: 8; and a second polypeptide comprising an amino acid sequence having at least 80%, preferably 90% identity to amino acids 495-728 of SEQ ID NO: 8, optionally wherein the first polypeptide comprises a deletion of the amino acids corresponding to amino acids 161-165 of SEQ ID NO: 8; or (d) a first polypeptide comprising an amino acid sequence having at least 80%, preferably 90% identity to amino acids 32-494 of SEQ ID NO: 9; and a second polypeptide comprising an amino acid sequence having at least 80%, preferably 90% identity to amino acids 495-728 of SEQ ID NO: 9, optionally wherein the first polypeptide comprises a deletion of the amino acids corresponding to amino acids 161-165 of SEQ ID NO: 9; or (e) a first polypeptide comprising an amino acid sequence having at least 80%, preferably 90% identity to amino acids 32-494 of SEQ ID NO: 10; and a second polypeptide comprising an amino acid sequence having at least 80%, preferably 90% identity to amino acids 495-728 of SEQ ID NO: 10, optionally wherein the first polypeptide comprises a deletion of the amino acids corresponding to amino acids 161-165 of SEQ ID NO: 10; or (g) a first polypeptide comprising an amino acid sequence having at least 80%, preferably 90% identity to amino acids 32-494 of SEQ ID NO: 11; and a second polypeptide comprising an amino acid sequence having at least 80%, preferably 90% identity to amino acids 495-728 of SEQ ID NO: 11, optionally wherein the first polypeptide comprises a deletion of the amino acids corresponding to amino acids 161-165 of SEQ ID NO: 11; or (h) a first polypeptide comprising an amino acid sequence having at least 80%, preferably 90% identity to amino acids 32-494 of SEQ ID NO: 12; and a second polypeptide comprising an amino acid sequence having at least 80%, preferably 90% identity to amino acids 495-728 of SEQ ID NO: 12, optionally wherein the first polypeptide comprises a deletion of the amino acids corresponding to amino acids 161-165 of SEQ ID NO: 12; or (i) a first polypeptide comprising an amino acid sequence having at least 80%, preferably 90% identity to amino acids 32-494 of SEQ ID NO: 13; and a second polypeptide comprising an amino acid sequence having at least 80%, preferably 90% identity to amino acids 495-728 of SEQ ID NO: 13, optionally wherein the first polypeptide comprises a deletion of the amino acids corresponding to amino acids 161-165 of SEQ ID NO: 13; or (j) a first polypeptide comprising an amino acid sequence having at least 80%, preferably 90% identity to amino acids 32-494 of SEQ ID NO: 14; and a second polypeptide comprising an amino acid sequence having at least 80%, preferably 90% identity to amino acids 495-728 of SEQ ID NO: 14, optionally wherein the first polypeptide comprises a deletion of the amino acids corresponding to amino acids 161-165 of SEQ ID NO: 14; or (k) a first polypeptide comprising an amino acid sequence having at least 80%, preferably 90% identity to amino acids 32-494 of SEQ ID NO: 15; and a second polypeptide comprising an amino acid sequence having at least 80%, preferably 90% identity to amino acids 495-728 of SEQ ID NO: 15, optionally wherein the first polypeptide comprises a deletion of the amino acids corresponding to amino acids 161-165 of SEQ ID NO: 15; or (l) a first polypeptide comprising an amino acid sequence having at least 80%, preferably 90% identity to amino acids 32-494 of SEQ ID NO: 16; and a second polypeptide comprising an amino acid sequence having at least 80%, preferably 90% identity to amino acids 495-728 of SEQ ID NO: 16, optionally wherein the first polypeptide comprises a deletion of the amino acids corresponding to amino acids 161-165 of SEQ ID NO: 16; or (m) a first polypeptide comprising an amino acid sequence having at least 80%, preferably 90% identity to amino acids 32-494 of SEQ ID NO: 17; and a second polypeptide comprising an amino acid sequence having at least 80%, preferably 90% identity to amino acids 495-728 of SEQ ID NO: 17, optionally wherein the first polypeptide comprises a deletion of the amino acids corresponding to amino acids 161-165 of SEQ ID NO: 17; or (n) a first polypeptide comprising an amino acid sequence having at least 80%, preferably 90% identity to amino acids 32-494 of SEQ ID NO: 18; and a second polypeptide comprising an amino acid sequence having at least 80%, preferably 90% identity to amino acids 495-728 of SEQ ID NO: 18, optionally wherein the first polypeptide comprises a deletion of the amino acids corresponding to amino acids 161-165 of SEQ ID NO: 18; or (o) a first polypeptide comprising an amino acid sequence having at least 80%, preferably 90% identity to amino acids 32-494 of SEQ ID NO: 19; and a second polypeptide comprising an amino acid sequence having at least 80%, preferably 90% identity to amino acids 495-728 of SEQ ID NO: 19, optionally wherein the first polypeptide comprises a deletion of the amino acids corresponding to amino acids 161-165 of SEQ ID NO: 19; or (p) a first polypeptide comprising an amino acid sequence having at least 80%, preferably 90% identity to amino acids 32-494 of SEQ ID NO: 20; and a second polypeptide comprising an amino acid sequence having at least 80%, preferably 90% identity to amino acids 495-728 of SEQ ID NO: 20, optionally wherein the first polypeptide comprises a deletion of the amino acids corresponding to amino acids 161-165 of SEQ ID NO: 20; or (q) a first polypeptide comprising an amino acid sequence having at least 80%, preferably 90% identity to amino acids 32-494 of SEQ ID NO: 21; and a second polypeptide comprising an amino acid sequence having at least 80%, preferably 90% identity to amino acids 495-728 of SEQ ID NO: 21, optionally wherein the first polypeptide comprises a deletion of the amino acids corresponding to amino acids 161-165 of SEQ ID NO: 21; or (r) a first polypeptide comprising an amino acid sequence having at least 80%, preferably 90% identity to amino acids 32-494 of SEQ ID NO: 22; and a second polypeptide comprising an amino acid sequence having at least 80%, preferably 90% identity to amino acids 495-728 of SEQ ID NO: 22, optionally wherein the first polypeptide comprises a deletion of the amino acids corresponding to amino acids 161-165 of SEQ ID NO: 22; or (s) a first polypeptide comprising an amino acid sequence having at least 80%, preferably 90% identity to amino acids 32-494 of SEQ ID NO: 23; and a second polypeptide comprising an amino acid sequence having at least 80%, preferably 90% identity to amino acids 495-728 of SEQ ID NO: 23, optionally wherein the first polypeptide comprises a deletion of the amino acids corresponding to amino acids 161-165 of SEQ ID NO: 23; or (t) a first polypeptide comprising an amino acid sequence having at least 80%, preferably 90% identity to amino acids 32-494 of SEQ ID NO: 24; and a second polypeptide comprising an amino acid sequence having at least 80%, preferably 90% identity to amino acids 495-728 of SEQ ID NO: 24, optionally wherein the first polypeptide comprises a deletion of the amino acids corresponding to amino acids 161-165 of SEQ ID NO: 24; or (u)) a first polypeptide comprising an amino acid sequence having at least 80%, preferably 90% identity to amino acids 32-494 of SEQ ID NO: 25; and a second polypeptide comprising an amino acid sequence having at least 80%, preferably 90% identity to amino acids 495-728 of SEQ ID NO: 25, optionally wherein the first polypeptide comprises a deletion of the amino acids corresponding to amino acids 161-165 of SEQ ID NO: 25; or (v) a first polypeptide comprising an amino acid sequence having at least 80%, preferably 90% identity to amino acids 32-494 of SEQ ID NO: 26; and a second polypeptide comprising an amino acid sequence having at least 80%, preferably 90% identity to amino acids 495-728 of SEQ ID NO: 26, optionally wherein the first polypeptide comprises a deletion of the amino acids corresponding to amino acids 161-165 of SEQ ID NO: 26; or (w) a first polypeptide comprising an amino acid sequence having at least 80%, preferably 90% identity to amino acids 32-494 of SEQ ID NO: 27; and a second polypeptide comprising an amino acid sequence having at least 80%, preferably 90% identity to amino acids 495-728 of SEQ ID NO: 27, optionally wherein the first polypeptide comprises a deletion of the amino acids corresponding to amino acids 161-165 of SEQ ID NO: 27.

In some embodiments of the methods or compositions described herein, the HGF comprises:

(a) a first polypeptide comprising or consisting of an amino acid sequence corresponding to amino acids 32-494 of SEQ ID NO: 2; and a second polypeptide comprising or consisting of an amino acid sequence corresponding to amino acids 495-728 of SEQ ID NO: 2, optionally wherein the first polypeptide comprises a deletion of the amino acids corresponding to amino acids 161-165 of SEQ ID NO: 2; or (b) a first polypeptide comprising or consisting of an amino acid sequence corresponding to amino acids 32-494 of SEQ ID NO: 7; and a second polypeptide comprising or consisting of an amino acid sequence corresponding to amino acids 495-728 of SEQ ID NO: 7, optionally wherein the first polypeptide comprises a deletion of the amino acids corresponding to amino acids 161-165 of SEQ ID NO: 7; or (c) a first polypeptide comprising or consisting of an amino acid sequence corresponding to amino acids 32-494 of SEQ ID NO: 8; and a second polypeptide comprising or consisting of an amino acid sequence corresponding to amino acids 495-728 of SEQ ID NO: 8, optionally wherein the first polypeptide comprises a deletion of the amino acids corresponding to amino acids 161-165 of SEQ ID NO: 8; or (d) a first polypeptide comprising or consisting of an amino acid sequence corresponding to amino acids 32-494 of SEQ ID NO: 9; and a second polypeptide comprising or consisting of an amino acid sequence corresponding to amino acids 495-728 of SEQ ID NO: 9, optionally wherein the first polypeptide comprises a deletion of the amino acids corresponding to amino acids 161-165 of SEQ ID NO: 9; or (e) a first polypeptide comprising or consisting of an amino acid sequence corresponding to amino acids 32-494 of SEQ ID NO: 10; and a second polypeptide comprising or consisting of an amino acid sequence corresponding to amino acids 495-728 of SEQ ID NO: 10, optionally wherein the first polypeptide comprises a deletion of the amino acids corresponding to amino acids 161-165 of SEQ ID NO: 10; or (g) a first polypeptide comprising or consisting of an amino acid sequence corresponding to amino acids 32-494 of SEQ ID NO: 11; and a second polypeptide comprising or consisting of an amino acid sequence corresponding to amino acids 495-728 of SEQ ID NO: 11, optionally wherein the first polypeptide comprises a deletion of the amino acids corresponding to amino acids 161-165 of SEQ ID NO: 11; or (h) a first polypeptide comprising or consisting of an amino acid sequence corresponding to amino acids 32-494 of SEQ ID NO: 12; and a second polypeptide comprising or consisting of an amino acid sequence corresponding to amino acids 495-728 of SEQ ID NO: 12, optionally wherein the first polypeptide comprises a deletion of the amino acids corresponding to amino acids 161-165 of SEQ ID NO: 12; or (i) a first polypeptide comprising or consisting of an amino acid sequence corresponding to amino acids 32-494 of SEQ ID NO: 13; and a second polypeptide comprising or consisting of an amino acid sequence corresponding to amino acids 495-728 of SEQ ID NO: 13, optionally wherein the first polypeptide comprises a deletion of the amino acids corresponding to amino acids 161-165 of SEQ ID NO: 13; or (j) a first polypeptide comprising or consisting of an amino acid sequence corresponding to amino acids 32-494 of SEQ ID NO: 14; and a second polypeptide comprising or consisting of an amino acid sequence corresponding to amino acids 495-728 of SEQ ID NO: 14, optionally wherein the first polypeptide comprises a deletion of the amino acids corresponding to amino acids 161-165 of SEQ ID NO: 14; or (k) a first polypeptide comprising or consisting of an amino acid sequence corresponding to amino acids 32-494 of SEQ ID NO: 15; and a second polypeptide comprising or consisting of an amino acid sequence corresponding to amino acids 495-728 of SEQ ID NO: 15, optionally wherein the first polypeptide comprises a deletion of the amino acids corresponding to amino acids 161-165 of SEQ ID NO: 15; or (l) a first polypeptide comprising or consisting of an amino acid sequence corresponding to amino acids 32-494 of SEQ ID NO: 16; and a second polypeptide comprising or consisting of an amino acid sequence corresponding to amino acids 495-728 of SEQ ID NO: 16, optionally wherein the first polypeptide comprises a deletion of the amino acids corresponding to amino acids 161-165 of SEQ ID NO: 16; or (m) a first polypeptide comprising or consisting of an amino acid sequence corresponding to amino acids 32-494 of SEQ ID NO: 17; and a second polypeptide comprising or consisting of an amino acid sequence corresponding to amino acids 495-728 of SEQ ID NO: 17, optionally wherein the first polypeptide comprises a deletion of the amino acids corresponding to amino acids 161-165 of SEQ ID NO: 17; or (n) a first polypeptide comprising or consisting of an amino acid sequence corresponding to amino acids 32-494 of SEQ ID NO: 18; and a second polypeptide comprising or consisting of an amino acid sequence corresponding to amino acids 495-728 of SEQ ID NO: 18, optionally wherein the first polypeptide comprises a deletion of the amino acids corresponding to amino acids 161-165 of SEQ ID NO: 18; or (o) a first polypeptide comprising or consisting of an amino acid sequence corresponding to amino acids 32-494 of SEQ ID NO: 19; and a second polypeptide comprising or consisting of an amino acid sequence corresponding to amino acids 495-728 of SEQ ID NO: 19, optionally wherein the first polypeptide comprises a deletion of the amino acids corresponding to amino acids 161-165 of SEQ ID NO: 19; or (p) a first polypeptide comprising or consisting of an amino acid sequence corresponding to amino acids 32-494 of SEQ ID NO: 20; and a second polypeptide comprising or consisting of an amino acid sequence corresponding to amino acids 495-728 of SEQ ID NO: 20, optionally wherein the first polypeptide comprises a deletion of the amino acids corresponding to amino acids 161-165 of SEQ ID NO: 20; or (q) a first polypeptide comprising or consisting of an amino acid sequence corresponding to amino acids 32-494 of SEQ ID NO: 21; and a second polypeptide comprising or consisting of an amino acid sequence corresponding to amino acids 495-728 of SEQ ID NO: 21, optionally wherein the first polypeptide comprises a deletion of the amino acids corresponding to amino acids 161-165 of SEQ ID NO: 21; or (r) a first polypeptide comprising or consisting of an amino acid sequence corresponding to amino acids 32-494 of SEQ ID NO: 22; and a second polypeptide comprising or consisting of an amino acid sequence corresponding to amino acids 495-728 of SEQ ID NO: 22, optionally wherein the first polypeptide comprises a deletion of the amino acids corresponding to amino acids 161-165 of SEQ ID NO: 22; or (s) a first polypeptide comprising or consisting of an amino acid sequence corresponding to amino acids 32-494 of SEQ ID NO: 23; and a second polypeptide comprising or consisting of an amino acid sequence corresponding to amino acids 495-728 of SEQ ID NO: 23, optionally wherein the first polypeptide comprises a deletion of the amino acids corresponding to amino acids 161-165 of SEQ ID NO: 23; or (t) a first polypeptide comprising or consisting of an amino acid sequence corresponding to amino acids 32-494 of SEQ ID NO: 24; and a second polypeptide comprising or consisting of an amino acid sequence corresponding to amino acids 495-728 of SEQ ID NO: 24, optionally wherein the first polypeptide comprises a deletion of the amino acids corresponding to amino acids 161-165 of SEQ ID NO: 24; or (u)) a first polypeptide comprising or consisting of an amino acid sequence corresponding to amino acids 32-494 of SEQ ID NO: 25; and a second polypeptide comprising or consisting of an amino acid sequence corresponding to amino acids 495-728 of SEQ ID NO: 25, optionally wherein the first polypeptide comprises a deletion of the amino acids corresponding to amino acids 161-165 of SEQ ID NO: 25; or (v) a first polypeptide comprising or consisting of an amino acid sequence corresponding to amino acids 32-494 of SEQ ID NO: 26; and a second polypeptide comprising or consisting of an amino acid sequence corresponding to amino acids 495-728 of SEQ ID NO: 26, optionally wherein the first polypeptide comprises a deletion of the amino acids corresponding to amino acids 161-165 of SEQ ID NO: 26; or (w) a first polypeptide comprising or consisting of an amino acid sequence corresponding to amino acids 32-494 of SEQ ID NO: 27; and a second polypeptide comprising or consisting of an amino acid sequence corresponding to amino acids 495-728 of SEQ ID NO: 27, optionally wherein the first polypeptide comprises a deletion of the amino acids corresponding to amino acids 161-165 of SEQ ID NO: 27.

In some embodiments of the methods or compositions described herein, the first polypeptide comprises or consists of the amino acid sequence of SEQ ID NO: 36 and the second polypeptide comprises or consists of the amino acid sequence of SEQ ID NO: 37.

In some embodiments of the methods or compositions described herein, the N-terminal amino acid of the first polypeptide is pyrrolidone carboxylic acid.

In some embodiments of the methods or compositions described herein, the first polypeptide and second polypeptide are linked by one or more disulfide bonds.

In some embodiments of the methods or compositions described herein, the HGF is capable of binding to c-MET and/or activating the MAPK pathway in epithelial cells.

DETAILED DESCRIPTION

Figure 1:
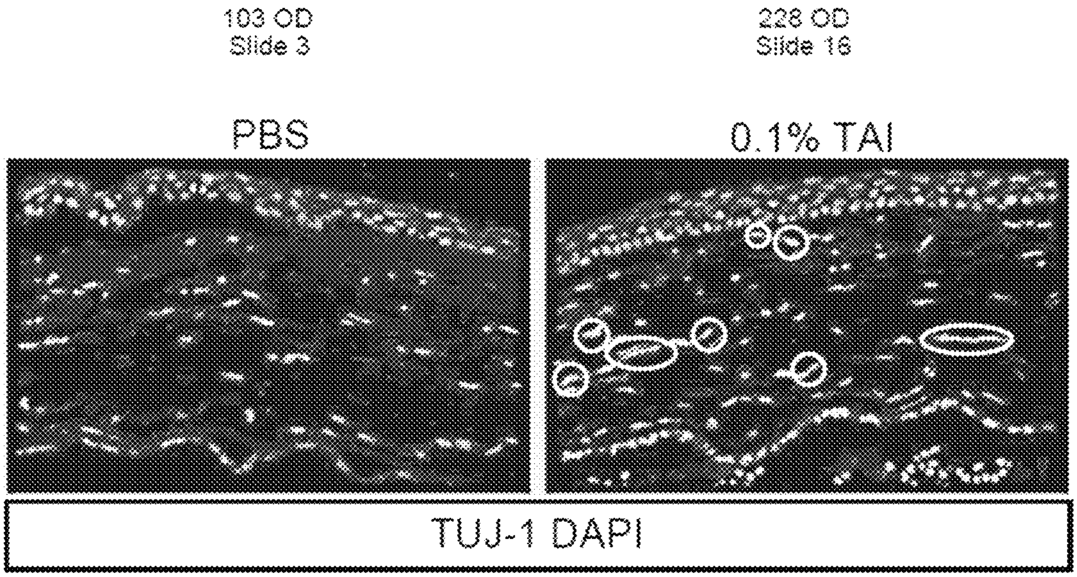
FIG. 1. Fluorescence microscopy images of slides containing serial sections of the mouse optic nerve to evaluate corneal innervation on Day 3 post-surgery. The tissue samples were stained for TUJ-1 (also known as beta III tubulin, circled areas) to evaluate corneal innervation. Animals treated with control (PBS) showed potentially lower TUJ-1 staining (circled areas) on Day 3 in comparison to eyes that received 0.1% dHGF (SEQ ID. NO. 1); DAPI was used as a counterstain to highlight all nuclei.

In some embodiments, the present invention provides, inter alia, a method of treating or preventing neurotrophic keratitis (NK) in a subject in need thereof, the method comprising administering to the subject hepatocyte growth factor (HGF) or a fibroblast growth factor (FGF).

Neurotrophic keratitis or, alternatively, neurotrophic keratopathy (NK) is a degenerative condition of the cornea resulting from damage to the trigeminal nerve or its branches, or compromised ocular surface, which leads to consequent reduction of corneal sensitivity or complete loss of corneal sensation. As used herein, the terms "disease", "condition", or "disorder," used interchangeably, refer to any of numerous pathological conditions of the affected tissue or organ. Impairment to the trigeminal nerve or its branches is most commonly caused by infections (e.g. viral infections including herpes simplex or zoster infections, bacterial ulcers, late *Acanthamoeba* ulcers), eye surgeries (e.g. cataract surgery, corneal transplantation, refractive surgery, and retinal surgery), other systemic diseases such as diabetes, leprosy, orbital tumors and inflammations, fifth nerve palsy due to trigeminal lesions in posterior fossa, aneurysm, acoustic neuroma, meningioma, or other physical damages to the corneal layers by chemical and thermal burns. Other causes of NK include genetic diseases (e.g. familiar corneal hypoesthesia, Goldenhar-Gorlin syndrome, hereditary sensory and autonomic neuropathy types III, IV or V, corneal dystrophies and multiple endocrine neoplasia IIb), use of certain drugs (e.g. topical beta-blockers, topical nonsteroidal anti-inflammatory (NSAID), topical anesthetics), and the use of contact lenses (for review, see Okada et al., supra).

NK can be treated or prevented according to the methods described herein, by the administration of hepatocyte growth factor (HGF) and/or fibroblast growth factor (FGF).

HGF (e.g., UniProt ID No. P14210)) is a cMet kinase agonist that, inter alia, stimulates epithelial cell proliferation, motility, morphogenesis, and angiogenesis in various organs via the tyrosine kinase signaling pathway, and plays major roles in embryonic organ development and adult organ regeneration and wound healing. HGF is an approximately 84 kDa protein comprising of two subunits: an α-subunit of an apparent molecular weight of 69 kDa and a β-subunit of an apparent molecular weight of 34 kDa linked by a single disulfide bond.

HGF is produced as a pro-HGF molecule of 728 amino acids by mesenchymal stromal cells (e.g. fibroblasts and macrophages) wherein the first 1-31 amino acid residues correspond to a secretion signaling sequence (Matsumoto and Nakamura, in *Encyclopedia of Endocrine Diseases*, Elsevier, 2004, 436-442). The primary amino acid sequence of Pro-HGF is organized into a domain structure of four Kringle (K) domains (Sigurdardottir, et al., 2015, Chem. Sci., 6:6147-6157). As used herein, a "Kringle" domain refers to a polypeptide linear sequence folded into triple-looped, disulfide cross-linked domains (Simonneau, et al., 2015, *Chem. Sci.*, 6:2110-2121). Kringle domains are present in a variety of polypeptides including apolipoprotein A, blood coagulation factor XII, plasminogen, and HGF. The name "Kringle" is derived from the Scandinavian pastry that these structures resemble. Kringle domains are believed to mediate binding interactions between proteins, membranes, and phospholipids. In some embodiments, polypeptides of the invention contain at least one Kringle domain.

Upon cleavage of the secretion signaling sequence, proteolytic cleavage at a trypsin-like site (R494-V495) between the fourth Kringle and the C-terminal serine-proteinase homology (SPH) domain of the pro-HGF yields the mature, activated HGF. A trypsin-like cleavage site is a peptide bond following a positively-charged amino acid (e.g. lysine or arginine). Upon activation, HGF binds to and activates its receptor, cMet (also known as the MET tyrosine kinase), which leads to tyrosine phosphorylation, further effecting the recruitment of a variety of downstream adaptor molecules and modulation of various intracellular pathways and biological activities collectively known as the invasive growth program (Nakamura, T., 1991, *Prog. Growth Factor Res.*, 3:67-85; Bottaro, et al., 1991, *Science* 251:802-804). HGF and its receptor cMet are both expressed in the corneal epithelium, stromal cells, endothelium and the lacrimal gland, albeit at extremely low levels with the amount of HGF in human tears estimated to be about 500 pg/mL (Wilson et al., 1993, *Invest. Ophthalmol. Vis. Sci.*, 34:2544-2561; Li et al., 1996, *Invest. Ophthalmol. Vis. Sci.*, 37:727-739).

Six naturally occurring isoforms of HGF resulting from alternative splicing of the HGF mRNA gene transcripts are known in the literature, among which, the major isoforms are isoforms 1 (e.g., SEQ ID NO: 2) and 2 (e.g., SEQ ID NO: 3) (Bottaro, et al., 1991, *Science*, 251:802-804; Chan et al., 1991, *Science*, 254:1382-1385; Lokker and Godowski, 1992, *EMBO J.*, 11:2503-2510; Cioce, et al., 1996, *J. Biol. Chem.*, 271:13110-13115). As used herein, the term "isoform" refers to proteins that result from alternative splicing of the pre-mRNA encoding HGF. The isoform 1 mRNA transcript encodes the longest HGF gene sequence, which comprises 728 amino acid residues. The second major HGF isoform is encoded by the mRNA transcript of isoform 2, which lacks multiple 3' exons but includes an alternate 3' exon relative to the isoform 1 transcript. The HGF protein encoded by the isoform 2 mRNA transcript comprises 290 amino acid residues, and is truncated after the second Kringle domain as compared to the isoform 1 HGF protein (Miyazawa, et al., 1991, *Eur. J. Biochem.*, 197:15-22). The isoform 3 mRNA transcript lacks an in-frame coding segment present in isoform 1, and encodes an HGF protein comprising 723 amino acid residues (e.g., SEQ ID NO: 1) lacking the sequence "SFLPS" (SEQ ID NO: 38) at positions 161-165 within the first Kringle domain of isoform 1 (Rubin et al., 1991, *Proc. Natl. Acad. Sci.*, 88:415-419). The isoform 4 HGF protein (e.g., SEQ ID NO: 4) is a smaller molecule comprising residues 1-296, wherein the amino acid sequence extends only through the second Kringle domain (Chan et al., 1991, *Science*, 254:1382-1385). The isoform 5 HGF protein (e.g., SEQ ID NO: 5) is similar to the isoform 2 HGF protein with the additional deletion of residues 161-165 (SFLPS; SEQ ID NO: 38) as in isoform 3 HGF (Rubin et al., 1991, *Proc. Natl. Acad. Sci.*, 88:415-419). The isoform 6 HGF protein (also known as NK1) (e.g., SEQ ID NO: 6) is the smallest of all HGF isoforms, comprising only 210 amino acids (Cioce, et al., 1996, *J. Bio. Chem.*, 271:13110-13115).

Both the full length and truncated isoforms of HGF have been shown to bind to cMet, albeit with different potency and interactions with heparin sulfate proteoglycan of the extracellular matrix, which help prolong the circulating half-lives of HGF in vivo (Masumoto and Yamamoto, 1991, *Biochem. Biophys. Res. Commun.,* 174:90-95; Montesano, et al., 1998, *Cell Growth Differ.,* 9:355-365; Sakata et al., 1997, *J. Biol. Chem.,* 272:9457-9463; Stahl et al., 1997, *Biochem.* 1, 326:763-772). While isoforms 1 and 3 require the proteolytic cleavage at R494-V495 to become biologically active, the truncated isoforms 2, 4, 5 and 6 do not possess the R494-V495 cleavage site and as such, this activation step is not required for their biological activities. However, the truncated isoforms 2, 4, 5 and 6 are known to be generally less potent than the full length isoforms 1 and 3 counterparts (Stahl et al., 1997; Montesano, et al., 1998; supra).

The fibroblast growth factors (FGFs) are a family of cell signaling proteins that are involved in a wide range of biological processes including development. The human FGF family includes 22 members: FGF1, FGF2, FGF3 (INT2), FGF4, FGF5, FGF6, FGF7 (KGF), FGF8 (AIGF), FGF9, FGF10, FGF11, FGF12, FGF13, FGF14, FGF16, FGF17, FGF18, FGF19, FGF20, FGF21, FGF22, and FGF23.

FGFs exert their biological effects through binding and activating fibroblast growth factor receptors (FGFRs). Activated FGFRs mediate signaling by recruiting specific molecules that bind to phosphorylated tyrosine at the cytosolic part of the receptor, triggering a number of signaling pathways leading to specific cellular responses. The human FGFR family includes 4 members: FGFR1, FGFR2, FGFR3, and FGFR4.

In some embodiments, the HGF is a polypeptide comprising the amino acid sequence of any one of SEQ ID NOS: 1-27, with or without the signal sequence (i.e., the amino acids corresponding to amino acids 1-31 of SEQ ID NO: 1). In some embodiments, the HGF is a polypeptide comprising the amino acid sequence of SEQ ID NO: 1 or SEQ ID NO: 2, with or without the signal sequence (i.e., the amino acids corresponding to amino acids 1-31 of SEQ ID NO: 1 or SEQ ID NO: 2). In some embodiments, the HGF is a polypeptide comprising the amino acid sequence of SEQ ID NO: 1, with or without the signal sequence (i.e., the amino acids corresponding to amino acids 1-31 of SEQ ID NO: 1). In some embodiments, the HGF is a polypeptide comprising the amino acid sequence of SEQ ID NO: 2, with or without the signal sequence (i.e., the amino acids corresponding to amino acids 1-31 of SEQ ID NO: 2). In some embodiments, the HGF is a polypeptide comprising an activated form the amino acid sequence of SEQ ID NO. 1 or SEQ ID NO. 2. The term "activated form" refers to, inter alia, an HGF polypeptide from which the signal sequence (e.g. amino acids 1-31 of SEQ ID NO: 1 or SEQ ID NO: 2) has been cleaved and that has been cleaved between R489 and V490 of SEQ ID NO:1 or between R494 and V495 of SEQ ID NO:2 to form the disulfide-linked alpha and beta chains of HGF. In some embodiments, the N-terminal amino acid (e.g., amino acid 32 of SEQ ID NO: 1 or SEQ ID NO: 2) is pyrrolidone carboxylic acid, e.g., resulting from cleavage of the signal sequence. In some embodiments, polypeptides of the invention exist in the HGF precursor (pro-HGF) form wherein the peptide bond between R489 and V490 of SEQ ID NO:1 or R494 and V495 of SEQ ID NO:2 is intact. In some embodiments, polypeptides of the invention can be converted to an active form by proteolytic cleavage of a trypsin-like cleavage site between the R489 and V490 amino acid residues of SEQ ID NO:1 or between the R494 and V495 amino acid residues of SEQ ID NO:2 pro-HGF protein in vivo. In some embodiments, polypeptides of the invention can be converted to an active form by proteolytic cleavage of a trypsin-like cleavage site between the R489 and V490 amino acid residues of SEQ ID NO:1 or between the R494 and V495 amino acid residues of SEQ ID NO:2 pro-HGF protein in vitro. In some embodiments, the HGF is a polypeptide comprising the amino acid sequence of amino acids 32-723 of SEQ ID NO:1 pro-HGF protein. In some embodiments, the HGF is a polypeptide comprising the amino acid sequence of amino acids 32-723 of SEQ ID NO:1 activated protein. In some embodiments, the HGF is a polypeptide comprising the amino acid sequence of amino acids 32-728 of SEQ ID NO:2 pro-HGF protein. In some embodiments, the HGF is a polypeptide comprising the amino acid sequence of amino acids 32-728 of SEQ ID NO:2 activated protein.

In some embodiments, the HGF is a polypeptide comprising the amino acid sequence of SEQ ID NO: 3, 4, 5, or 6, with or without the signal sequence (e.g., the amino acids corresponding to amino acids 1-31 of SEQ ID NO: 3, 4, 5, or 6).

In some embodiments, the HGF is a polypeptide variant of SEQ ID NO: 1, SEQ ID NO: 2, SEQ ID NO: 3, SEQ ID NO: 4, SEQ ID NO: 5, or SEQ ID NO: 6, with or without the signal sequence (e.g., the amino acids corresponding to amino acids 1-31 of SEQ ID NO: 1, SEQ ID NO: 2, SEQ ID NO: 3, SEQ ID NO: 4, SEQ ID NO: 5, or SEQ ID NO: 6). As used herein, the term "variant" is meant to indicate a polypeptide differing from another polypeptide by one or more amino acid substitutions, deletions or insertions resulting from mutations in the nucleic acid coding for the polypeptide. In some embodiments, the HGF is a polypeptide comprising an amino acid sequence having at least 90% sequence identity to SEQ ID NO:1, SEQ ID NO: 2, or SEQ ID NO:6, with or without the signal sequence (e.g., the amino acids corresponding to amino acids 1-31 of SEQ ID NO: 1, SEQ ID NO: 2, or SEQ ID NO: 6). In some embodiments, the HGF is a polypeptide comprising an amino acid sequence having at least 95% sequence identity to SEQ ID NO:1, SEQ ID NO: 2, or SEQ ID NO:6, with or without the signal sequence (e.g., the amino acids corresponding to amino acids 1-31 of SEQ ID NO: 1, SEQ ID NO: 2, or SEQ ID NO: 6). In some embodiments, the HGF is a polypeptide comprising an amino acid sequence having at least 98% sequence identity to SEQ ID NO:1, SEQ ID NO: 2, or SEQ ID NO:6, with or without the signal sequence (e.g., the amino acids corresponding to amino acids 1-31 of SEQ ID NO: 1, SEQ ID NO: 2, or SEQ ID NO: 6). In some embodiments, the HGF is a polypeptide comprising an amino acid sequence having at least 99% sequence identity to SEQ ID NO:1, SEQ ID NO: 2, or SEQ ID NO:6, with or without the signal sequence (e.g., the amino acids corresponding to amino acids 1-31 of SEQ ID NO: 1, SEQ ID NO: 2, or SEQ ID NO: 6). In some embodiments, the HGF variant can (1) bind to c-MET and/or (2) activate the MAPK pathway in epithelial cells (e.g., human corneal epithelial cells).

In some embodiments, the HGF is a polypeptide comprising a mutation in an amino acid sequence of wild-type HGF isoform 1 (e.g., SEQ ID NO: 2), with or without the signal sequence (e.g., the amino acids corresponding to amino acids 1-31 of SEQ ID NO: 2) at one or more of positions 62, 64, 77, 95, 125, 127, 130, 132, 137, 142, 148, 154, 170, 173 and 193. In some embodiments, analogous positions in wild-type HGF isoform 3 (e.g., SEQ ID NO: 1) are mutated. In some embodiments, the HGF is a polypeptide comprising a mutation in an amino acid sequence as shown below in Table 1 and Table 2. Any combination of mutations shown in Table 1 and Table 2 can be included in the HGF polypeptides disclosed herein.

TABLE 1

Sequence mutations in HGF variants.
SEQ ID NO: 2 is wild-type. Only differences front wild-type sequence are shown in SEQ ID NOs: 7-16. blank spaces mean that the wild-type HGF residue is retained

| SEQ ID NO | Iso-form | bp | AA | 28 | 30 | 33 | 37 | 38 | 42 | 44 | 48 | 58 | 62 | 64 | 65 | 75 | 77 | 82 | 95 |
|---|---|---|---|---|---|---|---|---|---|---|---|---|---|---|---|---|---|---|---|
| 2 | 1 | | | Y | E | R | N | T | F | K | T | K | K | V | N | T | N | F | Q |
| 7 | 1 | 15 | 12 | | | | | | | | | R | E | A | | | S | | R |
| 8 | 1 | 21 | 15 | | | | | | | | | | E | A | | I | | | R |
| 9 | 1 | 16 | 14 | | | | | | | | | | E | A | | | S | | R |
| 10 | 1 | 18 | 15 | | K | G | | | | | | | E | A | D | | S | | |
| 11 | 1 | 19 | 15 | | | | | | | | A | R | E | A | | | S | | R |
| 12 | 1 | 20 | 15 | | | | | | | | | | E | A | | | S | | R |
| 13 | 1 | 16 | 13 | | | | | | | | | | E | A | | I | | | |
| 14 | 1 | 28 | 20 | | | | D | A | C | R | | | E | A | | | | S | R |
| 15 | 1 | 14 | 12 | | | G | | | | | | | E | | | | S | | R |
| 16 | 1 | 17 | 15 | H | | | | | | | | | E | A | | | S | | R |

| SEQ ID NO | 96 | 98 | 101 | 123 | 125 | 127 | 130 | 132 | 135 | 137 | 142 | 148 | 154 | 168 | 170 | 173 | 181 | 190 | 193 |
|---|---|---|---|---|---|---|---|---|---|---|---|---|---|---|---|---|---|---|---|
| 2 | C | W | F | D | I | N | I | K | S | K | I | K | S | R | K | Q | R | F | N |
| 7 | | | | | | D | | | | R | | | A | | E | R | | Y | D |
| 8 | | | V | | T | | V | N | | R | T | | A | | E | R | | Y | D |
| 9 | | | | | | D | V | N | | R | | E | A | | E | R | | Y | D |
| 10 | | | | | | D | V | N | | R | V | | E | | | R | | Y | D |
| 11 | | | | | | D | V | N | | R | | E | | | E | | W | Y | D |
| 12 | | | | | T | | V | N | | R | | E | A | Q | E | R | | Y | D |
| 13 | | | | A | | D | | R | N | R | | E | | | E | R | | Y | D |
| 14 | R | R | | | T | | V | N | | R | T | | A | | E | R | W | | D |
| 15 | | | | | | D | | R | | R | | | A | | E | R | | Y | D |
| 16 | | | | | T | | V | N | | R | T | | A | | E | R | | Y | D |

bp: number of base pair mutations
AA: number of amino acid mutations

TABLE 2

Sequence mutations in HGF variants.
SEQ ID NO: 2 is wild-type. Only differences from wild-type sequence are shown in SEQ ID NOs: 17-27. blank spaces mean that the wild-type HGF residue is retained.

| SEQ ID NO | Iso-form | bp | AA | 30 | 33 | 46 | 58 | 62 | 64 | 65 | 75 | 77 | 78 | 79 | 95 | 101 |
|---|---|---|---|---|---|---|---|---|---|---|---|---|---|---|---|---|
| 2 | 1 | | | E | R | A | K | K | V | N | T | N | K | G | Q | F |
| 17 | 1 | 17 | 13 | | | | | E | A | | | S | R | | | |
| Is | 1 | 16 | 11 | | | | | E | A | | | | | | R | |
| 19 | 1 | 20 | 17 | | | V | | E | A | | | S | | | R | V |

TABLE 2-continued

Sequence mutations in HGF variants. SEQ ID NO: 2 is wild-type. Only differences from wild-type sequence are shown in SEQ ID NOs: 17-27. blank spaces mean that the wild-type HGF residue is retained.

| | | | | | | | | | | | | | | | |
|---|---|---|---|---|---|---|---|---|---|---|---|---|---|---|---|
| 20 | 1 | 18 | 13 | | | | | E | A | | | S | | | R |
| 21 | 1 | 17 | 13 | | | | R | E | A | | | S | R | | R |
| 22 | 1 | 21 | 16 | | | | | E | A | | | S | R | R | R |
| 23 | 1 | 16 | 14 | | | | | E | A | | | S | | | R |
| 24 | 1 | 14 | 9 | | | | | | | D | | | | | R |
| 25 | 1 | 24 | 16 | | G | | R | E | A | | | S | | | R |
| 26 | 1 | 21 | 15 | K | | | R | E | | | I | | | | R |
| 27 | 1 | 14 | 12 | | G | | | E | | | | S | | | R |

| SEQ ID NO | 112 | 123 | 127 | 130 | 132 | 135 | 137 | 142 | 148 | 154 | 166 | 170 | 173 | 181 | 190 | 193 |
|---|---|---|---|---|---|---|---|---|---|---|---|---|---|---|---|---|
| 2 | F | D | N | I | K | S | K | I | K | S | S | K | Q | R | F | N |
| 17 | | | D | | N | | R | V | | A | | E | R | | Y | D |
| 18 | | | D | V | N | | R | | | | | E | R | | Y | D |
| 19 | S | | D | V | N | | R | T | | A | | E | R | | Y | D |
| 20 | | | D | V | N | | R | | | | | E | R | W | Y | D |
| 21 | | | D | | N | | R | | | | | E | R | | Y | D |
| 22 | | | D | | | | R | V | E | A | N | E | R | | Y | D |
| 23 | | | D | V | N | | R | | E | A | | E | R | | Y | D |
| 24 | | | D | | N | | R | | | | | E | R | | Y | D |
| 25 | | A | D | | R | N | R | | | A | | E | R | | Y | D |
| 26 | | A | D | | R | N | R | | | A | | E | R | | Y | D |
| 27 | | | D | | N | | R | | | A | | E | R | | Y | D |

bp: number of base pair mutations
AA: number of amino acid mutations

In some embodiments, the HGF is a polypeptide comprising an amino acid sequence selected from the group consisting of SEQ ID NOs: 7-27, with or without the signal sequence (e.g., the amino acids corresponding to amino acids 1-31 of SEQ ID NOs: 7-27). In some embodiments, the HGF is a polypeptide consisting of an amino acid sequence selected from the group consisting of SEQ ID NOs: 7-27, with or without the signal sequence (e.g., the amino acids corresponding to amino acids 1-31 of SEQ ID NOs: 7-27).

In some embodiments, the FGF is a polypeptide comprising the amino acid sequence of SEQ ID NO: 28. In some embodiments, the FGF is a polypeptide variant of SEQ ID NO: 28. In some embodiments, the FGF is a polypeptide comprising an amino acid sequence having at least 90%, at least 95%, at least 98%, or at least 99% sequence identity to SEQ ID NO: 28. In some embodiments, the FGFs variant exhibits increased proteolytic stability as compared to wild-type FGF1.

In some embodiments, the FGF is a polypeptide comprising a mutation in an amino acid sequence of wild-type FGF isoform 1 (e.g., SEQ ID NO: 28) at one or more of positions 28, 40, 47, 93 or 131. Any combination of mutations at positions 28, 40, 47, 93, and 131 can be included in the FGF polypeptides disclosed herein.

In some embodiments, the FGF1 variant comprises at least one amino acid substitution selected from the group consisting of D28N, Q40P, S47I, H93G, L131R, and L131K. In some embodiments, the FGF1 variant comprises amino acid substitution L131R. In some embodiments, the FGF1 variant comprises amino acid substitution L131K. In some embodiments, the variant comprises amino acid substitutions D28N and L131R (e.g., SEQ ID NO: 29). In some embodiments, the variant comprises amino acid substitutions D28N and L131K. In some embodiments, the variant comprises amino acid substitutions Q40P, S47I, and H93G (e.g., SEQ ID NO: 30). In some embodiments, the variant comprises amino acid substitutions Q40P, S47I, H93G, and L131R. In some embodiments, the variant comprises amino acid substitutions Q40P, S47I, H93G, and L131K. In some embodiments, the variant comprises amino acid substitutions D28N, Q40P, S47I, H93G, and L131R (e.g., SEQ ID NO: 31). In some embodiments, the variant comprises amino acid substitutions D28N, Q40P, S47I, H93G, and L131K. In some embodiments, the FGF1 variant does not comprise the amino acid substitution L131A.

In some embodiments, the FGF is a polypeptide comprising an amino acid sequence selected from the group consisting of SEQ ID NOs: 29-33. In some embodiments, the FGF is a polypeptide having an amino acid sequence selected from the group consisting of SEQ ID NOs: 29-33.

The polypeptides disclosed herein (e.g., HGF polypeptides, FGF polypeptides) can be monomers or dimers. In some embodiments, the HGF is a covalent dimer of a polypeptide, or a polypeptide variant thereof, of any one of any one of SEQ ID NOs: 1-27 (with or without the signal sequence (e.g., the amino acids corresponding to amino acids 1-31 of SEQ ID NOs: 1-27). In some embodiments, the FGF is a covalent dimer of a polypeptide, or a polypeptide variant thereof, of any one of SEQ ID NOs: 29-33. Covalent dimers of the HGF or FGF polypeptides can be obtained by expressing in a suitable expression system (for example, yeast or *E. coli*) any one of the HGF polypeptide sequences of SEQ ID NOs: 1-27, or a variant thereof, whereas a single amino acid residues, in particular, the N-terminus amino acid residue, is replaced with a cysteine residue. The expressed and, e.g., signal sequence cleaved, HGF polypeptide monomer or the expressed FGF polypeptide monomer can be induced to dimerize via the formation of a disulfide bond between the introduced cysteine residue (see, for example, Liu, et al., 2014, *FEBS Letters,* 588:4831-4837; Jones I I, et al., 2011, *Proc. Natl. Acad. Sci.,* 108:13035-13040; and U.S. Ser. No. 15/365,514).

In some cases, the HGF polypeptides described herein comprise one or more post-translational modifications, including for example, one or more of the following:

| Feature key | Position(s) | Description |
|---|---|---|
| Modified residue | 32 | Pyrrolidone carboxylic acid |
| Disulfide bond | 70 ↔ 96 | |
| Disulfide bond | 74 ↔ 84 | |
| Disulfide bond | 128 ↔ 206 | |
| Disulfide bond | 149 ↔ 189 | |
| Disulfide bond | 177 ↔ 201 | |
| Disulfide bond | 211 ↔ 288 | |
| Disulfide bond | 232 ↔ 271 | |
| Disulfide bond | 260 ↔ 283 | |
| Glycosylation | 294 | N-linked (GlcNAc . . .) (complex) asparagine |
| Disulfide bond | 305 ↔ 383 | |
| Disulfide bond | 326 ↔ 365 | |
| Disulfide bond | 354 ↔ 377 | |
| Disulfide bond | 391 ↔ 469 | |
| Glycosylation | 402 | N-linked (GlcNAc . . .) (complex) asparagine |
| Disulfide bond | 412 ↔ 452 | |
| Disulfide bond | 440 ↔ 464 | |
| Glycosylation | 476 | O-linked (GalNAc . . .) threonine |
| Disulfide bond | 487 ↔ 604 | Interchain (between alpha and beta chains) |
| Disulfide bond | 519 ↔ 535 | |
| Glycosylation | 566 | N-linked (GlcNAc . . .) (complex) asparagine |
| Disulfide bond | 612 ↔ 679 | |
| Disulfide bond | 642 ↔ 658 | |
| Glycosylation | 653 | N-linked (GlcNAc . . .) (complex) asparagine |
| Disulfide bond | 669 ↔ 697 | |

The polypeptides disclosed herein (e.g., HGF polypeptides, FGF polypeptides) can include a substitution with a naturally occurring amino acid or a non-naturally occurring amino acid including, but not limited to, hydroxyproline (Hyp), beta-alanine, citrulline (Cit), ornithine (Orn), norleucine (Nle), 3-nitrotyrosine, nitroarginine, and pyroglutamic acid (Pyr). In some cases, the HGF polypeptides are modified post-translationally, e.g., as shown in the table above.

As used herein, the term "sequence identity" refers to the percentage of identical residues between two polypeptide or nucleic acid sequences. One skilled in the art can readily determine sequence identity to an amino acid of HGF or FGF, for example, by using the Basic Local Alignment Search Tool (BLAST) available online at ≤https://blast.ncbi.nlm.nih.gov/Blast.cgi≥ by inputting the amino acid (or nucleic acid) sequences of HGF or FGF and the polypeptide (or nucleic acid) in question. The program BLAST can, for example, be used to align two sequences (with default parameters) as described by Tatiana A. Tatusova and Thomas L. Madden (1999), "Blast 2 sequences—a new tool for comparing protein and nucleotide sequences", *FEMS Microbiol Lett.* 174:247-250. Various other algorithms and software that may be used to obtain alignments of amino acid or nucleotide sequences are well-known in the art. These include, but are not limited to, ALIGN, Megalign, BestFit, GCG Wisconsin Package, and variants thereof. In some embodiments, polypeptides of the invention have at least about 50%, at least about 60%, at least about 70%, at least about 80%, at least about 85%, at least about 90%, at least about 95%, at least about 97%, at least about 98%, or at least about 99% homology with HGF, as ascertained for example by using the program BLAST to align two sequences (default parameters). In some instances, the sequences are substantially identical over the full length of the sequences being compared, for example, (i) the coding region of a nucleotide sequence or (ii) an amino acid sequence.

In some embodiments, the HGF and/or FGF is isolated from a biological source such as amniotic membrane or fluid, cells or tissues that produce HGF and/or FGF (e.g., mesenchymal stroma cells or hepatocytes), or tear fluid. In some embodiments, the HGF is a recombinant protein expressed in a suitable host protein expression system such as, for example, *E. coli, Saccharomyces cerevisiae*, Chinese hamster ovary (CHO) cells, human embryonic kidney (HEK293) cells, or insect cell lines (e.g. Sf9, Sf21 or S2). In some embodiments, the HGF is purified. As used herein, a "purified" HGF refers to a polypeptide that has been processed to remove other undesired components or contaminants. In some embodiments, the FGF is a recombinant protein expressed in a suitable host protein expression system such as, for example, *E. coli, Saccharomyces cerevisiae*, Chinese hamster ovary (CHO) cells, human embryonic kidney (HEK293) cells, or insect cell lines (e.g., Sf9, Sf21 or S2). In some embodiments, the FGF is purified. As used herein, a "purified" FGF refers to a polypeptide that has been processed to remove other undesired components or contaminants.

Examples of undesired components or contaminants removed during a purification process include cells, tissues, nucleic acids, polypeptides that are not related to HGF and/or FGF (e.g. host cell proteins from the expression system used, or abundant proteins from biological source where it is isolated from, e.g., albumin and immunoglobulins), small fragments of the HGF and/or FGF having less than 50% sequence homology, metals, and other inorganic salts. Examples of purification processes used by those skilled in the art include: precipitation, flocculation, tangential-flow filtration (TFF), ultra-filtration (UF), diafiltration (DF), dialysis, gel filtration chromatography (GFC), liquid chromatography (LC), ion-exchange chromatography (IEX), hydrophobic-interaction chromatography (HIC), and electrophoresis. In some embodiments, the purity of the purified HGF is at least about 50%. In some embodiments, the purity of the purified HGF is at least about 60%. In some embodiments, the purity of the purified HGF is about 75%. In some embodiments, the purity of the purified HGF is about 80%. In some embodiments, the purity of the purified HGF is about 85%. In some embodiments, the purity of the purified HGF is about 90%. In some embodiments, the purity of the purified HGF is about 95%. In a preferred embodiment, the purity of the purified HGF is about 97%. In some embodiments, the purity of the purified FGF is at least about 50%. In some embodiments, the purity of the purified FGF is at least about 60%. In some embodiments, the purity of the purified FGF is about 75%. In some embodiments, the purity of the purified FGF is about 80%. In some embodiments, the purity of the purified FGF is about 85%. In some embodiments, the purity of the purified FGF is about 90%. In some embodiments, the purity of the purified FGF is about 95%. In a preferred embodiment, the purity of the purified FGF is about 97%.

Determination of the purity and content of HGF and/or FGF can be readily achieved by one skilled in the art using conventional analytical assays and methods, for example, by reversed-phase high performance liquid chromatograph (RP-HPLC), size-exclusion chromatography (SEC), ion-exchange chromatography (IEX), polyacrylamide gel electrophoresis (PAGE), capillary gel electrophoresis (CGE) and Western blots.

As used herein, "polypeptides" or "proteins" are polymers of amino acids having, for example, from 2 to about 1000 or more amino acid residues. In some embodiments, "polypeptides" have from 10 to about 130 amino acids, from 10 to about 220 amino acids, from 10 to about 500 amino acids, or from 10 to about 730 amino acids. Any naturally occurring or synthetic amino acid can form the polypeptide. Polypeptides can also include modifications such as glycosylations and other moieties. In some embodiments, polypeptides of the invention have the ability to selectively bind to target polypeptides based on, for example, amino acid sequence of the target, such as amino acid sequences of the N- or C-terminus.

As used herein, the term "about" is used to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

Therapeutic and Prophylactic Methods

This disclosure features methods of treating or preventing eye disease or disorder in a subject. In some embodiments, the eye disease or disorder is a corneal disease. Non-limiting examples of corneal diseases include neurotrophic keratitis, persistent corneal defect, corneal ulcer, dry eye disease, microbial keratitis, bacterial keratitis, viral keratitis, fungal keratitis, chemical burn, thermal burn, mechanical trauma, corneal abrasion, compromised endothelium, bullous keratopathy, Fuch's corneal dystrophy, corneal scar, Sjogren's syndrome, and post-surgical complications. In some embodiments, the disease or disorder is corneal injury, including corneal haze or scarring. In some embodiments, the disease is neuropathic keratitis. The method involves administering to the subject a therapeutically effective amount of a HGF and/or FGF polypeptide as described herein. As used herein, "subject" or "patient," used interchangeably, include mammals, such as human, bovine, equine, canine, feline, porcine, and ovine animals. The subject is preferably a human.

In some embodiments, the subject has NK where there is an impairment to the trigeminal nerve or its branches. In certain cases, the impairment to the trigeminal nerve or its branches is caused by infections (e.g. bacterial or viral infections such as herpes simplex or zoster infections). In certain cases, the impairment to the trigeminal nerve or its branches is caused by eye surgeries (e.g. cataract surgery, corneal transplantation, refractive surgery). In certain cases, the impairment to the trigeminal nerve or its branches is caused by systemic diseases such as diabetes, leprosy, orbital tumors, and inflammations. In some cases, the impairment to the trigeminal nerve or its branches is caused by or physical trauma including chemical and thermal burns. In other cases, the impairment to the trigeminal nerve or its branches is caused by the use of contact lenses. In some embodiments, the subject has NK where there is damage to the epithelium not associated with any perturbations to the trigeminal nerve pathways.

In some embodiments, the HGF and/or FGF is administered to the eye of the subject. The route of HGF and/or FGF administration can be carried out in accord with known methods, e.g., topically via eye drops or bandage contact lens, local ocular injections (e.g., subconjunctival, intravitreal, retrobulbar, and intracameral), or by sustained release systems as noted below. In some embodiments, the HGF and/or FGF is administered topically to the eye. The term "topically" refers to applying the HGF and/or FGF directly on the surface (i.e. the cornea) of the eye. In some embodiments, the HGF and/or FGF is administered to the eye by injection. In some embodiments, the HGF and/or FGF is administered subconjunctivally. The term "subconjunctival" refers to an injection given either under the eyeball conjunctiva (epibulbar) or underneath the conjunctiva lining of the eyelid (subpalpebral) (Stanley, R., 2008 "Ocular Clinical Pharmacology" in *Small Animal Clinical Pharmacology* ($2^{nd}$ *Ed.*)). In some embodiments, the HGF and/or FGF is administered intravitreally. The term "intravitreal" refers to an injection given directly into the vitreous cavity of an eye. In some embodiments, the HGF and/or FGF is administered intracamerally. The term "intracameral" refers to an injection given directly into the anterior chamber of an eye. Therapeutic polypeptide compositions intended for injection are generally placed into a sterile container having a suitable access port, for example, a vial having a stopper pierceable by a hypodermic injection needle. For topical administration, the pharmaceutical composition comprising HGF and/or FGF can be placed in a squeezable eye-drop container. In some embodiments, the pharmaceutical composition comprising HGF and/or FGF is administered topically using the ophthalmic squeeze dispenser such as, for example, a dispenser from Aptar Pharma.

Suitable examples of sustained-release preparations include semipermeable polymer matrices in the form of shaped articles, e.g. films, implants, or microcapsules. Sustained release matrices include polyesters, hydrogels, polylactides (U.S. Pat. No. 3,773,919 and EP 58,481), copolymers of L-glutamic acid and gamma ethyl-L-glutamate (Sidman et al., 1983, *Biopolymers,* 22:547-556), poly (2-hydroxyethyl-methacrylate) (Langer et al., 1981, *J. Biomed. Mater. Res.,* 15:267-277 and Langer, 1982, *Chem. Tech.,* 12:98-105), ethylene vinyl acetate (Langer et al., supra) or poly-D-(−)-3-hydroxybutyric acid (EP 133,988). Sustained-release compositions also include liposomally-entrapped HGF, FGF, or both HGF and FGF. Liposomes containing HGF, FGF, or both HGF and FGF can be prepared by methods known per se: DE 3,218,121; Eppstein et al., 1985, *Proc. Natl. Acad. Sci. U.S.A.,* 82:3688-3692; Hwang et al., 1980, *Proc. Natl. Acad. Sci. U.S.A.,* 77:4030-4034; EP 52,322; EP 36,676; EP 88,046; EP 143,949; EP 142,641;

U.S. Pat. Nos. 4,485,045 and 4,544,545; and EP 102,324. Ordinarily the liposomes are of the small (about 200-800 Angstroms) unilamellar type in which the lipid content is greater than about 30 mole percent cholesterol, the selected proportion being adjusted for the most efficacious therapy.

An "effective amount" of HGF or HGF-containing composition and/or FGF or FGF-containing composition to be employed therapeutically will depend, for example, upon the therapeutic objectives, the route of administration, and the condition of the subject. Accordingly, it may be necessary for the therapist to titer the dosage and modify the route of administration as required to obtain the optimal therapeutic effect. Typically, the clinician will administer the HGF and/or FGF until a dosage is reached that achieves the desired effect. The progress of this therapy is easily monitored by conventional assays and methods.

In the treatment and prevention of eye diseases and disorder such as corneal haze or scarring as well as NK, the pharmaceutical composition comprising HGF and/or FGF can be formulated, dosed, and administered in a fashion consistent with good medical practice. Factors for consideration in this context include the particular mammal being treated, the clinical condition of the individual subject, the cause of the disorder, the method of administration, the scheduling of administration, and other factors known to medical practitioners. The "therapeutically effective amount" of HGF and/or FGF to be administered can be governed by such considerations and is the minimum amount necessary to prevent, ameliorate, or treat the symptoms of the eye disease. Such an amount is preferably below the amount that is toxic or renders significant adverse effects to the host.

As a general proposition, the pharmaceutical composition administered topically to the eye of a subject comprises HGF and/or FGF at an initial concentration in the range of about 0.01% to about 1.0%, about 0.05% to about 0.5%, about 0.05% to about 0.4%, about 0.05% to about 0.3%, or about 0.08% to about 0.25%, on a weight-to-volume (w/v) basis. In some embodiments, the pharmaceutical composition administered topically to the eye of a subject comprises HGF at a concentration of about 0.1% (w/v). In some embodiments, the pharmaceutical composition administered topically to the eye of a subject comprises HGF at a concentration of about 0.2% (w/v). In some embodiments, the pharmaceutical composition administered topically to the eye of a subject comprises FGF at a concentration of about 0.1% (w/v). In some embodiments, the pharmaceutical composition administered topically to the eye of a subject comprises FGF at a concentration of about 0.2% (w/v). In some embodiments, the pharmaceutical composition administered topically to the eye of a subject comprises both HGF and FGF, each at a concentration of about 0.1% (w/v). In some embodiments, the pharmaceutical composition administered topically to the eye of a subject comprises both HGF and FGF, each at a concentration of about 0.2% (w/v). In some embodiments, the pharmaceutical composition comprises HGF and is substantially free of FGF. In some embodiments, the pharmaceutical composition comprises FGF and is substantially free of HGF.

This disclosure also features combination therapy. For example, the subject (e.g., human) is administered HGF described herein in combination with a second therapeutic agent. In some embodiments, the subject is administered an HGF polypeptide concomitantly with a second therapeutic agent. As used herein, the term "concomitant" means "occurring during the same time period." In some embodiments, the HGF polypeptide and the second therapeutic agent are formulated in the same formulation. In some embodiments, the HGF polypeptide and the second therapeutic agent are formulated in separate formulations. In some embodiments, the HGF polypeptide and the second therapeutic agent are administered at the same time. In some embodiments, the HGF polypeptide and the second therapeutic agent are administered sequentially. In some embodiments, the HGF polypeptide is administered before the second therapeutic agent is administered. In some embodiments, an HGF polypeptide is administered after the second therapeutic agent is administered. In some embodiments, the HGF polypeptide and the second therapeutic agent are administered 1 to 60 minutes apart, 5 to 30 minutes apart, or 10 to 20 minutes apart. In some embodiments, the HGF polypeptide and the second therapeutic agent are administered 5 minutes apart. In some embodiments, the HGF polypeptide and the second therapeutic agent are administered 10 minutes apart. In some embodiments, the HGF polypeptide and the second therapeutic agent are administered 15 minutes apart. In some embodiments, the HGF polypeptide and the second therapeutic agent are administered 30 minutes apart. In some embodiments, the HGF polypeptide and the second therapeutic agent are administered 1 hour apart. In some embodiments, the FGF polypeptide is the second therapeutic.

In some embodiments, the second therapeutic agent may elicit the same biological and physiological effects as HGF, for example, activation of similar intracellular pathways. In some embodiments, the second therapeutic agent may elicit different biological and physiological effects as HGF. In some embodiments, the second therapeutic agent enhances the biological and physiological effects caused by HGF. In some embodiments, the second therapeutic agent is of the same class of molecules as HGF (i.e. both are polypeptides). In some embodiments, the second therapeutic agent is of a different class of molecules (e.g. a small molecule or a nucleic acid). Non-limiting examples of second therapeutic agents include small molecules, peptides, proteins, antibodies and antigen-binding fragments, nucleic acids, cells and tissue extracts, and amniotic and other bodily fluids. The second therapeutic agents may be obtained via isolation from natural sources, produced synthetically, or by cell culture. As used herein, the term "small molecule" refers to a low molecular weight organic compound of less than 900 daltons. As used herein, the term "peptide" refers to a compound of 2 to about 50 subunit amino acids, amino acid analogs, or peptidomimetics. The subunits can be linked by peptide bonds. As used herein the term "amino acid" refers to either natural and/or unnatural or synthetic amino acids, including glycine and both the D or L optical isomers, and amino acid analogs and peptidomimetics. As used herein, the term "antibody" includes polyclonal antibodies and monoclonal antibodies as well as fragments thereof. Antibodies include, but are not limited to mouse, rat, rabbit, human, or chimeric antibodies and the like. The term "antibody" also includes antibodies of all isotypes. As used herein, "nucleic acids" or "polynucleotides" refer to polymeric forms of nucleotides or analogs thereof, of any length. The polynucleotides can contain deoxyribonucleotides, ribonucleotides, and/or their analogs. Nucleotides can have any three-dimensional structure, and may perform any function, known or unknown. Nucleic acid molecules further include oligonucleotides, such as antisense molecules, probes, primers and the like. Oligonucleotides typically have from about 2 to about 100, 8 to about 30, or 10 to about 28 nucleotides or analogs thereof.

In some embodiments, the second therapeutic agent is an antibiotic. Non-limiting examples of antibiotics include trimethoprim, polymyxin B, azithromycin, gentamicin, besifloxacin, gatifloxacin, moxifloxacin, levofloxacin, ciprofloxacin, ofloxacin and tobramycin. In some embodiments, the second therapeutic agent is a nonsteroidal anti-inflammatory drug (NSAID). Non-limiting examples of NSAIDs include aspirin, salsalate, celecoxib, diclofenac, etodolac, ibuprofen, indomethacin, ketoprofen, ketorolac, nabumetone, naproxen, oxaprozin, piroxicam, sulindac, and tolmetin. In some embodiments, the second therapeutic agent is an ophthalmic steroid. Non-limiting examples of an ophthalmic steroid include dexamethasone ophthalmic (Maxidex®), difluprednate ophthalmic (Durezol®), fluorometholone ophthalmic (Flarex®, FML®, FML Liquifilm®, FML Forte®), Loteprednol etabonate ophthalmic (Alrex®, Lotemax®), prednisolone acetate ophthalmic (Omnipred®, Pred Forte®, Pred Mild®), prednisolone sodium phosphate ophthalmic, and rimexolone ophthalmic (Vexol®). In some embodiments, the second therapeutic agent is a local anesthetic. Non-limiting examples of local anesthetics include prilocaine, epinephrine, lidocaine, bupivacaine, lontocaine, novocain, ropivacaine, procaine, amethocaine, cinchocaine, mepivacaine, and etidocaine. In some embodiments, the second therapeutic agent is a further growth factor. Non-limiting examples of growth factors include epithelial growth factor (EGF), fibroblast growth factor (FGF), insulin-like growth factor (IGF-1), platelet-derived growth factor (PDGF), keratinocyte growth factor (KGF), transforming growth factor (TGF), vascular endothelial growth factors and granulocyte-macrophage colony-stimulating factor (GM-CSF), neurotrophins and nerve growth factor (NGF), tumor necrosis factor-alpha (TNF-α), and interleukins.

Pharmaceutical Composition and Formulations

Maintaining stability of a polypeptide against thermal stress and minimization of the formation of visible particulates and soluble aggregates are important focuses in the development of pharmaceutical composition comprising a polypeptide, particularly a pharmaceutical composition comprising essentially an aqueous solution that requires long-term storage. See the following references where HGF and related proteins are formulated with various stabilizing agents: WO 90/10651WO00/72873 (EP Pat. No. 1180368), JP-A 9-25241 (U.S. Pat. No. 7,173,008), WO 2008/102849 (U.S. Pat. No. 8,461,112), and U.S. Ser. No. 10/213,485. Although the issue with protein aggregation and thermal stability may be circumvented to some extent using such lyophilized HGF formulations as described in the prior art, this necessitates a freeze-drying unit operation in the production of a pharmaceutical composition comprising HGF, which incurs additional manufacturing costs and complexity in the process. Furthermore, a lyophilized HGF formulation requires re-constitution prior to dosing and administration. Thus, stable solutions are advantageous.

In some embodiments of the present invention, the HGF (and/or FGF) is formulated in a liquid pharmaceutical composition. In some embodiments, the pharmaceutical composition is an aqueous pharmaceutical composition. As used herein, an “aqueous pharmaceutical formulation” refers to a water-based liquid. In some embodiments, the aqueous pharmaceutical composition comprises distilled water. In some embodiments, the aqueous pharmaceutical composition comprises deionized water. In some embodiments, the aqueous pharmaceutical composition comprises sterile water. In some embodiments, the aqueous pharmaceutical composition comprises water for injection (WFI). In some embodiments, the liquid pharmaceutical composition is formulated as an eye drop. In some embodiments, the liquid pharmaceutical composition is formulated as a solution. In some embodiments, the liquid pharmaceutical composition is formulated as a suspension. In some embodiments, the HGF is formulated together with a further therapeutic agent in a liquid pharmaceutical composition. In some embodiments, the HGF is formulated together with a further therapeutic agent as an eye drop. In some embodiments, the HGF is formulated together with a further therapeutic agent as a solution.

Pharmaceutical formulations of polypeptides of the invention or derivatives thereof can be prepared for storage by mixing the polypeptide or derivative thereof having the desired degree of purity with optional pharmaceutically acceptable carriers, excipients, tonicity modifiers or stabilizers (see, e.g., *Remington's Pharmaceutical Sciences*, Chapter 43, 14th Ed., Mack Publishing Co, Easton Pa. 18042, USA), in the form of lyophilized cake or aqueous solutions. Acceptable carriers, excipients, tonicity modifiers, or stabilizers are nontoxic to recipients at the dosages and concentrations employed, and include buffers such as phosphate, citrate, succinate and other organic acids, wherein the term “buffer” refers to a mixture of a weak acid and its conjugate base, or vice versa, that is used to maintain the pH of a solution at a nearly constant value; antioxidants including ascorbic acid; low molecular weight (less than about 10 residues) polypeptides; proteins, such as serum albumin, gelatin, or immunoglobulins; hydrophilic polymers such as polyvinylpyrrolidone (PVP) and polyethylene glycol (PEG); amino acids such as glycine, glutamine, asparagine, arginine, histidine, proline or lysine; monosaccharides, disaccharides, and other carbohydrates including glucose, mannose, sucrose, trehalose or dextrins; chelating agents such as EDTA; sugar alcohols such as mannitol or sorbitol; salt-forming counterions such as sodium or potassium; and/or nonionic surfactants or co-solvents such as polysorbates and poloxamers; tonicity modifiers such as sodium chloride, potassium chloride, mannitol, dextrose, glycerin and magnesium chloride.

In some embodiments, the formulations of the invention are substantially free of a tonicity modifier. In some embodiments, the formulations of the invention are substantially free of chloride salts, such as sodium chloride, potassium chloride, and magnesium chloride.

In some embodiments, the pH of the pharmaceutical formulation comprising HGF (and/or FGF) is about 5.5 to about 7.5. In some embodiments, the pH of the pharmaceutical formulation is about 5.5 to about 6.0. In some embodiments, the pH of the pharmaceutical formulation is about 5.8 to about 6.2. In some embodiments, the pH of the pharmaceutical formulation is about 6.0 to about 6.5. In some embodiments, the pH of the pharmaceutical formulation is about 6.5 to about 7.0. In some embodiments, the pH of the pharmaceutical formulation is about 7.0 to about 7.5. In some embodiments, the pH of the pharmaceutical formulation is about 6.0. In some embodiments, the pH of the pharmaceutical formulation is about 6.5. In some embodiments, the pH of the pharmaceutical formulation is about 7.0.

In some embodiments, the pharmaceutical formulations of the invention further comprise a buffer. In some embodiments, the buffer is selected from acetate, citrate, glutamate, histidine, succinate, tartrate and Tris(hydroxymethyl)aminomethane (Tris). In some embodiments, the buffer is a citrate buffer such as sodium citrate (e.g., sodium citrate dihydrate). In some embodiments, the buffer is an acetate buffer. In some embodiments, the buffer is a succinate buffer. In some embodiments, the buffer is a tartrate buffer. In some embodiments, the buffer is a glutamate buffer. In some embodiments, the buffer is Tris. In some embodiments, the buffer is present at about 10 mM to about 100 mM. In some embodiments, the buffer is present at about 20 mM to about 50 mM. In some embodiments, the buffer is present at about 20 mM.

In some embodiments, the pharmaceutical formulations of the invention further optionally comprise a tonicity modifier. In some embodiments, the pharmaceutical formulation is substantially free of a tonicity modifier. In some embodiments, the tonicity modifier is an alkali metal salt such as sodium chloride (NaCl) or potassium chloride (KCl). In some embodiments, the tonicity modifier is calcium chloride ($CaCl_2$). In some embodiments, the tonicity modifier is mannitol. In some embodiments, the tonicity modifier is trehalose (e.g., trehalose dihydrate). In some embodiments, the tonicity modifier is present at about 0.1 to about 1.0 M, about 0.2 to about 0.8 M, about 0.3 M, about 0.4 M, about 0.5 M, about 0.6 M, about 0.7 M, or about 0.75 M. In some embodiments, the osmolality of the formulation is about 200 to about 500 mOsm/kg $H_2O$, about 200 to about 300 mOsm/kg $H_2O$, about 250 to about 350 mOsm/kg $H_2O$, about 350 to about 400 mOsm/kg $H_2O$, about 400 to about 450 mOsm/kg $H_2O$, or about 450 mOsm/kg $H_2O$ to about 500 mOsm/kg $H_2O$. In some embodiments, the osmolality of the formulation is about 300 mOsm/kg $H_2O$. In some embodiments, the osmolality of the formulation is about 350 mOsm/kg $H_2O$. In some embodiments, the osmolality of the formulation is about 400 mOsm/kg $H_2O$. In some embodiments, the osmolality of the formulation is about 425 mOsm/kg $H_2O$. In some embodiments, the osmolality of the formulation is about 450 mOsm/kg $H_2O$. In some embodiments, the osmolality of the formulation is about 475 mOsm/kg $H_2O$. In some embodiments, the osmolality of the formulation is about 500 mOsm/kg $H_2O$.

In some embodiments, the pharmaceutical formulations of the invention further comprise one or more stabilizers. In some embodiments, the one or more stabilizers are selected from sorbitol, trehalose, sucrose, alanine, glycine, proline, glutamic acid, and arginine. In some embodiments, the one or more stabilizers are selected from sorbital, proline and trehalose. In some embodiments, the one or more stabilizers are selected from proline, arginine, and trehalose. In some embodiments, the one or more stabilizers are selected from glutamic acid, proline, and trehalose. In some embodiments, the one or more stabilizers are selected from arginine, glutamic acid, and trehalose. In some embodiments, the one or more stabilizers are selected from arginine, proline and sorbitol. In some embodiments, the one or more stabilizers are selected from glutamic acid, proline, and sorbitol. In some embodiments, the one or more stabilizers are selected from arginine, glutamic acid, and sorbitol. In some embodiments, the one or more stabilizers are arginine and trehalose. In some embodiments, the one or more stabilizers are sorbital and trehalose. In some embodiments, the one or more stabilizers are proline and trehalose. In some embodiments, the one or more stabilizers are arginine and sorbitol. In some embodiments, the one or more stabilizers are glutamic acid and sorbitol. In some embodiments, the one or more stabilizers are proline and sorbitol. In some embodiments, the stabilizer is trehalose. In some embodiments, the stabilizer is proline. In some embodiments, the stabilizer is arginine. In some embodiments, the stabilizer is sorbitol.

In some embodiments, the pharmaceutical formulations of the invention are substantially free of sucrose, alanine, and glycine. In some embodiments, the pharmaceutical formulation is substantially free of sucrose. In some embodiments, the pharmaceutical formulation is substantially free of alanine. In some embodiments, the pharmaceutical formulation is substantially free of glycine.

In some embodiments, the stabilizer is present in the formulation at a concentration of about 100 mM to about 500 mM. In some embodiments, the stabilizer is present at a concentration of about 150 mM to about 250 mM. In some embodiments, the stabilizer is present at a concentration of about 200 mM.

In some embodiments, the pharmaceutical formulations of the invention further optionally comprise a surfactant. In some embodiments, the surfactant is selected from polysorbate 80 (PS80), polysorbate 20 (PS20), Polaxamer 188 (P188), and Polaxamer 407 (P407). In some embodiments, the surfactant is polysorbate 80. In some embodiments, the surfactant is present at about 0.02% to about 0.07% (w/v). In some embodiments, the surfactant is present at about 0.04% to about 0.06% (w/v). In some embodiments, the surfactant is present at about 0.05% (w/v).

In some embodiments, the pharmaceutical composition of the invention comprises:

(i) about 0.1% (w/v) to about 1.0% (w/v) HGF;
(ii) a buffer that can maintain the pH of the composition at about 5.8 to about 6.2;
(iii) about 100 to about 300 mM of trehalose, proline, sorbitol, or a mixture thereof;
(iv) optionally a tonicity modifier that can provide the osmolality of the composition of about 250 mOsm/kg $H_2O$ to about 500 mOsm/kg $H_2O$; and
(v) optionally a surfactant.

In some embodiments, the pharmaceutical composition of the invention comprises:

(i) about 0.1% to about 0.5% (w/v) HGF;
(ii) a buffer that can maintain the pH of the composition at about 5.8 to about 6.2;
(iii) about 100 to about 300 mM of trehalose, proline, sorbitol, or a mixture thereof;
(iv) optionally a tonicity modifier that can provide the osmolality of the composition of about 250 mOsm/kg $H_2O$ to about 500 mOsm/kg $H_2O$; and
(v) optionally a surfactant.

In some embodiments, the pharmaceutical composition of the invention comprises:

(i) about 0.1% (w/v) HGF;
(ii) a buffer that can maintain the pH of the composition at about 5.8 to about 6.2;
(iii) about 100 to about 300 mM of trehalose, proline, sorbitol, or a mixture thereof;
(iv) optionally a tonicity modifier that can provide the osmolality of the composition of about 250 mOsm/kg $H_2O$ to about 500 mOsm/kg $H_2O$; and
(v) optionally a surfactant.

In some embodiments, the pharmaceutical composition of the invention comprises:

(i) about 0.2% (w/v) HGF;
(ii) a buffer that can maintain the pH of the composition at about 5.8 to about 6.2;
(iii) about 100 to about 300 mM of trehalose, proline, sorbitol, or a mixture thereof;
(iv) optionally a tonicity modifier that can provide the osmolality of the composition of about 250 mOsm/kg $H_2O$ to about 500 mOsm/kg $H_2O$; and
(v) optionally a surfactant.

In some embodiments, the pharmaceutical composition of the invention comprises:

about 0.1% (w/v) HGF;
about 20 mM sodium citrate;
about 200 mM of trehalose, proline, or sorbitol;
about 0.05% (w/v) surfactant;
wherein the pH of the composition is about 6.0.

In some embodiments, the pharmaceutical composition of the invention comprises:
about 0.1% (w/v) HGF;
about 20 mM sodium citrate;
about 200 mM of trehalose;
about 0.05% (w/v) of polysorbate 80 (PS80);
wherein the pH of the composition is about 6.0.

In some embodiments, the pharmaceutical composition of the invention comprises:
about 0.1% (w/v) HGF;
about 20 mM sodium citrate;
about 200 mM of proline;
about 0.05% (w/v) of polysorbate 80 (PS80);
wherein the pH of the composition is about 6.0.

In some embodiments, the pharmaceutical composition of the invention comprises:
about 0.1% (w/v) HGF;
about 20 mM sodium citrate;
about 200 mM of sorbitol;
about 0.05% (w/v) of polysorbate 80 (PS80);
wherein the pH of the composition is about 6.0.

In some embodiments, the pharmaceutical composition of the invention comprises:
about 0.2% (w/v) HGF;
about 20 mM sodium citrate;
about 200 mM of trehalose, proline, or sorbitol;
about 0.05% (w/v) surfactant;
wherein the pH of the composition is about 6.0.

In some embodiments, the pharmaceutical composition of the invention comprises:
about 0.2% (w/v) HGF;
about 20 mM sodium citrate;
about 200 mM of trehalose;
about 0.05% (w/v) of polysorbate 80 (PS80);
wherein the pH of the composition is about 6.0.

In some embodiments, the pharmaceutical composition of the invention comprises:
about 0.2% (w/v) HGF;
about 20 mM sodium citrate;
about 200 mM of proline;
about 0.05% (w/v) of polysorbate 80 (PS80);
wherein the pH of the composition is about 6.0.

In some embodiments, the pharmaceutical composition of the invention comprises:
about 0.2% (w/v) HGF;
about 20 mM sodium citrate;
about 200 mM of sorbitol;
about 0.05% (w/v) of polysorbate 80 (PS80);
wherein the pH of the composition is about 6.0.

In some embodiments, the pharmaceutical composition of the invention comprises:
about 0.1% (w/v) HGF;
about 20 mM sodium citrate;
about 200 mM of trehalose, proline, or sorbitol;
about 0.05% (w/v) surfactant;
wherein the pH of the composition is about 6.0 and the osmolality of the composition is about 350 mOsm/kg $H_2O$.

In some embodiments, the pharmaceutical composition of the invention comprises: about 0.1% (w/v) HGF;
about 20 mM sodium citrate;
about 200 mM of trehalose;
about 0.05% (w/v) of polysorbate 80 (PS80);
wherein the pH of the composition is about 6.0 and the osmolality of the composition is about 350 mOsm/kg $H_2O$.

In some embodiments, the pharmaceutical composition of the invention comprises:
about 0.1% (w/v) HGF;
about 20 mM sodium citrate;
about 200 mM of proline;
about 0.05% (w/v) of polysorbate 80 (PS80);
wherein the pH of the composition is about 6.0 and the osmolality of the composition is about 350 mOsm/kg $H_2O$.

In some embodiments, the pharmaceutical composition of the invention comprises:
about 0.1% (w/v) HGF;
about 20 mM sodium citrate;
about 200 mM of sorbitol;
about 0.05% (w/v) of polysorbate 80 (PS80);
wherein the pH of the composition is about 6.0 and the osmolality of the composition is about 350 mOsm/kg $H_2O$.

In some embodiments, the pharmaceutical composition of the invention comprises:
about 0.2% (w/v) HGF;
about 20 mM sodium citrate;
about 200 mM of trehalose, proline, or sorbitol;
about 0.05% (w/v) surfactant;
wherein the pH of the composition is about 6.0 and the osmolality of the composition is about 450 mOsm/kg $H_2O$.

In some embodiments, the pharmaceutical composition of the invention comprises:
about 0.2% (w/v) HGF;
about 20 mM sodium citrate;
about 200 mM of trehalose;
about 0.05% (w/v) of polysorbate 80 (PS80);
wherein the pH of the composition is about 6.0 and the osmolality of the composition is about 450 mOsm/kg $H_2O$.

In some embodiments, the pharmaceutical composition of the invention comprises:
about 0.2% (w/v) HGF;
about 20 mM sodium citrate;
about 200 mM of proline;
about 0.05% (w/v) of polysorbate 80 (PS80);
wherein the pH of the composition is about 6.0 and the osmolality of the composition is about 450 mOsm/kg $H_2O$.

In some embodiments, the pharmaceutical composition of the invention comprises:
about 0.2% (w/v) HGF;
about 20 mM sodium citrate;
about 200 mM of sorbitol;
about 0.05% (w/v) of polysorbate 80 (PS80);
wherein the pH of the composition is about 6.0 and the osmolality of the composition is about 450 mOsm/kg $H_2O$.

In some embodiments, the HGF is administered in combination with a corneal stroma permeating excipient. Stroma permeating excipients are compounds that can enhance the delivery of therapeutic agents across the corneal layers, primarily the epithelia (Moiseev et al., 2019, *Pharmaceutics,*

11:321-354). These compounds, when included in a pharmaceutical composition and administered topically to the eye, are capable of modifying the tear film, mucus layer or ocular membranes, thereby increasing corneal permeability of the therapeutic agent. Non-limiting examples of stroma permeating excipients include cyclodextrins (CD) including α-, β- and γ-CD; chelating agents such as ethylenediamine-N,N,N',N'-tetraacetic acid (EDTA), ethylene glycol-bis (beta-aminoethyl)-N,N,N',N'-tetraacetic acid (EGTA), 1,2-bis(o-aminophenoxy)ethane-N,N,N',N'-tetraacetic acid (BAPTA) and ethylenediamine-N,N,N',N'-disuccinic acid (EDDS); crown ethers, surfactants, bile acids and bile salts, and cell-penetrating peptides. HGF for in vivo administration are preferably sterile. This can be readily accomplished by filtration of an aqueous solution of HGF through sterile filtration membranes. HGF or variants thereof ordinarily will be stored in lyophilized form or in solution.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

EXAMPLES

Example 1: Amino Acid Sequences of Human HGF Isoforms Available on UniProtKB (uniprot.org/uniprot/P14210)

Amino acid sequence of *Homo sapiens* HGF Isoform 3; (Identifier: P14210-3, Accession number NP_001010932.1) (dHGF)

SEQ ID NO: 1

```
MWVTKLLPALLLQHVLLHLLLLPIAIPYAEGQRKRRNTIHEFKKSAKTTLIKIDPALKIK

TKKVNTADQCANRCTRNKGLPFTCKAFVFDKARKQCLWFPFNSMSSGVKKEFGHEFDLYE

NKDYIRNCIIGKGRSYKGTVSITKSGIKCQPWSSMIPHEHSYRGKDLQENYCRNPRGEEG

GPWCFTSNPEVRYEVCDIPQCSEVECMTCNGESYRGLMDHTESGKICQRWDHQTPHRHKF

LPERYPDKGFDDNYCRNPDGQPRPWCYTLDPHTRWEYCAIKTCADNTMNDTDVPLETTEC

IQGQGEGYRGTVNTIWNGIPCQRWDSQYPHEHDMTPENFKCKDLRENYCRNPDGSESPWC

FTTDPNIRVGYCSQIPNCDMSHGQDCYRGNGKNYMGNLSQTRSGLTCSMWDKNMEDLHRH

IFWEPDASKLNENYCRNPDDDAHGPWCYTGNPLIPWDYCPISRCEGDTTPTIVNLDHPVI

SCAKTKQLRVVNGIPTRTNIGWMVSLRYRNKHICGGSLIKESWVLTARQCFPSRDLKDYE

AWLGIHDVHGRGDEKCKQVLNVSQLVYGPEGSDLVLMKLARPAVLDDFVSTIDLPNYGCT

IPEKTSCSVYGWGYTGLINYDGLLRVAHLYIMGNEKCSQHHRGKVTLNESEICAGAEKIG

SGPCEGDYGGPLVCEQHKMRMVLGVIVPGRGCAIPNRPGIFVRVAYYAKWIHKIILTYKV

PQS.
```

Amino acid sequence of *Homo sapiens* HGF Isoform 1; (Identifier: P14210-1, Accession number: NP_000592.3)

SEQ ID NO: 2

```
MWVTKLLPALLLQHVLLHLLLLPIAIPYAEGQRKRRNTIHEFKKSAKTTLIKIDPALKIK

TKKVNTADQCANRCTRNKGLPFTCKAFVFDKARKQCLWFPFNSMSSGVKKEFGHEFDLYE

NKDYIRNCIIGKGRSYKGTVSITKSGIKCQPWSSMIPHEHSFLPSSYRGKDLQENYCRNP

RGEEGGPWCFTSNPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.
```

-continued

Amino acid sequence of *Homo sapiens* HGF Isoform 2
(Identifier: P14210-2, Accession Number: NP_001010931.1):

SEQ ID NO: 3

MWVTKLLPALLLQHVLLHLLLLPIAIPYAEGQRKRRNTIHEFKKSAKTTLIKIDPALKIK

TKKVNTADQCANRCTRNKGLPFTCKAFVFDKARKQCLWFPFNSMSSGVKKEFGHEFDLYE

NKDYIRNCIIGKGRSYKGTVSITKSGIKCQPWSSMIPHEHSFLPSSYRGKDLQENYCRNP

RGEEGGPWCFTSNPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCET.

Amino acid sequence of *Homo sapiens* HGF Isoform 4
(Identifier: P14210-4):

SEQ ID NO: 4

MWVTKLLPALLLQHVLLHLLLLPIAIPYAEGQRKRRNTIHEFKKSAKTTLIKIDPALKIK

TKKVNTADQCANRCTRNKGLPFTCKAFVFDKARKQCLWFPFNSMSSGVKKEFGHEFDLYE

NKDYIRNCIIGKGRSYKGTVSITKSGIKCQPWSSMIPHEHSFLPSSYRGKDLQENYCRNP

RGEEGGPWCFTSNPEVRYEVCDIPQCSEVECMTCNGESYRGLMDHTESGKICQRWDHQTP

HRHKFLPERYPDKGFDDNYCRNPDGQPRPWCYTLDPHTRWEYCAIKNMRDITWALN.

Amino acid sequence of *Homo sapiens* HGF Isoform 5
(Identifier: P14210-5, NP_001010933.1):

SEQ ID NO: 5

MWVTKLLPALLLQHVLLHLLLLPIAIPYAEGQRKRRNTIHEFKKSAKTTLIKIDPALKIK

TKKVNTADQCANRCTRNKGLPFTCKAFVFDKARKQCLWFPFNSMSSGVKKEFGHEFDLYE

NKDYIRNCIIGKGRSYKGTVSITKSGIKCQPWSSMIPHEHSYRGKDLQENYCRNPRGEEG

GPWCFTSNPEVRYEVCDIPQCSEVECMTCNGESYRGLMDHTESGKICQRWDHQTPHRHKF

LPERYPDKGFDDNYCRNPDGQPRPWCYTLDPHTRWEYCAIKTCET.

Amino acid sequence of *Homo sapiens* HGF Isoform 6
(Identifier: P14210-6, NP_001010934.1):

SEQ ID NO: 6

MWVTKLLPALLLQHVLLHLLLLPIAIPYAEGQRKRRNTIHEFKKSAKTTLIKIDPALKIK

TKKVNTADQCANRCTRNKGLPFTCKAFVFDKARKQCLWFPFNSMSSGVKKEFGHEFDLYE

NKDYIRNCIIGKGRSYKGTVSITKSGIKCQPWSSMIPHEHSFLPSSYRGKDLQENYCRNP

RGEEGGPWCFTSNPEVRYEVCDIPQCSEGK.

HGF Variant:

SEQ ID NO: 7

MWVTKLLPALLLQHVLLHLLLLPIAIPYAEGQRKRRNTIHEFKKSAKTTLIKIDPALEIK

TKKANTADQCANRCTRSKGLPFTCKAFVFDKARKRCLWFPFNSMSSGVKKEFGHEFDLYE

NKDYIRDCIIGKGRSYRGTVSITKSGIKCQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

-continued

HGF Variant:

SEQ ID NO: 8

MWVTKLLPALLLQHVLLHLLLLPIAIPYAEGQRKRRNTIHEFKKSAKTTLIKIDPALKIK

TEKANTADQCANRCIRNKGLPFTCKAFVFDKARKRCLWFPVNSMSSGVKKEFGHEFDLYE

NKDYTRNCIVGNGRSYRGTVSTTKSGIKCQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 9

MWVTKLLPALLLQHVLLHLLLLPIAIPYAEGQRKRRNTIHEFKKSAKTTLIKIDPALKIK

TEKANTADQCANRCTRSKGLPETCKAFVFDKARKRCLWFPFNSMSSGVKKEFGHEFDLYE

NKDYIRDCIVGNGRSYRGTVSITKSGIECQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 10

MWVTKLLPALLLQHVLLHLLLLPIAIPYAKGQGKRRNTIHEFKKSAKTTLIKIDPALKIK

TEKADTADQCANRCTRSKGLPFTCKAFVFDKARKQCLWFPFNSMSSGVKKEFGHEFDLYE

NKDYIRDCIVGNGRSYRGTVSVTKSGIKCQPWSSMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

-continued

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 11

MWVTKLLPALLLQHVLLHLLLLPIAIPYAEGQRKRRNAIHEFKKSAKATLIKIDPALKIK

TEKANTADQCANRCTRSKGLPFTCKAFVFDKARKRCLWFPFNSMSSGVKKEFGHEFDLYE

NKDYIRDCIVGNGRSYRGTVSITKSGIECQPWSSMIPHEHSFLPSSYRGEDLQENYCRNP

WGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 12

MWVTKLLPALLLQHVLLHLLLLPIAIPYAEGQRKRRNTIHEFKKSAKTTLIKIDPALKIK

TEKANTADQCANRCTRSKGLPFTCKAFVFDKARKRCLWFPFNSMSSGVKKEFGHEFDLYE

NKDYTRNCIVGNGRSYRGTVSITKSGIECQPWSAMIPHEHSFLPSSYQGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 13

MWVTKLLPALLLQHVLLHLLLLPIAIPYAEGQRKRRNTIHEFKKSAKTTLIKIDPALKIK

TKKVNTADQCANRCTRNKGLPFTCKAFVFDKARKQCLWFPFNSMSSGVKKEFGHEFDLYE

NKDYIRNCIIGKGRSYKGTVSITKSGIKCQPWSSMIPHEHSFLPSSYRGKDLQENYCRNP

RGEEGGPWCFTSNPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

-continued

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 14

MWVTKLLPALLLQHVLLHLLLLPIAIPYAEGQRKRRDAIHECKRSAKTTLIKIDPALKIK

TEKANTADQCANRCTRNKGLPSTCKAFVFDKARKRRLRFPFNSMSSGVKKEFGHEFDLYE

NKDYTRNCIVGKGRSYRGTVSTTKSGIKCQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 15

MWVTKLLPALLLQHVLLHLLLLPIAIPYAEGQGKRRNTIHEFKKSAKTTLIKIDPALKIK

TEKVNTADQCANRCTRSKGLPFTCKAFVFDKARKRCLWFPFNSMSSGVKKEFGHEFDLYE

NKDYIRDCIIGRGRSYRGTVSITKSGIKCQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 16

MWVTKLLPALLLQHVLLHLLLLPIAIPHAEGQRKRRNTIHEFKKSAKTTLIKIDPALKIK

TEKANTADQCANRCTRSKGLPFTCKAFVFDKARKRCLWFPFNSMSSGVKKEFGHEFDLYE

NKDYTRNCIVGNGRSYRGTVSTTKSGIKCQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

-continued

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 17

MWVTKLLPALLLQHVLLHLLLLPIAIPYAEGQRKRRNTIHEFKKSAKTTLIKIDPALKIK

TEKANTADQCANRCTRSRGLPFTCKAFVFDKARKQCLWFPFNSMSSGVKKEFGHEFDLYE

NKDYIRDCIIGNGRSYRGTVSVTKSGIKCQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 18

MWVTKLLPALLLQHVLLHLLLLPIAIPYAEGQRKRRNTIHEFKKSAKTTLIKIDPALKIK

TEKANTADQCANRCTRNKGLPFTCKAFVFDKARKRCLWFPFNSMSSGVKKEFGHEFDLYE

NKDYIRDCIVGNGRSYRGTVSITKSGIKCQPWSSMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 19

MWVTKLLPALLLQHVLLHLLLLPIAIPYAEGQRKRRNTIHEFKKSVKTTLIKIDPALKIK

TEKANTADQCANRCTRSKGLPFTCKAFVFDKARKRCLWFPVNSMSSGVKKESGHEFDLYE

NKDYIRDCIVGNGRSYRGTVSTTKSGIKCQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

-continued

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 20

MWVTKLLPALLLQHVLLHLLLLPIAIPYAEGQRKRRNTIHEFKKSAKTTLIKIDPALKIK

TEKANTADQCANRCTRSKGLPFTCKAFVFDKARKRCLWFPFNSMSSGVKKEFGHEFDLYE

NKDYIRDCIVGNGRSYRGTVSITKSGIKCQPWSSMIPHEHSFLPSSYRGEDLRENYCRNP

WGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 21

MWVTKLLPALLLQHVLLHLLLLPIAIPYAEGQRKRRNTIHEFKKSAKTTLIKIDPALRIK

TEKANTADQCANRCTRSRGLPFTCKAFVFDKARKRCLWFPFNSMSSGVKKEFGHEFDLYE

NKDYIRDCIIGNGRSYRGTVSITKSGIKCQPWSSMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 22

MWVTKLLPALLLQHVLLHLLLLPIAIPYAEGQRKRRNTIHEFKKSAKTTLIKIDPALKIK

TEKANTADQCANRCTRSRRLPFTCKAFVFDKARKRCLWFPFNSMSSGVKKEFGHEFDLYE

NKDYIRDCIIGKGRSYRGTVSVTKSGIECQPWSAMIPHEHSFLPSNYRGEDLRENYCRNP

-continued

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 23

MWVTKLLPALLLQHVLLHLLLLPIAIPYAEGQRKRRNTIHEFKKSAKTTLIKIDPALKIK

TEKANTADQCANRCTRSKGLPFTCKAFVFDKARKRCLWFPFNSMSSGVKKEFGHEFDLYE

NKDYIRDCIVGNGRSYRGTVSITKSGIECQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 24

MWVTKLLPALLLQHVLLHLLLLPIAIPYAEGQRKRRNTIHEFKKSAKTTLIKIDPALKIK

TKKVDTADQCANRCTRNKGLPETCKAFVFDKARKRCLWFPFNSMSSGVKKEFGHEFDLYE

NKDYIRDCIIGNGRSYRGTVSITKSGIKCQPWSSMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 25

MWVTKLLPALLLQHVLLHLLLLPIAIPYAEGQGKRRNTIHEFKKSAKTTLIKIDPALRIK

TEKANTADQCANRCTRSKGLPFTCKAFVFDKARKRCLWFPFNSMSSGVKKEFGHEFDLYE

-continued

NKAYIRDCIIGRGRNYRGTVSITKSGIKCQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 26

MWVTKLLPALLLQHVLLHLLLLPIAIPYAKGQRKRRNTIHEFKKSAKTTLIKIDPALEIK

TEKVNTADQCANRCIRNKGLPFTCKAFVFDKARKRCLWFPFNSMSSGVKKEFGHEFDLYE

NKAYIRDCIIGRGRNYRGTVSITKSGIKCQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

HGF Variant:

SEQ ID NO: 27

MWVTKLLPALLLQHVLLHLLLLPIAIPYAEGQGKRRNTIHEFKKSAKTTLIKIDPALKIK

TEKVNTADQCANRCTRSKGLPFTCKAFVFDKARKRCLWFPFNSMSSGVKKEFGHEFDLYE

NKDYIRDCIIGNGRSYRGTVSITKSGIKCQPWSAMIPHEHSFLPSSYRGEDLRENYCRNP

RGEEGGPWCYTSDPEVRYEVCDIPQCSEVECMTCNGESYRGLMDHTESGKICQRWDHQTP

HRHKFLPERYPDKGFDDNYCRNPDGQPRPWCYTLDPHTRWEYCAIKTCADNTMNDTDVPL

ETTECIQGQGEGYRGTVNTIWNGIPCQRWDSQYPHEHDMTPENFKCKDLRENYCRNPDGS

ESPWCFTTDPNIRVGYCSQIPNCDMSHGQDCYRGNGKNYMGNLSQTRSGLTCSMWDKNME

DLHRHIFWEPDASKLNENYCRNPDDDAHGPWCYTGNPLIPWDYCPISRCEGDTTPTIVNL

DHPVISCAKTKQLRVVNGIPTRTNIGWMVSLRYRNKHICGGSLIKESWVLTARQCFPSRD

LKDYEAWLGIHDVHGRGDEKCKQVLNVSQLVYGPEGSDLVLMKLARPAVLDDFVSTIDLP

-continued

NYGCTIPEKTSCSVYGWGYTGLINYDGLLRVAHLYIMGNEKCSQHHRGKVTLNESEICAG

AEKIGSGPCEGDYGGPLVCEQHKMRMVLGVIVPGRGCAIPNRPGIFVRVAYYAKWIHKII

LTYKVPQS.

FGF1 Wild-Type:

SEQ ID NO: 28

FNLPPGNYKKPKLLYCSNGGHFLRILPDGTVDGTRDRSDQHIQLQLSAESVGEVYIKSTE

TGQYLAMDTDGLLYGSQTPNEECLFLERLEENHYNTYISKKHAEKNWFVGLKKNGSCKRG

PRTHYGQKAILFLPLPVSSD.

FGF1 Variant:

SEQ ID NO: 29

FNLPPGNYKKPKLLYCSNGGHFLRILPNGTVDGTRDRSDQHIQLQLSAESVGEVYIKSTE

TGQYLAMDTDGLLYGSQTPNEECLFLERLEENHYNTYISKKHAEKNWEVGLKKNGSCKRG

PRTHYGQKAIRFLPLPVSSD.

FGF1 Variant:

SEQ ID NO: 30

FNLPPGNYKKPKLLYCSNGGHFLRILPDGTVDGTRDRSDPHIQLQLIAESVGEVYIKSTE

TGQYLAMDTDGLLYGSQTPNEECLFLERLEENGYNTYISKKHAEKNWFVGLKKNGSCKRG

PRTHYGQKAILFLPLPVSSD.

FGF1 Variant:

SEQ ID NO: 31

FNLPPGNYKKPKLLYCSNGGHFLRILPNGTVDGTRDRSDPHIQLQLIAESVGEVYIKSTE

TGQYLAMDTDGLLYGSQTPNEECLFLERLEENGYNTYISKKHAEKNWFVGLKKNGSCKRG

PRTHYGQKAIRFLPLPVSSD.

FGF1 Variant:

SEQ ID NO: 32

FNLPPGNYKKPKLLYCSNGGHFLRILPDGTVDGTRDRSDQHIQLQLSAESVGEVYIKSTE

TGQYLAMDTDGLLYGSQTPNEECLFLERLEENHYNTYISKKHAEKNWFVGLKKNGSCKRG

PRTHYGQKAIRFLPLPVSSD.

FGF1 Variant:

SEQ ID NO: 33

FNLPPGNYKKPKLLYCSNGGHFLRILPDGTVDGTRDRSDQHIQLQLSAESVGEVYIKSTE

TGQYLAMDTDGLLYGSQTPNEECLFLERLEENHYNTYISKKHAEKNWFVGLKKNGSCKRG

PRTHYGQKAIRFLPLPVSSD.

Signal Peptide of SEQ ID NO: 1

SEQ ID NO: 34

MWVTKLLPALLLQHVLLHLLLLPIAIPYAEG

Un-cleaved Alpha and Beta chain peptide
of SEQ ID NO: 1

SEQ ID NO: 35

QRKRRNTIHEFKKSAKTTLIKIDPALKIKTKKVNTADQCANRCTRNKGLPFTCKAFVFDK

ARKQCLWFPFNSMSSGVKKEFGHEFDLYENKDYIRNCIIGKGRSYKGTVSITKSGIKCQP

WSSMIPHEHSYRGKDLQENYCRNPRGEEGGPWCFTSNPEVRYEVCDIPQCSEVECMTCNG

ESYRGLMDHTESGKICQRWDHQTPHRHKFLPERYPDKGFDDNYCRNPDGQPRPWCYTLDP

HTRWEYCAIKTCADNTMNDTDVPLETTECIQGQGEGYRGTVNTIWNGIPCQRWDSQYPHE

HDMTPENFKCKDLRENYCRNPDGSESPWCFTTDPNIRVGYCSQIPNCDMSHGQDCYRGNG

KNYMGNLSQTRSGLTCSMWDKNMEDLHRHIFWEPDASKLNENYCRNPDDDAHGPWCYTGN

PLIPWDYCPISRCEGDTTPTIVNLDHPVISCAKTKQLRVVNGIPTRTNIGWMVSLRYRNK

HICGGSLIKESWVLTARQCFPSRDLKDYEAWLGIHDVHGRGDEKCKQVLNVSQLVYGPEG

SDLVLMKLARPAVLDDFVSTIDLPNYGCTIPEKTSCSVYGWGYTGLINYDGLLRVAHLYI

-continued

```
MGNEKCSQHHRGKVTLNESEICAGAEKIGSGPCEGDYGGPLVCEQHKMRMVLGVIVPGRG

CAIPNRPGIFVRVAYYAKWIHKIILTYKVPQS

Alpha chain peptide of SEQ ID NO: 1
                                                     SEQ ID NO: 36
QRKRRNTIHEFKKSAKTTLIKIDPALKIKTKKVNTADQCANRCTRNKGLPFTCKAFVFDK

ARKQCLWFPFNSMSSGVKKEFGHEFDLYENKDYIRNCIIGKGRSYKGTVSITKSGIKCQP

WSSMIPHEHSYRGKDLQENYCRNPRGEEGGPWCFTSNPEVRYEVCDIPQCSEVECMTCNG

ESYRGLMDHTESGKICQRWDHQTPHRHKFLPERYPDKGFDDNYCRNPDGQPRPWCYTLDP

HTRWEYCAIKTCADNTMNDTDVPLETTECIQGQGEGYRGTVNTIWNGIPCQRWDSQYPHE

HDMTPENFKCKDLRENYCRNPDGSESPWCFTTDPNIRVGYCSQIPNCDMSHGQDCYRGNG

KNYMGNLSQTRSGLTCSMWDKNMEDLHRHIFWEPDASKLNENYCRNPDDDAHGPWCYTGN

PLIPWDYCPISRCEGDTTPTIVNLDHPVISCAKTKQLR

Beta chain peptide of SEQ ID NO: 1
                                                     SEQ ID NO: 37
VVNGIPTRTNIGWMVSLRYRNKHICGGSLIKESWVLTARQCFPSRDLKDYEAWLGIHDVH

GRGDEKCKQVLNVSQLVYGPEGSDLVLMKLARPAVLDDFVSTIDLPNYGCTIPEKTSCSV

YGWGYTGLINYDGLLRVAHLYIMGNEKCSQHHRGKVTLNESEICAGAEKIGSGPCEGDYG

GPLVCEQHKMRMVLGVIVPGRGCAIPNRPGIFVRVAYYAKWIHKIILTYKVPQS
```

Example 2: Formulations

A design-of-experiments (DoE) study was performed to identify optimal pH, buffer and stabilizers that can prevent the aggregation and maintain best physicochemical stability of HGF in a solution formulation. The HGF protein (activated dHGF from SEQ. ID NO. 1) was formulated at 34.67 mg/mL in 10 mM citrate, 1M NaCl, 0.075% PS80, pH 6.0 and buffer-exchanged into formulations listed in Table 3 using Amicon-15 concentrator units (10 kDa MWCO) to a concentration of 1 mg/mL. A volume of 340 μL of the 34.67 mg/mL solution was added to pre-rinsed concentrators (with appropriate buffer), and diluted to 15 mL in the appropriate formulation buffer solution (without surfactant). Samples were centrifuged at 3200 rcf until a volume of ~5 mL is achieved, then diluted again to ~15 mL total volume with the appropriate formulation buffer. This buffer-exchange process was repeated for five cycles with a total dilution of ~3610-fold. The sample volume was reduced to ~7 mL in the final centrifugation cycle. Assuming a worst-case recovery of ~60%, the final protein concentration of each sample was ~1 mg/mL, with an estimated residual concentration of PS80 to be ~0.004%.

The buffer-exchanged samples were analyzed for protein content by UV-Visible spectroscopy using an extinction coefficient 1.890 mL $mg^{-1}$ $cm^{-1}$. Samples were normalized to target 1 mg/mL using appropriate formulation buffer as needed and spiked with 10% PS80 (w/v, prepared from USP grade PS80, cat #4117-04 J. T. Baker or equivalent) to a target concentration of 0.05% PS80 in the HGF formulations. The theoretical residual PS80 level at the end of the buffer exchange process (~0.004%) were not taken into account as the residual level of PS80 was minimal relative to the amount of spiked PS80.

Following normalization of the protein content and surfactant concentrations, the formulations were sterile-filtered using 0.22 μm sterile concentrators (Millipore Ultrafree-CL GV, P/N UFC40GV0S). Each formulation was sterile-filtered into six sterilized type 1 borosilicate glass vials (2 mL, 13 mm, Cat #RTF8418, Afton) at 1.0 mL per vial. The remaining sample volume was transferred to 1 mL LDPE tubes (Cat #03-439-61W Fisher) and used as initial time-point control (TO) for analytical testing. For center point formulations, 200 μL from TO testing vial was transferred to 1 mL LDPE tubes (Cat #03-439-61W Fisher) and used for adsorption study as described below. Sample transfer and sterile filtration procedures were performed in a sterilized biosafety cabinet using aseptic techniques. Vials were stoppered with sterilized Fluorotec stoppers, and capped with 13FO aluminum caps with buttons. Two vials of each formulation type were stored at the following storage conditions: 2-8° C. for 4 weeks and 40° C. for 4 weeks. Sample appearance was evaluated for color, clarity, and particulates by visual inspection. Thermal stability of the protein was evaluated by DSF/SLS. In addition, turbidity measurements were carried out using UV-Visible Spectroscopy by measuring absorption at 340 nm wavelength. Conformational stability and aggregation stability of the protein were determined by DLS and SEC-HPLC, respectively. Samples were further analyzed using reducing and non-reducing capillary gel electrophoresis (CE-SDS) and isoelectric focusing (icIEF) gel electrophoresis. The presence of particulate matters was assessed using an HIAC particle counter in which, average particle counts of >2 μm, ≥5 μm, ≥10 μm, and ≥25 μm in a sample were reported.

All DoE analyses were performed in randomized order. The data from TO and stability time points for all DoE formulations were evaluated using Design Expert Stat Ease® software to derive statistically significant trends.

Adsorption Study to Evaluate Non-Specific HGF Protein Absorption to LDPE Container Surfaces Samples in LDPE tubes were stored at 2-8° C. for at least five days. The protein content as determined by UV absorbance at 280 nm (A280) was measured for these sample after five days of storage and the values were compared to the corresponding results at TO to determine if there was any adsorption of protein to the LDPE container material. Minimal protein adsorption was observed when stored in the LDPE container, where the % difference in the HGF concentrations measured after 5 days is less than 4% for the majority of formulations tested, with the exception of the formulation that includes sucrose and alanine, where an 8% drop in HGF protein concentration was observed (Table 3). Results from this study supports the use of LDPE tubes as a viable container for the HGF formulations.

TABLE 3

LDPE Adsorption Study

| Formulation | pH | Concentration (mg/mL) T = initial | Concentration (mg/mL) T = 5 days | % Difference |
|---|---|---|---|---|
| 20 mM Citrate, 200 mM Sorbitol, | 6.0 | 1.0 | 1.0 | 1 |
| 0.05% PS80 | 6.0 | 1.0 | 1.0 | 2 |
| 20 mM Citrate, 200 mM Proline, | 6.0 | 1.0 | 1.0 | 3 |
| 0.05% PS80 | 6.0 | 1.0 | 1.0 | 2 |
| 20 mM Citrate, 200 mM Trehalose, | 6.0 | 1.0 | 1.0 | 3 |
| 0.05% PS80 | 6.0 | 1.0 | 1.0 | 1 |
| 30 mM Acetate, 200 mM Sorbitol, | 5.0 | 1.0 | 1.0 | 4 |
| 0.05% PS80 | 5.0 | 1.0 | 1.0 | 3 |
| 30 mM Acetate, 200 mM Proline, | 5.0 | 1.0 | 1.0 | 1 |
| 0.05% PS80 | 5.0 | 1.0 | 1.0 | 1 |
| 30 mM Acetate, 200 mM Trehalose, | 5.0 | 1.0 | 1.0 | 2 |
| 0.05% PS80** | 5.0 | 1.0 | 1.0 | 1 |
| 10 mM Citrate, 0.3M NaCl, 1% sucrose, 0.5% Alanine, 0.05% PS80** | 6.0 | 1.1 | 1.0 | 8 |
| 10 mM Citrate, 0.75M NaCl, 0.08% glycine, 0.01% PS80** | 6.0 | 1.0 | 1.0 | 2 |

Results

In general, lower turbidity was observed in formulations at the higher pH range of 6.0-6.5 upon storage at 40° C. or 5° C. for 1 month (Table 4). Formulations comprising 200 mM trehalose showed low turbidity (below 0.01) across the pH range of 5.0-6.5, wherein the formulation comprising 200 mM trehalose at pH 6.0 showed the lowest turbidity upon storage at 40° C. for 1 month.

TABLE 4

Turbidity of various HGF solution formulations stored at 40° C. or 5° C. for 1 month.

| Formulation | pH | A340* 1 M @ 40° C. | A340* 1 M @ 5° C. |
|---|---|---|---|
| 20 mM Citrate, 200 mM Sorbitol, 0.05% PS80 | 5.5 | 0.011 | 0.005 |
| | 6.0 | 0.016 | 0.008 |
| | 6.5 | 0.024 | 0.013 |
| 20 mM Citrate, 200 mM Proline, 0.05% PS80 | 5.5 | 0.028 | 0.023 |
| | 6.0 | 0.009 | 0.006 |
| | 6.5 | 0.030 | 0.014 |
| 20 mM Citrate, 200 mM Trehalose, 0.05% PS80 | 5.5 | 0.009 | 0.007 |
| | 6.0 | 0.007 | 0.005 |
| | 6.5 | 0.014 | 0.009 |
| 30 mM Acetate, 200 mM Sorbitol, 0.05% PS80 | 4.5 | 0.027 | 0.009 |
| | 5.0 | 0.015 | 0.013 |
| | 5.5 | 0.019 | 0.021 |
| 30 mM Acetate, 200 mM Proline, 0.05% PS80 | 4.5 | 0.023 | 0.021 |
| | 5.0 | 0.019 | 0.008 |
| | 5.5 | 0.011 | 0.018 |
| 30 mM Acetate, 200 mM Trehalose, 0.05% PS80 | 4.5 | 0.032 | 0.014 |
| | 5.0 | 0.022 | 0.010 |
| | 5.5 | 0.010 | 0.009 |
| 10 mM Citrate, 0.3M NaCl, 1% sucrose, 0.5% Alanine, 0.05% PS80** | 6.0 | 0.017 | 0.014 |
| 10 mM Citrate, 0.75M NaCl, 0.08% glycine, 0.01% PS80** | 6.0 | 0.006 | 0.000 |

*All A340 values are reported as average of measurements from two independent preparations, except formulations denoted with **, which denotes single preparation.

Presence of particulate matters upon storage at 5° C. or 40° C. for 1 month, as detected using HIAC, was observed with several of the formulations (Table 5). Formulations comprising 200 mM sorbitol, 200 mM proline or 200 mM trehalose at pH 5.0, or 200 mM trehalose or 0.08% glycine at pH 6.0 showed the lowest particulate counts. However, other analytical data, including the turbidity data shown in Table 4, point to better overall stability for the HGF protein at pH 6.0, wherein only the 200 mM trehalose and 0.08% glycine formulations showed low particulate counts upon storage.

TABLE 5

Particulate counts as measured by HIAC for HGF formulations stored at 40° C. or 5° C. for 1 month.

| | | HIAC Particulate Counts* T1 M @ 40° C. | | | | HIAC Particulate Counts* T1 M @ 5° C. | | | |
|---|---|---|---|---|---|---|---|---|---|
| Formulation | pH | ≥2 μm | ≥5 μm | ≥10 μm | ≥25 μm | ≥2 μm | ≥5 μm | ≥10 μm | ≥25 μm |
| 20 mM Citrate, 200 mM Sorbitol, 0.05% PS80 | 6.0 | 326 | 121 | 46 | 4 | 386 | 146 | 48 | 3 |
| 20 mM Citrate, 200 mM Proline, 0.05% PS80 | 6.0 | 753 | 238 | 94 | 4 | 417 | 125 | 20 | 0 |
| 20 mM Citrate, 200 mM Trehalose, 0.05% PS80 | 6.0 | 142 | 47 | 16 | 2 | 200 | 73 | 19 | 0 |
| 20 mM Citrate, 200 mM Sorbitol, 0.05% PS80 | 5.0 | 125 | 34 | 3 | 0 | 327 | 81 | 13 | 0 |
| 20 mM Citrate, 200 mM Proline, 0.05% PS80 | 5.0 | 74 | 24 | 7 | 2 | 433 | 140 | 26 | 1 |
| 20 mM Citrate, 200 mM Trehalose, 0.05% PS80 | 5.0 | 132 | 33 | 6 | 2 | 314 | 113 | 50 | 8 |
| 10 mM Citrate, 0.3M NaCl, 1% sucrose, 0.5% Alanine, 0.05% PS80** | 6.0 | 955 | 100 | 43 | 2 | 172 | 57 | 23 | 3 |
| 10 mM Citrate, 0.75M NaCl, 0.08% glycine, 0.01% PS80** | 6.0 | 57 | 5 | 0 | 0 | 47 | 13 | 8 | 0 |

*All HIAC values are reported as average of measurements from two independent preparations, except formulations denoted with **, which denotes single preparation Reducing capillary gel electrophoresis (R-CE-SDS) was used to further assess the chemical stability of the HGF protein in different formulations. HGF is a heterodimer comprising the α and β chains, which are linked via a disulfide bond. Under reducing conditions, two peaks are present in the electropherogram (% main peak 1 and % main peak 2 in Table 6); the column labeled with "% other" represents potential degradation products of the HGF protein. As shown in Table 6, HGF formulations at pH 6.0 generally showed better chemical stability during long-term storage, both at 40° C. and 5° C., wherein the highest % total main peak was observed with formulations comprising 200 mM trehalose or 200 mM proline at pH 6.0. HGF formulation comprising 0.08% glycine, which showed good stability in terms of particulate counts and turbidity, turned out to have poor chemical stability as revealed by R-CE-SDS.

TABLE 6

Reducing capillary gel electrophoresis (R-CE-SDS) for HGF formulations stored at 40° C. or 5° C. for 1 month.

| | | T1 M @ 40° C. | | | | T1 M @ 5° C. | | | |
|---|---|---|---|---|---|---|---|---|---|
| Formulation | pH | % Main Peak 1 | % Main Peak 2 | % Other | % Total Main* | % Main Peak 1 | % Main Peak 2 | % Other | % Total Main* |
| 20 mM Citrate, 200 mM Sorbitol, 0.05% PS80 | 6.0 | 31.5 | 45.9 | 22.5 | 77.5 | 31.4 | 46.5 | 22.1 | 77.9 |
| 20 mM Citrate, 200 mM Proline, 0.05% PS80 | 6.0 | 31.9 | 47.1 | 21.0 | 79.0 | 31.8 | 46.9 | 21.3 | 78.7 |
| 20 mM Citrate, 200 mM Trehalose, 0.05% PS80 | 6.0 | 32.0 | 47.0 | 20.9 | 79.1 | 31.3 | 46.8 | 21.9 | 78.1 |

TABLE 6-continued

Reducing capillary gel electrophoresis (R-CE-SDS) for HGF formulations stored at 40° C. or 5° C. for 1 month.

| | | T1 M @ 40° C. | | | | T1 M @ 5° C. | | | |
|---|---|---|---|---|---|---|---|---|---|
| Formulation | pH | % Main Peak 1 | % Main Peak 2 | % Other | % Total Main* | % Main Peak 1 | % Main Peak 2 | % Other | % Total Main* |
| 20 mM Citrate, 200 mM Sorbitol, 0.05% PS80 | 5.0 | 34.2 | 41.0 | 24.8 | 75.2 | 32.0 | 47.5 | 20.5 | 79.5 |
| 20 mM Citrate, 200 mM Proline, 0.05% PS80 | 5.0 | 34.3 | 41.2 | 24.6 | 75.4 | 31.4 | 47.7 | 20.9 | 79.1 |
| 20 mM Citrate, 200 mM Trehalose, 0.05% PS80 | 5.0 | 34.6 | 41.9 | 23.5 | 76.5 | 31.9 | 47.7 | 20.3 | 79.7 |
| 10 mM Citrate, 0.3M NaCl, 1% sucrose, 0.5% Alanine, 0.05% PS80** | 6.0 | 30.8 | 44.5 | 24.6 | 75.4 | 30.1 | 43.0 | 27.0 | 73.0 |
| 10 mM Citrate, 0.75M NaCl, 0.08% glycine, 0.01% PS80** | 6.0 | 29.8 | 37.9 | 32.3 | 67.7 | 26.9 | 39.1 | 34.0 | 66.0 |

*All % peak values are average of measurements from two independent preparations, except formulations denoted with **, which denotes single preparation.

Example 3: Bioassay to Determine Relative Potency

Formulations that showed the best overall attributes as identified in the formulation development experiments described under Example 2 were further assessed for relative potency using a cell proliferation promotion activity potency assay with Mv.1.Lu cells (American mink lung cell line), in the presence of transforming growth factor beta (TGF-β). TGF-β inhibits cell growth in Mv.1.Lu cells, and the HGF formulations described herein can reverse this growth inhibition. Mv.1.Lu cells were thawed, and viability of the cell stock was assessed by trypan blue staining. Following the determination of viable cell density, an appropriate number of cells were transferred to a flask for initial culture. The cells were continuously grown and expanded in tissue culture flasks prior to plating for sample analysis.

Each reference standard and each test sample was diluted with assay medium to generate an eight-point dilution curve. The potency of each test sample was determined by comparison of the dilution curve generated by the test sample against the reference standard.

Cultured cells from tissue culture flasks were trypsinized and resuspended in assay medium (containing 250 pg/mL TGF-ß) to approximately 0.1×106 cells/mL. Fifty microliters of cell suspension were plated in each well of a 96-well plate. The 96-well plates containing the cultured cells were incubated at 37° C./5% $CO_2$ for 1 to 4 hours prior to the addition of reference standard and test samples. Test samples and reference standards were added to separate wells in triplicate, and the cells were incubated for 72 hours.

After the incubation, MTS proliferation reagent (Promega, Cat. No G3582) or equivalent was added to each well, and the 96-well plate was incubated at 37° C./5% $CO_2$ for 4 hours. Following this incubation, the plate was placed in a UV-Vis plate reader and the absorbance was measured at 490 nm. Each reference standard and test sample was analyzed in triplicate and the potency was determined by parallel line assessment. Each sample was compared to the reference standard by a four-parameter constrained fit to determine relative potency.

Test Sample (TS) Acceptance Criteria:

1. The TS independent four parameter curve fit must exhibit a dose dependent relationship when plotting the mean response vs. log protein concentration.
2. The $R^2$ value for the TS independent 4-parameter fit must be ≥0.97.
3. All % CV values for the TS must be ≤20%.
4. Potency of the system suitability sample will be determined using the global fit model and the F-probability of each TS must be ≥0.01
5. Test samples which do not pass all of the above criteria will be retested under the same conditions.
6. Assay plates which do not pass any of the above criteria must be retested under the same conditions once.
7. The % RP of the Standard Sample (SS) must be within 50%-200%.

Results from the in vitro relative potency bioassay for select formulations are summarized in Table 7. HGF solution formulations comprising 200 mM trehalose at pH 6.0, was confirmed to also maintain excellent potency for the HGF protein (99%).

TABLE 7

Relative Potency of HGF in Different Formulations

| Formulation | Results (% Relative Potency)** |
|---|---|
| 20 mM Citrate, 200 mM Proline, pH 6.0 | 106% |
| 20 mM Citrate, 200 mM Trehalose, pH 6.0 | 99% |
| 20 mM Citrate, 200 mM Sorbitol, pH 6.0 | 93% |
| 30 mM Acetate, 200 mM Proline, pH 4.5 | 34% |
| 30 mM Acetate, 200 mM Trehalose, pH 4.5 | 35% |
| 30 mM Acetate, 200 mM Sorbitol, pH 4.5 | 29% |
| 30 mM Acetate, 200 mM Proline, pH 5.5 | 68% |

TABLE 7-continued

Relative Potency of HGF in Different Formulations

| Formulation | Results (% Relative Potency)** |
|---|---|
| 30 mM Acetate, 200 mM Trehalose, pH 5.5 | 63% |
| 30 mM Acetate, 200 mM Sorbitol, pH 5.5 | 70% |
| 10 mM Citrate, 0.75M NaCl, 0.08% glycine, 0.01% PS80, pH 6.0 | 91% |
| 10 mM Citrate, 0.3M NaCl, 1% sucrose, 0.5% Alanine, 0.05% PS80, pH 6.0 | 98% |

**Relative potency as compared to reference standard.

Example 4: Efficacy of Topical Formulations in a Mouse Corneal Mechanical Injury Model The effectiveness of topical formulations of HGF for use in the treatment of NK was tested in a mouse corneal injury model. The efficacy test was carried in two phases using male C57BL/6 mice. In Phase I, one eye per each of 75 animals were dosed 4 times per day (QID) with 2 hours between doses on Day 0 (injury) and 3 hours between doses for the remainder of the study (Day 8) using a 3.5 μL volume of test article via a pipette. Animals (~10-20%) that did not respond to the injury (i.e., no corneal haze/opacity at Day 3) were excluded from the study. The Phase 1 study experimental design is summarized in Table 8 below.

TABLE 8

Experimental Design for Phase 1 Efficacy Test of HGF in the Treatment of NK in a Mouse Corneal Mechanical Injury Model

| Group # | # of Animals* | Treatment (QID on Day 0) | Endpoints/Procedures | Euthanasia |
|---|---|---|---|---|
| 1 | 12 + 3 | PBS | Baseline ocular examination (Slit-lamp) Bright field digital photography post-operatively and then daily up to 7 days. Fluorescein staining and imaging post-operatively and then daily up to 7 days. OCT (Pre-& post injury baseline, Days 3 and 7) N = 3/group were sacrificed after 3 days of treatment for histopathology (H & E staining of whole eye ball cross section) | Day 8 (Animals from PBS group were used for a Trial run as described in Table 9 below) |
| 2 | 12 + 3 | 0.1% (w/v) dHGF (T1)** | | |
| 3 | 12 + 3 | 0.2% (w/v) dHGF (T2)** | | |
| 4 | 12 + 3 | 0.1% (w/v) mNGF(N) | | |
| 5 | 12 + 3 | 0.1% (w/v) mHGF (HGF) | | |

Abbreviations:

mNGF: murine nerve growth factor mHGF: murine hepatocyte growth factor

*The following animals were excluded on Day 3:

1. Animals (n = 1-2/group) that did not respond to injury (i.e., no corneal haze/opacity on Day 3) were excluded on Day 3 by the Sponsor, and the Sponsor was masked.

2. Animals (n = 3/group) as representatives of each group were collected for histology (H & E staining).

**T1: 0.1% (w/v) human dHGF (SEQ ID NO: 1) in PBS.

T2: 0.2% (w/v) human dHGF (SEQ ID NO: 1) in PBS.

TABLE 9

Trial run to determine frequency of epithelial scraping (Animals (n = 9-10) from PBS group of Phase 1 were used for this pilot), and 0.1% vs. 0.2% dHGF dose were selected based on Phase 1 outcome.

| Group # | # of Animals* | Treatment (QID) starting on Day 10 | Endpoints/Procedures | Euthanasia |
|---|---|---|---|---|
| 1 | 3 | HGF(0.1%) (+once epi. scraping) | One time on Day 10 prior to start of treatment, scrape corneal epithelium using Algerbrush on the opaque area (1 mm trephine). Bright-field pics and OCT at baseline (Day 10, Day 14, Day 17, Day 20 | Day 20 |
| 2 | 4 | HGF(0.1%) (+three epi. scraping) | One time on each Day 10, Day 14 and Day 17 prior to treatment, scrape epithelium using Algerbrush on the opaque area (1 mm trephine). Bright-field pics and OCT at baseline (Day 10), Day 14, Day 17, Day 20 | Day 20 |

In Phase 2 of the efficacy study, 85 animals were dosed on the injured cornea 4 times per day (QID) with 2 hours between doses on Day 11 (injury) and 3 hours between doses for the remainder of the study (Day 20) in a 3.5 μL volume of test article. At the time of first treatment application (Day 11), the corneal epithelium was removed by gently applying the tip of the Algerbrush on the opaque area (marked with 1 mm trephine) of the cornea. The corneal epithelium was removed a second time on Day 16. The study design for Phase 2 is summarized in Table 10 below.

TABLE 10

Experimental Design for Phase 2 Efficacy Test of HGF in the Treatment of NK in a Mouse Corneal Mechanical Injury Model

| Group # | # of Animals* | Treatment (QID) starting on Day 10 | Endpoints/Procedures | Euthanasia |
|---|---|---|---|---|
| 1 | 17 | Vehicle** | Baseline ocular examination (Slit-lamp) | Day 21 |
| 2 | 17 | 0.1% (w/v) dHGF | Bright-field Digital photography on | |
| 3 | 17 | 0.2% (w/v) dHGF | baseline (Day 8), Days 16 and 21. | |
| 4 | 17 | 0.1% (w/v) mNGF | Fluorescein Staining and Imaging on | |
| 5 | 17 | 0.1% (w/v) mHGF | baseline (Day 8) Day 21. | |
| | | | OCT baseline (Day 8), Days 16 and 21. | |

*Animals with the correct phenotype were enrolled for treatment.
Abbreviations:
mNGF: murine nerve growth factor
mHGF: murine hepatocyte growth factor
dHGF: human hepatocyte growth factor (SEQ. ID NO. 1)
**vehicle = PBS; mNGF, mHGF and dHGF were formulated in vehicle at the specified concentration.

Corneal Injury (Phase 1 and Phase 2):

Prior to model induction, the test subjects were given buprenorphine at 0.01-0.05 mg/kg subcutaneously. Animals were also given a cocktail of tropicamide (1.0%) and phenylephrine (2.5%) topically to dilate and proptose the eyes. The animals were then tranquilized for the surgical procedure with a ketamine/xylazine cocktail, and one drop of 0.5% proparacaine HCl. Forceps (e.g. Dumont #4) were used to proptose the animal's eye, and with mild pressure, a 2 mm trephine was placed over the central cornea. The trephine was rotated 3 clock hours with gentle pressure to define the defect area. An Algerbrush II (Alger Company Inc., Lago Vista, TX), with a 0.5 mm burr was used to remove the corneal epithelium and anterior stroma within the trephined area. The injured stroma was marked by the appearance of stromal debris. Stromal debris was removed by washing with balanced salt saline (BSS). The animals were scanned by Optical Coherence Tomography (OCT) and fluorescein-stained prior to the application of the first dose of treatment to the injured eye. Topical antibiotics (Ofloxacin) was applied after 15 minutes and the animals were allowed to recover normally from surgery. The animals received a second dose of buprenorphine at 0.01-0.05 mg/kg subcutaneously approximately 6-8 hours post-surgery and twice daily every 6-8 hours for two days post-surgery.

Corneal Injury (Epithelial Removal, Phase 2 Only):

Prior to initiation of Phase 2, a pilot study was performed to determine the optimal number of epithelial scrapings following the initial injury as described above for Phase 1. Two scrapings were sufficient for the desired model induction. Upon initiation of Phase 2, the animals were given buprenorphine at 0.01-0.05 mg/kg subcutaneously. Animals were also given a cocktail of tropicamide (1.0%) and phenylepherine (2.5%) topically to dilate and proptose the eyes. Animals were then tranquilized for the surgical procedure with a ketamine/xylazine cocktail, and one drop of 0.5% proparacaine HCl was applied. On Day 0, the animals underwent the surgical procedure as described above for Phase 1. On Days 11 and 16 following the initial injury and scar formation, forceps (e.g. Dumont #4) were used to proptose the animal's eye, and with mild pressure, a 1 mm trephine was placed over the scar area on the cornea. The trephine was rotated 3 clock hours with gentle pressure to define the defect area. An Algerbrush II (Alger Company Inc., Lago Vista, TX), with a 0.5 mm burr was used to remove the corneal epithelium within the trephined area. The ocular surface was then washed with BSS. The animals were scanned by Optical Coherence Tomography (OCT), fluorescein-stained and photographed, prior to the application of the first dose of treatment to the injured eye. Topical antibiotics (Ofloxacin) were applied after 15 minutes and the animals were allowed to recover normally from surgery. The animals received a second dose of buprenorphine at 0.01-0.05 mg/kg subcutaneously approximately 6-8 hours post-surgery and twice daily (BID) every 6-8 hours for two days post-surgery.

Parameters Monitored:

(i) Examination and Body Weights:

Mortality and morbidity was observed twice daily along with cage-side observations with particular attention paid to both eyes. Due to the significant amount of handling during Phase 1 of this study for dosing and imaging, n=18 animals died (Group 1: 4 mice; Group 2: 3 mice; Group 3: 3 mice; Group 4: 3 mice; Group 5: 5 mice) or were euthanized prior to study end. During the pilot for Phase 2, there were no deaths. In Phase 2, the number of imaging sessions was reduced and only n=3 mice died (Group 1: 1 mouse; Group 2: 1 mouse; Group 4: 1 mouse). Body weights were taken prior to model induction and at time of necropsy.

(ii) Ocular Examinations and Brightfield Images:

Baseline ocular surface morphology was evaluated by a veterinary ophthalmologist under a slit lamp biomicroscope prior to enrollment. Brightfield images were captured for the analysis of corneal opacity using Image J software at baseline and on days as indicated in the study design.

(iii) Fluorescein Stains:

At time points as indicated in the experimental design table, animals underwent fluorescein ocular surface staining. Approximately 1.5 μl of 2.5% sodium fluorescein was applied to the corneal surface for 30 seconds followed by rinsing with 1×PBS using 1 ml syringe. Corneal staining was photographed under cobalt blue light using a Nikon Digital SLR camera mounted on a tripod. The camera lens was placed in manual mode, with the lens setting at 1 foot away.

The animals' eye was focused in the center of the viewing window and images were collected to maintain consistent distance between the camera lens and the animal's eye. Area (in pixels) of fluorescein staining for each eye at each time point was determined using Image J Software (NIH).

(iv) Optical Coherence Tomography (OCT):

On days as indicated by the experimental design table, all animals underwent OCT imaging procedures of the anterior section of the eye. The animals were anesthetized and the corneas were washed with PBS prior to OCT examination.

(v) Histology (Phase 1 Only):

On Day 3, Following the final in-life measurements, a subset of the animals were humanely euthanized by carbon dioxide asphyxiation followed by thoracotomy. The surgical eyes of the animals were collected into 10% neutral buffered formalin. On the following day, the eyes were placed in 70% ethanol, embedded in paraffin wax and cut sagittally. Three slides containing serial sections that include the optic nerve were stained with haemotoxylin and eosin (H&E) for morphology. In addition, blocks remaining after H&E were sectioned further and immunohistochemistry for TUJ-1 staining (also known as beta III tubulin) was performed to evaluate corneal innervation. DAPI (blue) was used as a counterstain to highlight all nuclei. The slides were analyzed by a veterinary ophthalmologist.

(vii) Results:

1) Accelerated Healing (Fluorescein Staining)

Figure 2:
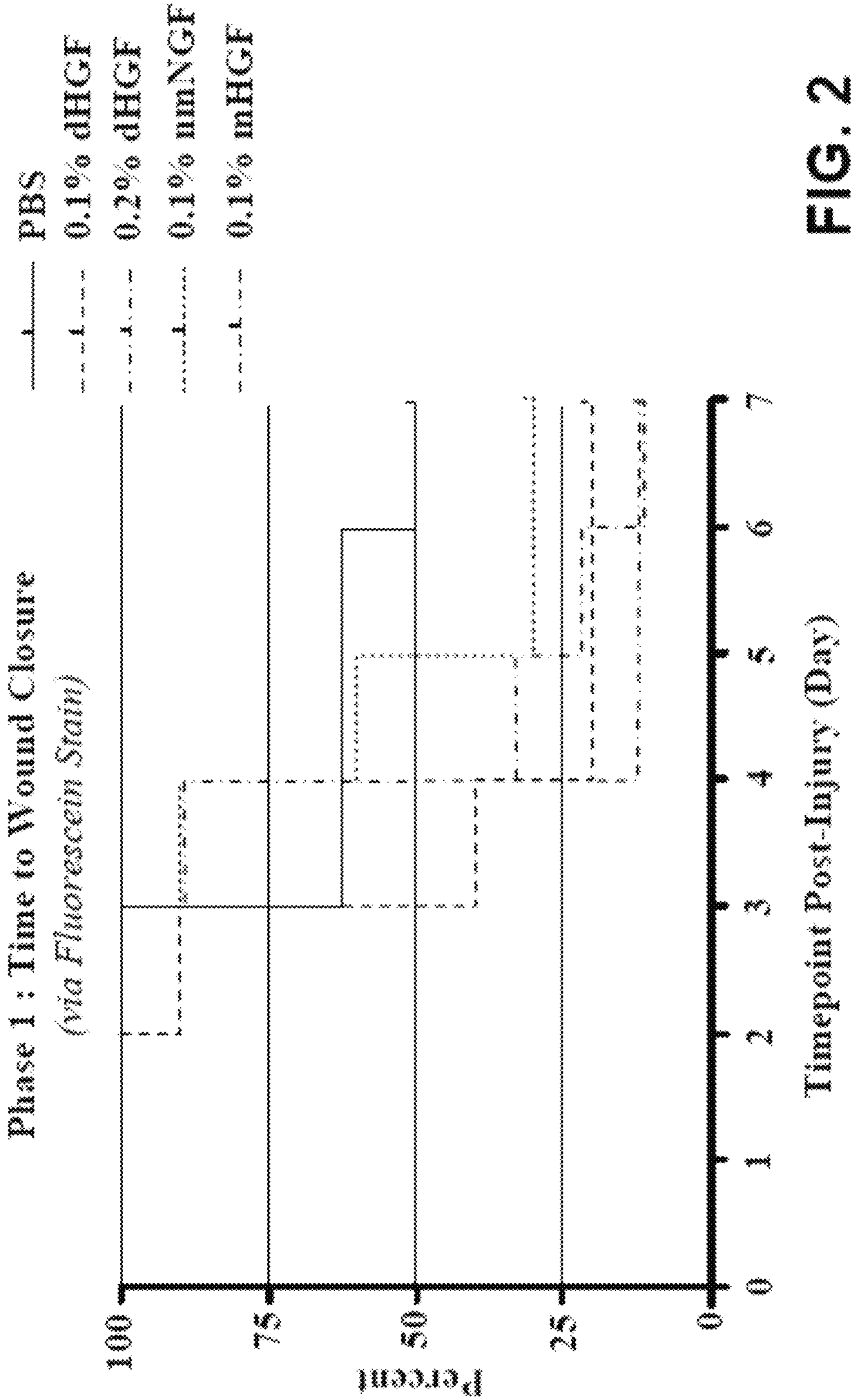
FIG. 2. Time to closure analysis on the fluorescein-stained corneal surface of animals following surgery and daily treatment with PBS (vehicle control), 0.1% or 0.2% dHGF, 0.1% mNGF or 0.1% mHGF in Phase 1 study in the mouse corneal mechanical injury model.

More TUJ01 staining was observed in the Day 3 post-surgery tissue samples from animals treated with 0.1% dHGF compared to those receiving the PBS vehicle (FIG. 1), indicative of corneal innervation on in the animals treated with 0.1% dHGF. The epithelial healing time was faster with 0.1% dHGF (p=0.041) and 0.2% dHGF when compared to the PBS control and 0.1% mNGF (FIG. 2). Time for 50% of the eyes to heal completely was three days in the 0.1% dHGF group, which was half the time it took for the PBS group (six days; p=0.41). Both the 0.2% dHGF and 0.1% mHGF groups healed at a rate that was two-thirds that of the PBS group (four days versus six days). In addition, 0.1% mHGF was significantly faster than mNGF (p=0.053) and PBS (p=0.0018). Animals receiving 0.1% dHGF began closure earlier and >75% had reached closure by Day 4 post treatment; the same effect was seen for 0.1% mHGF (FIG. 2). In comparison, only 50% of PBS-treated animals reached complete wound closure and not until Day 6.

2) Scar Prevention (Brightfield Image Analysis)

Figure 3A:
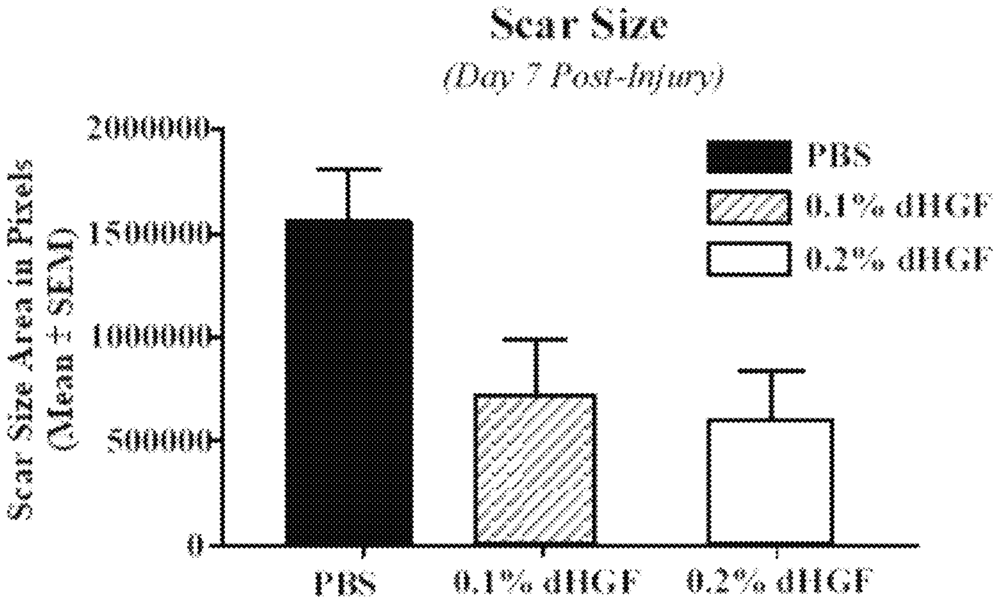
FIG. 3A. Brightfield image analysis of average scar area (in pixels) measured in corneal surface of animals treated with PBS (control), 0.1% dHGF or 0.2% dHGF at Day 7 post surgery in the mouse corneal mechanical injury model.
Figure 3B:
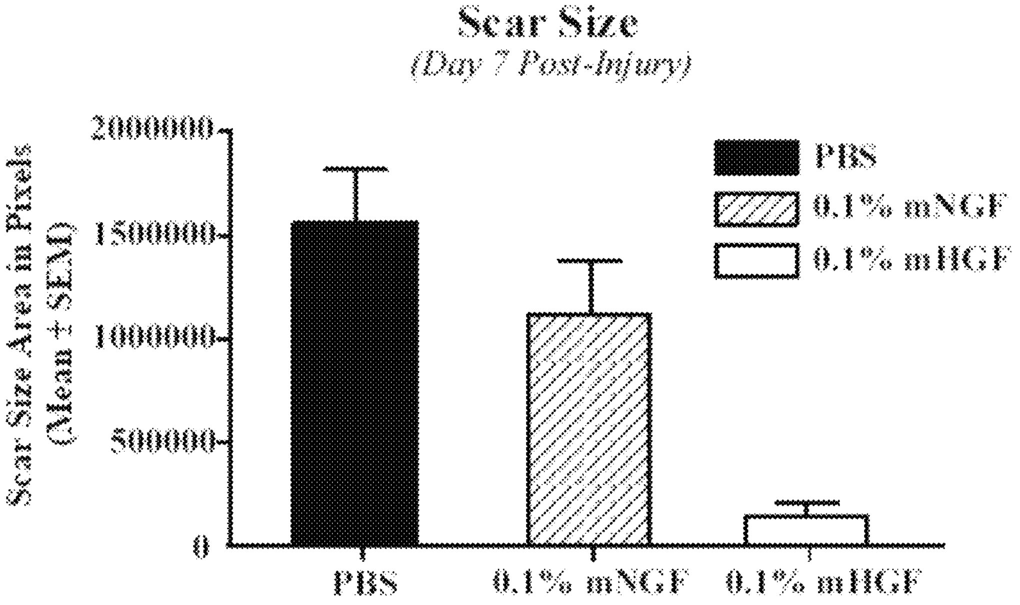
FIG. 3B. Brightfield image analysis of average decrease in scar area (in pixels) measured in corneal surface of animals treated with PBS (control), 0.1% mNGF or 0.1% mHGF at Day 7 post surgery in the mouse corneal mechanical injury model.

Following surgery and daily treatment with PBS (control), 0.1% or 0.2% dHGF, 0.1% mNGF or 0.1% mHGF, all test articles with the exception of the PBS control effectively reduced the average scar size by Day 7 (FIG. 3). Quantification of test article effect on scar formation revealed that the 0.1% mHGF had the largest effect followed by 0.1% dHGF. In the dHGF groups, scars were significantly smaller (p=0.0439 and p=0.0126 for the 0.1% and 0.2% groups, respectively) than the PBS control, but not significantly different from each other (p=0.7406). The mean area of the scars in the 0.1% mHGF group was significantly smaller on Day 7 than control (p=0.0001) and 0.1% mNGF (p=0.0029). The mean size of scars in the control and 0.1% mNGF groups were not significantly different (p=0.2481) from each other.

The effect size driven by HGF is mirrored in the time to closure analysis (see Section vii.1). The reduction in scar formation with 0.1% mHGF was approximately 9-fold greater than that observed in the control group, while the percent reductions with 0.1% and 0.2% dHGF were more than 5-fold greater than control. Percent reduction with 0.1% mNGF was approximately half of that of the dHGF groups, with a numerically, but not statistically significant, greater reduction in scar size than the PBS control group.

3) Scar Reversal (Brightfield Image Analysis)

Figure 4:
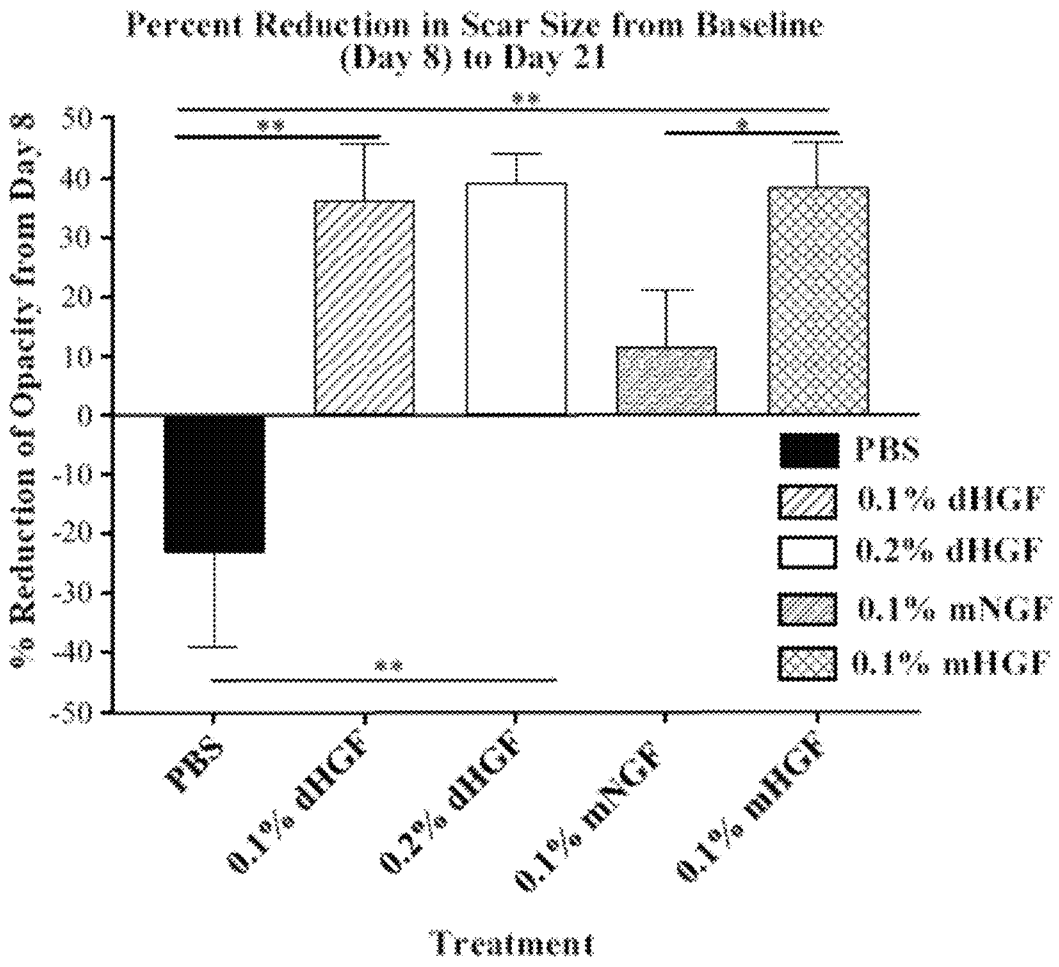
FIG. 4. Mean percent, standard error of measurement (SEM) and statistical comparison of scar reduction from Day 8 to Day 21 for animals treated with PBS (control), dHGF (0.1% and 0.2%), mHGF and mNGF in the mouse corneal mechanical injury model.

Following surgery to remove the corneal epithelium and anterior stroma and two repeat scrapings to remove solely the epithelium, PBS-treated animals had very little change in scar size while animals receiving 0.1% dHGF, 0.2% dHGF or 0.1% mHGF had decreased corneal scar size. In the PBS control group, mean scar size continued to increase by more than 20% from baseline (Day 8) to Day 21. In contrast, scars in the three HGF groups decreased in size by more than 35% from baseline to Day 21, with an overall difference of 55% in mean size compared with the PBS group. The differences between 0.1% dHGF and 0.2% dHGF compared to PBS control were statistically significant (p=0.0054 and p=0.0015, respectively) as shown in FIG. 4. The mean scar size in the 0.1% mNGF group decreased from Day 8 to Day 21, but was not significantly different from PBS control (p=0.0859). The results from treatment using either 0.1% or 0.2% dHGF were not significantly different (p=0.7558).

Based on results from this study, 0.1% dHGF treatment following a single epithelial and anterior stroma removal (Phase 1) or multiple epithelial scrapings (Phase 2) resulted in faster wound closure (Phase 1) and a larger decrease in scar size (Phase 2) when dosed four times per day starting on the date of the first surgical procedure (Phase 1) or on Day 11 (Phase 2)

In Phase 1, all animals underwent a single surgical procedure to remove the corneal epithelium and anterior stroma within a 2 mm area. All animals received dosing four times per day following the procedure. While approximately 50% of PBS-treated animals (vehicle control) healed by Day 7 post-surgery, >75% of animals that received 0.1% dHGF or 0.1% mHGF had healed by Day 7 (FIG. 2 and FIG. 3). Additionally, a larger percentage of the corneas of these animals were fully healed by Day 3 post-surgery when compared to PBS-treated (>60% versus 30%, respectively). Analysis of corneal innervation on Day 3 by immunofluorescence revealed increased TUJ-1 staining in 0.1% dHGF-treated animals (FIG. 1).

In Phase 2, animals underwent the same surgical procedure as in Phase 1 but then received two additional procedures to remove only the epithelium. In this experiment, animals began receiving treatment following the first epithelial scrape. Under these conditions, animals that received HGF (0.1% dHGF, 0.2% dHGF or 0.1% mHGF) showed substantial decreases in scar size compared to PBS-treated eyes, with scar size decreasing by >35% for all HGF-treated eyes (FIG. 4).

The results from this study indicate that topical administration of HGF following corneal epithelial injury led to faster healing rates and reduction in scar sizes in single or multiple injury models.

Example 5: Efficacy of Topical Formulations in a Mouse Corneal Bacterial LPS-Induced Keratitis Model The effectiveness of topical formulations of HGF for use in the treatment of NK was tested in a mouse corneal bacterial LPS-induced keratitis model. The efficacy test was carried out in male C57BL/6 mice. One eye per each of 40 animals were dosed 4 times per day (QID) with 3 hours between doses on Days 4-9 post injury using a 3.5 μL volume of test article via a pipette. The injured eye received test articles or controls as indicated in the experimental design (Table 11). Stock solution of lipopolysaccharide (LPS) from *E. coli O*111:B4 (Invivogen) was diluted with 1 mL of sterile water, aliquoted and stored according to the manufacturer's protocol. On the day of dosing, the diluted LPS solution was further diluted 1:1 (v/v) with PBS to deliver approximately 5 μg of the LPS material in a 2.0 μL injection.

TABLE 11

Experimental Design for Efficacy Test of HGF in the Treatment of NK in a Mouse Corneal Bacterial LPS-Induced Keratitis Injury Model

| Group # | # of Animals* | Treatment (QID) starting on Day 10 | Endpoints/Procedures | Euthanasia |
|---|---|---|---|---|
| 1 | 10 | PBS | Baseline ocular examination (Slit-lamp)* | Day 10 |
| 2 | 10 | 0.1% (w/v) dHGF** | Bright-field Digital photography (Day 0, | |
| 3 | 10 | 0.2% (w/v) dHGF** | n-5 eyes prior to injection), Days 5 to 9 | |
| 4 | 10 | 0.1% (w/v) mNGF** | Fluorescein Staining on Days to 7. | |
| | | | OCT (Day 0, n = 5 eyes prior to injection) | |
| | | | and Day 8. | |

* Baseline ocular examinations were performed on n = 5 mice; all enrolled animals were evaluated on subsequent days.

Abbreviations:

mNGF: murine nerve growth factor dHGF: human hepatocyte growth factor (SEQ. ID NO. 1)

**formulated in PBS at the specified concentration.

Corneal Injury Using LPS from *E. coli O*111:B4

Prior to model induction, the test subjects were given buprenorphine at 0.01-0.05 mg/kg subcutaneously. Animals were also given a cocktail of tropicamide (1.0%) and phenylephrine (2.5%) topically to dilate and proptose the eyes. The animals were then tranquilized for the surgical procedure with a ketamine/xylazine cocktail, and one drop of 0.5% proparacaine HCl. Forceps (e.g. Dumont #4) were used to proptose the animal's eye, and using a 34G needle attached to a 2.5 syringe, approximately 5 μg of LPS (*E. coli O*111:B4) was injected in a 2.0 μL volume. The LPS injections were done on Days 0 and 4. The first dose of treatment was applied to the injured eye after the Day 4 injection of LPS. Topical antibiotics (Ofloxacin) was applied after 15 minutes and the animals were allowed to recover normally from surgery. The animals received a second dose of buprenorphine at 0.01-0.05 mg/kg subcutaneously approximately 6-8 hours post-surgery and twice daily every 6-8 hours for two days post-surgery.

Parameters Monitored (i) Examination and Body Weights:

Mortality and morbidity was observed twice daily along with cage-side observations. Body weights were taken prior to model induction and at time of necropsy.

(ii) Ocular Examination and Brightfield Images:

Ocular surface morphology was evaluated by a veterinary ophthalmologist under a slit lamp biomicroscope prior to enrollment. Brightfield images were captured for the analysis of corneal opacity using Image J software at baseline and on days as indicated in the study design.

(iii) Fluorescein Stains:

At time points as indicated in the experimental design table, animals underwent fluorescein ocular surface staining. Approximately 1.50 of 2.5% sodium fluorescein was applied to the corneal surface for 30 seconds followed by rinsing with 1×PBS using 1 ml syringe. Corneal staining was photographed under cobalt blue light using a Nikon Digital SLR camera mounted on a tripod. The camera lens was placed in manual mode, with the lens setting at 1 foot away. The animals' eye was focused in the center of the viewing window and images were collected to maintain consistent distance between the camera lens and the animal's eye. Area (in pixels) of fluorescein staining for each eye at each time point was determined using Image J Software (NIH).

(iv) Optical Coherence Tomography (OCT):

On days as indicated by the experimental design table, all animals underwent OCT imaging procedures of the anterior section of the eye. The animals were anesthetized and the corneas were washed with PBS prior to OCT examination.

Figure 5:
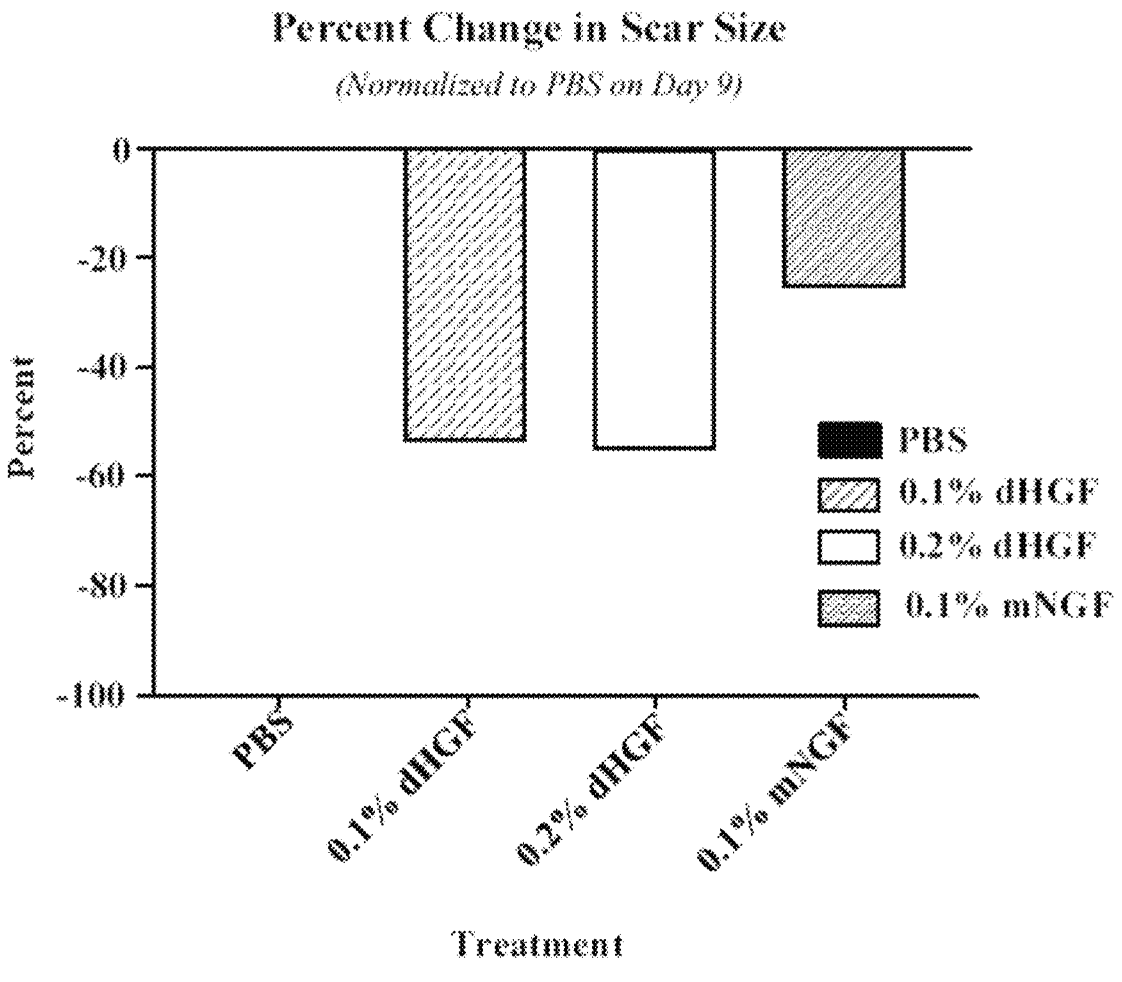
FIG. 5. Percent change of scar size on Day 9 for animals treated with PBS (control), dHGF (0.1% and 0.2%), or mNGF in the mouse corneal *E. coli* LPS-induced keratitis model.

(v) Results:

Following induction of the model and four times per day daily treatment with PBS (control), 0.1% or 0.2% dHGF, or 0.1% mNGF, Groups 2 and 3 (0.1% and 0.2% dHGF, respectively) showed the largest reduction in scar size by Day 9. When normalized to Group 1, Groups 2 and 3 reduced scar size by nearly 60% while the test article in Group 4 reduced scar size by approximately 25% (FIG. 5). Mean scar area was significantly smaller with 0.1% dHGF (p=0.0110) and 0.2% dHGF (p=0.0028) compared to PBS controls. Scars were approximately 5-fold larger with PBS controls compared to 0.1% and 0.2% HGF groups and approximately 2.5-fold larger with PBS than in the 0.1% mNGF group (p=0.0417). The resulting mean scar sizes in the two dHGF groups were not significantly different (p=0.6176) from each other (FIG. 5).

In summary, the results from this study suggest that treatment of the injured eye with HGF following corneal epithelial injury induced by stromal administration of *E. coli* LPS led to improved healing rates.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. An aqueous pharmaceutical composition consisting of:

about 0.1% (w/v) hepatocyte growth factor (HGF);

about 20 mM sodium citrate buffer having a pH of about 6.0;

about 200 mM trehalose, and surfactant.

2. The composition of claim 1, wherein the HGF is activated HGF.

3. The composition of claim 2, wherein the activated HGF is deleted hepatocyte growth factor (dHGF) in activated form.

4. The composition of claim 1, wherein the surfactant is polysorbate 80.

5. The composition of claim 1, wherein the HGF comprises:

(a) a first polypeptide comprising the amino acid sequence having at least 90% identity to amino acids 32-494 of SEQ ID NO: 2; and a second polypeptide comprising the amino acid sequence having at least 90% identity to amino acids 495-728 of SEQ ID NO: 2, optionally wherein the first polypeptide comprises a deletion of the amino acids corresponding to amino acids 161-165 of SEQ ID NO: 2; or (b) a first polypeptide comprising the amino acid sequence having at least 90% identity to amino acids 32-494 of SEQ ID NO: 7; and a second polypeptide comprising the amino acid sequence having at least 90% identity to amino acids 495-728 of SEQ ID NO: 7, optionally wherein the first polypeptide comprises a deletion of the amino acids corresponding to amino acids 161-165 of SEQ ID NO: 7; or (c) a first polypeptide comprising the amino acid sequence having at least 90% identity to amino acids 32-494 of SEQ ID NO: 8; and a second polypeptide comprising the amino acid sequence having at least 90% identity to amino acids 495-728 of SEQ ID NO: 8, optionally wherein the first polypeptide comprises a deletion of the amino acids corresponding to amino acids 161-165 of SEQ ID NO: 8; or (d) a first polypeptide comprising the amino acid sequence having at least 90% identity to amino acids 32-494 of SEQ ID NO: 9; and a second polypeptide comprising the amino acid sequence having at least 90% identity to amino acids 495-728 of SEQ ID NO: 9, optionally wherein the first polypeptide comprises a deletion of the amino acids corresponding to amino acids 161-165 of SEQ ID NO: 9; or (e) a first polypeptide comprising the amino acid sequence having at least 90% identity to amino acids 32-494 of SEQ ID NO: 10; and a second polypeptide comprising the amino acid sequence having at least 90% identity to amino acids 495-728 of SEQ ID NO: 10, optionally wherein the first polypeptide comprises a deletion of the amino acids corresponding to amino acids 161-165 of SEQ ID NO: 10; or (f) a first polypeptide comprising the amino acid sequence having at least 90% identity to amino acids 32-494 of SEQ ID NO: 11; and a second polypeptide comprising the amino acid sequence having at least 90% identity to amino acids 495-728 of SEQ ID NO: 11, optionally wherein the first polypeptide comprises a deletion of the amino acids corresponding to amino acids 161-165 of SEQ ID NO: 11; or (g) a first polypeptide comprising the amino acid sequence having at least 90% identity to amino acids 32-494 of SEQ ID NO: 12; and a second polypeptide comprising the amino acid sequence having at 90% identity to amino acids 495-728 of SEQ ID NO: 12, optionally wherein the first polypeptide comprises a deletion of the amino acids corresponding to amino acids 161-165 of SEQ ID NO: 12; or (h) a first polypeptide comprising the amino acid sequence having at least 90% identity to amino acids 32-494 of SEQ ID NO: 13; and a second polypeptide comprising the amino acid sequence having at least 90% identity to amino acids 495-728 of SEQ ID NO: 13, optionally wherein the first polypeptide comprises a deletion of the amino acids corresponding to amino acids 161-165 of SEQ ID NO: 13; or (i) a first polypeptide comprising the amino acid sequence having at least 90% identity to amino acids 32-494 of SEQ ID NO: 14; and a second polypeptide comprising the amino acid sequence having at least 90% identity to amino acids 495-728 of SEQ ID NO: 14, optionally wherein the first polypeptide comprises a deletion of the amino acids corresponding to amino acids 161-165 of SEQ ID NO: 14; or (j) a first polypeptide comprising the amino acid sequence having at least 90% identity to amino acids 32-494 of SEQ ID NO: 15; and a second polypeptide comprising the amino acid sequence having at least 90% identity to amino acids 495-728 of SEQ ID NO: 15, optionally wherein the first polypeptide comprises a deletion of the amino acids corresponding to amino acids 161-165 of SEQ ID NO: 15; or (k) a first polypeptide comprising the amino acid sequence having at least 90% identity to amino acids 32-494 of SEQ ID NO: 16; and a second polypeptide comprising the amino acid sequence having at least 90% identity to amino acids 495-728 of SEQ ID NO: 16, optionally wherein the first polypeptide comprises a deletion of the amino acids corresponding to amino acids 161-165 of SEQ ID NO: 16; or (l) a first polypeptide comprising the amino acid sequence having at least 90% identity to amino acids 32-494 of SEQ ID NO: 17; and a second polypeptide comprising the amino acid sequence having at least 90% identity to amino acids 495-728 of SEQ ID NO: 17, optionally wherein the first polypeptide comprises a deletion of the amino acids corresponding to amino acids 161-165 of SEQ ID NO: 17; or (m) a first polypeptide comprising the amino acid sequence having at least identity to amino acids 32-494 of SEQ ID NO: 18; and a second polypeptide comprising the amino acid sequence having at least 90% identity to amino acids 495-728 of SEQ ID NO: 18, optionally wherein the first polypeptide comprises a deletion of the amino acids corresponding to amino acids 161-165 of SEQ ID NO: 18; or (n) a first polypeptide comprising the amino acid sequence having at least identity to amino acids 32-494 of SEQ ID NO: 19; and a second polypeptide comprising the amino acid sequence having at least 90% identity to amino acids 495-728 of SEQ ID NO: 19, optionally wherein the first polypeptide comprises a deletion of the amino acids corresponding to amino acids 161-165 of SEQ ID NO: 19; or (o) a first polypeptide comprising the amino acid sequence having at least 90% identity to amino acids 32-494 of SEQ ID NO: 20; and a second polypeptide comprising the amino acid sequence having at least 90% identity to amino acids 495-728 of SEQ ID NO: 20, optionally wherein the first polypeptide comprises a deletion of the amino acids corresponding to amino acids 161-165 of SEQ ID NO: 20; or (p) a first polypeptide comprising the amino acid sequence having at least 90% identity to amino acids 32-494 of SEQ ID NO: 21; and a second polypeptide comprising the amino acid sequence having at least 90% identity to amino acids 495-728 of SEQ ID NO: 21, optionally wherein the first polypeptide comprises a deletion of the amino acids corresponding to amino acids 161-165 of SEQ ID NO: 21; or (q) a first polypeptide comprising the amino acid sequence having at least 90% identity to amino acids 32-494 of SEQ ID NO: 22; and a second polypeptide comprising the amino acid sequence having at least 90% identity to amino acids 495-728 of SEQ ID NO: 22, optionally wherein the first polypeptide comprises a deletion of the amino acids corresponding to amino acids 161-165 of SEQ ID NO: 22; or (r) a first polypeptide comprising the amino acid sequence having at least 90% identity to amino acids 32-494 of SEQ ID NO: 23; and a second polypeptide comprising the amino acid sequence having at least 90% identity to amino acids 495-728 of SEQ ID NO: 23, optionally wherein the first polypeptide comprises a deletion of the amino acids corresponding to amino acids 161-165 of SEQ ID NO: 23; or (s) a first polypeptide comprising the amino acid sequence having at least 90% identity to amino acids 32-494 of SEQ ID NO: 24; and a second polypeptide comprising the amino acid sequence having at least 90% identity to amino acids 495-728 of SEQ ID NO: 24, optionally wherein the first polypeptide comprises a deletion of the amino acids corresponding to amino acids 161-165 of SEQ ID NO: 24; or (t) a first polypeptide comprising the amino acid sequence having at least 90% identity to amino acids 32-494 of SEQ ID NO: 25; and a second polypeptide comprising the amino acid sequence having at least 90% identity to amino acids 495-728 of SEQ ID NO: 25, optionally wherein the first polypeptide comprises a deletion of the amino acids corresponding to amino acids 161-165 of SEQ ID NO: 25; or (u) a first polypeptide comprising the amino acid sequence having at least 90% identity to amino acids 32-494 of SEQ ID NO: 26; and a second polypeptide comprising the amino acid sequence having at least 90% identity to amino acids 495-728 of SEQ ID NO: 26, optionally wherein the first polypeptide comprises a deletion of the amino acids corresponding to amino acids 161-165 of SEQ ID NO: 26; or (v) a first polypeptide comprising the amino acid sequence having at least 90% identity to amino acids 32-494 of SEQ ID NO: 27; and a second polypeptide comprising the amino acid sequence having at least 90% identity to amino acids 495-728 of SEQ ID NO: 27, optionally wherein the first polypeptide comprises a deletion of the amino acids corresponding to amino acids 161-165 of SEQ ID NO: 27.

6. The composition of claim 1, wherein the surfactant is present in an amount of about 0.05% (w/v).

7. An aqueous pharmaceutical composition consisting of:

about 0.1% (w/v) deleted hepatocyte growth factor (dHGF) in activated form;

about 20 mM sodium citrate buffer having a pH of about 6.0;

about 200 mM trehalose, and about 0.05% (w/v) polysorbate 80.

8. The composition of claim 7, wherein the dHGF comprises:

(a) a first polypeptide comprising the amino acid sequence having at least 90% identity to amino acids 32-494 of SEQ ID NO: 2; and a second polypeptide comprising the amino acid sequence having at least 90% identity to amino acids 495-728 of SEQ ID NO: 2, wherein the first polypeptide comprises a deletion of the amino acids corresponding to amino acids 161-165 of SEQ ID NO: 2; or (b) a first polypeptide comprising the amino acid sequence having at least 90% identity to amino acids 32-494 of SEQ ID NO: 7; and a second polypeptide comprising the amino acid sequence having at least 90% identity to amino acids 495-728 of SEQ ID NO: 7, wherein the first polypeptide comprises a deletion of the amino acids corresponding to amino acids 161-165 of SEQ ID NO: 7; or (c) a first polypeptide comprising the amino acid sequence having at least 90% identity to amino acids 32-494 of SEQ ID NO: 8; and a second polypeptide comprising the amino acid sequence having at least 90% identity to amino acids 495-728 of SEQ ID NO: 8, wherein the first polypeptide comprises a deletion of the amino acids corresponding to amino acids 161-165 of SEQ ID NO: 8; or (d) a first polypeptide comprising the amino acid sequence having at least 90% identity to amino acids 32-494 of SEQ ID NO: 9; and a second polypeptide comprising the amino acid sequence having at least 90% identity to amino acids 495-728 of SEQ ID NO: 9, wherein the first polypeptide comprises a deletion of the amino acids corresponding to amino acids 161-165 of SEQ ID NO: 9; or (e) a first polypeptide comprising the amino acid sequence having at least 90% identity to amino acids 32-494 of SEQ ID NO: 10; and a second polypeptide comprising the amino acid sequence having at least 90% identity to amino acids 495-728 of SEQ ID NO: 10, wherein the first polypeptide comprises a deletion of the amino acids corresponding to amino acids 161-165 of SEQ ID NO: 10; or (f) a first polypeptide comprising the amino acid sequence having at least 90% identity to amino acids 32-494 of SEQ ID NO: 11; and a second polypeptide comprising the amino acid sequence having at least 90% identity to amino acids 495-728 of SEQ ID NO: 11, wherein the first polypeptide comprises a deletion of the amino acids corresponding to amino acids 161-165 of SEQ ID NO: 11; or (g) a first polypeptide comprising the amino acid sequence having at least 90% identity to amino acids 32-494 of SEQ ID NO: 12; and a second polypeptide comprising the amino acid sequence having at 90% identity to amino acids 495-728 of SEQ ID NO: 12, wherein the first polypeptide comprises a deletion of the amino acids corresponding to amino acids 161-165 of SEQ ID NO: 12; or (h) a first polypeptide comprising the amino acid sequence having at least 90% identity to amino acids 32-494 of SEQ ID NO: 13; and a second polypeptide comprising the amino acid sequence having at least 90% identity to amino acids 495-728 of SEQ ID NO: 13, wherein the first polypeptide comprises a deletion of the amino acids corresponding to amino acids 161-165 of SEQ ID NO: 13; or (i) a first polypeptide comprising the amino acid sequence having at least 90% identity to amino acids 32-494 of SEQ ID NO: 14; and a second polypeptide comprising the amino acid sequence having at least 90% identity to amino acids 495-728 of SEQ ID NO: 14, wherein the first polypeptide comprises a deletion of the amino acids corresponding to amino acids 161-165 of SEQ ID NO: 14; or (j) a first polypeptide comprising the amino acid sequence having at least 90% identity to amino acids 32-494 of SEQ ID NO: 15; and a second polypeptide comprising the amino acid sequence having at least 90% identity to amino acids 495-728 of SEQ ID NO: 15, wherein the first polypeptide comprises a deletion of the amino acids corresponding to amino acids 161-165 of SEQ ID NO: 15; or (k) a first polypeptide comprising the amino acid sequence having at least 90% identity to amino acids 32-494 of SEQ ID NO: 16; and a second polypeptide comprising the amino acid sequence having at least 90% identity to amino acids 495-728 of SEQ ID NO: 16, wherein the first polypeptide comprises a deletion of the amino acids corresponding to amino acids 161-165 of SEQ ID NO: 16; or (l) a first polypeptide comprising the amino acid sequence having at least 90% identity to amino acids 32-494 of SEQ ID NO: 17; and a second polypeptide comprising the amino acid sequence having at least 90% identity to amino acids 495-728 of SEQ ID NO: 17, wherein the first polypeptide comprises a deletion of the amino acids corresponding to amino acids 161-165 of SEQ ID NO: 17; or (m) a first polypeptide comprising the amino acid sequence having at least identity to amino acids 32-494 of SEQ ID NO: 18; and a second polypeptide comprising the amino acid sequence having at least 90% identity to amino acids 495-728 of SEQ ID NO: 18, wherein the first polypeptide comprises a deletion of the amino acids corresponding to amino acids 161-165 of SEQ ID NO: 18; or (n) a first polypeptide comprising the amino acid sequence having at least identity to amino acids 32-494 of SEQ ID NO: 19; and a second polypeptide comprising the amino acid sequence having at least 90% identity to amino acids 495-728 of SEQ ID NO: 19, wherein the first polypeptide comprises a deletion of the amino acids corresponding to amino acids 161-165 of SEQ ID NO: 19; or (o) a first polypeptide comprising the amino acid sequence having at least 90% identity to amino acids 32-494 of SEQ ID NO: 20; and a second polypeptide comprising the amino acid sequence having at least 90% identity to amino acids 495-728 of SEQ ID NO: 20, wherein the first polypeptide comprises a deletion of the amino acids corresponding to amino acids 161-165 of SEQ ID NO: 20; or (p) a first polypeptide comprising the amino acid sequence having at least 90% identity to amino acids 32-494 of SEQ ID NO: 21; and a second polypeptide comprising the amino acid sequence having at least 90% identity to amino acids 495-728 of SEQ ID NO: 21, wherein the first polypeptide comprises a deletion of the amino acids corresponding to amino acids 161-165 of SEQ ID NO: 21; or (q) a first polypeptide comprising the amino acid sequence having at least 90% identity to amino acids 32-494 of SEQ ID NO: 22; and a second polypeptide comprising the amino acid sequence having at least 90% identity to amino acids 495-728 of SEQ ID NO: 22, wherein the first polypeptide comprises a deletion of the amino acids corresponding to amino acids 161-165 of SEQ ID NO: 22; or (r) a first polypeptide comprising the amino acid sequence having at least 90% identity to amino acids 32-494 of SEQ ID NO: 23; and a second polypeptide comprising the amino acid sequence having at least 90% identity to amino acids 495-728 of SEQ ID NO: 23, wherein the first polypeptide comprises a deletion of the amino acids corresponding to amino acids 161-165 of SEQ ID NO: 23; or (s) a first polypeptide comprising the amino acid sequence having at least 90% identity to amino acids 32-494 of SEQ ID NO: 24; and a second polypeptide comprising the amino acid sequence having at least 90% identity to amino acids 495-728 of SEQ ID NO: 24, wherein the first polypeptide comprises a deletion of the amino acids corresponding to amino acids 161-165 of SEQ ID NO: 24; or (t) a first polypeptide comprising the amino acid sequence having at least 90% identity to amino acids 32-494 of SEQ ID NO: 25; and a second polypeptide comprising the amino acid sequence having at least 90% identity to amino acids 495-728 of SEQ ID NO: 25, wherein the first polypeptide comprises a deletion of the amino acids corresponding to amino acids 161-165 of SEQ ID NO: 25; or (u) a first polypeptide comprising the amino acid sequence having at least 90% identity to amino acids 32-494 of SEQ ID NO: 26; and a second polypeptide comprising the amino acid sequence having at least 90% identity to amino acids 495-728 of SEQ ID NO: 26, wherein the first polypeptide comprises a deletion of the amino acids corresponding to amino acids 161-165 of SEQ ID NO: 26; or (v) a first polypeptide comprising the amino acid sequence having at least 90% identity to amino acids 32-494 of SEQ ID NO: 27; and a second polypeptide comprising the amino acid sequence having at least 90% identity to amino acids 495-728 of SEQ ID NO: 27, wherein the first polypeptide comprises a deletion of the amino acids corresponding to amino acids 161-165 of SEQ ID NO: 27.

9. The composition of claim 7, wherein the dHGF comprises:

a first polypeptide comprising the amino acid sequence having at least 90% identity to amino acids 32-494 of SEQ ID NO: 2; and a second polypeptide comprising the amino acid sequence having at least 90% identity to amino acids 495-728 of SEQ ID NO: 2, wherein the first polypeptide comprises a deletion of the amino acids corresponding to amino acids 161-165 of SEQ ID NO: 2.

10. The composition of claim 7, wherein the dHGF comprises:

a first polypeptide comprising the amino acid sequence having at least 95% identity to amino acids 32-494 of SEQ ID NO: 2; and a second polypeptide comprising the amino acid sequence having at least 95% identity to amino acids 495-728 of SEQ ID NO: 2, wherein the first polypeptide comprises a deletion of the amino acids corresponding to amino acids 161-165 of SEQ ID NO: 2.

11. The composition of claim 7, wherein the dHGF comprises:

a first polypeptide comprising the amino acid sequence having at least 98% identity to amino acids 32-494 of SEQ ID NO: 2; and a second polypeptide comprising the amino acid sequence having at least 98% identity to amino acids 495-728 of SEQ ID NO: 2, wherein the first polypeptide comprises a deletion of the amino acids corresponding to amino acids 161-165 of SEQ ID NO: 2.

12. The composition of claim 7, wherein the dHGF comprises:

a first polypeptide comprising the amino acid sequence having at least 99% identity to amino acids 32-494 of SEQ ID NO: 2; and a second polypeptide comprising the amino acid sequence having at least 99% identity to amino acids 495-728 of SEQ ID NO: 2, wherein the first polypeptide comprises a deletion of the amino acids corresponding to amino acids 161-165 of SEQ ID NO: 2.

13. The composition of claim 7, wherein the dHGF comprises:

a first polypeptide comprising the amino acid sequence corresponding to amino acids 32-494 of SEQ ID NO: 2; and a second polypeptide comprising the amino acid sequence corresponding to amino acids 495-728 of SEQ ID NO: 2, wherein the first polypeptide comprises a deletion of the amino acids corresponding to amino acids 161-165 of SEQ ID NO: 2.

* * * * *

SEQUENCE LISTING

<160> NUMBER OF SEQ ID NOS: 38

<210> SEQ ID NO 1
<211> LENGTH: 723
<212> TYPE: PRT
<213> ORGANISM: Homo sapiens

<400> SEQUENCE: 1

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Ala Asp Asn Thr Met
        275                 280                 285

Asn Asp Thr Asp Val Pro Leu Glu Thr Thr Glu Cys Ile Gln Gly Gln
    290                 295                 300

Gly Glu Gly Tyr Arg Gly Thr Val Asn Thr Ile Trp Asn Gly Ile Pro
305                 310                 315                 320

Cys Gln Arg Trp Asp Ser Gln Tyr Pro His Glu His Asp Met Thr Pro
                325                 330                 335

Glu Asn Phe Lys Cys Lys Asp Leu Arg Glu Asn Tyr Cys Arg Asn Pro
            340                 345                 350

Asp Gly Ser Glu Ser Pro Trp Cys Phe Thr Thr Asp Pro Asn Ile Arg
        355                 360                 365
```

```
Val Gly Tyr Cys Ser Gln Ile Pro Asn Cys Asp Met Ser His Gly Gln
    370                 375                 380

Asp Cys Tyr Arg Gly Asn Gly Lys Asn Tyr Met Gly Asn Leu Ser Gln
385                 390                 395                 400

Thr Arg Ser Gly Leu Thr Cys Ser Met Trp Asp Lys Asn Met Glu Asp
                405                 410                 415

Leu His Arg His Ile Phe Trp Glu Pro Asp Ala Ser Lys Leu Asn Glu
            420                 425                 430

Asn Tyr Cys Arg Asn Pro Asp Asp Asp Ala His Gly Pro Trp Cys Tyr
        435                 440                 445

Thr Gly Asn Pro Leu Ile Pro Trp Asp Tyr Cys Pro Ile Ser Arg Cys
    450                 455                 460

Glu Gly Asp Thr Thr Pro Thr Ile Val Asn Leu Asp His Pro Val Ile
465                 470                 475                 480

Ser Cys Ala Lys Thr Lys Gln Leu Arg Val Val Asn Gly Ile Pro Thr
                485                 490                 495

Arg Thr Asn Ile Gly Trp Met Val Ser Leu Arg Tyr Arg Asn Lys His
            500                 505                 510

Ile Cys Gly Gly Ser Leu Ile Lys Glu Ser Trp Val Leu Thr Ala Arg
        515                 520                 525

Gln Cys Phe Pro Ser Arg Asp Leu Lys Asp Tyr Glu Ala Trp Leu Gly
    530                 535                 540

Ile His Asp Val His Gly Arg Gly Asp Glu Lys Cys Lys Gln Val Leu
545                 550                 555                 560

Asn Val Ser Gln Leu Val Tyr Gly Pro Glu Gly Ser Asp Leu Val Leu
                565                 570                 575

Met Lys Leu Ala Arg Pro Ala Val Leu Asp Asp Phe Val Ser Thr Ile
            580                 585                 590

Asp Leu Pro Asn Tyr Gly Cys Thr Ile Pro Glu Lys Thr Ser Cys Ser
        595                 600                 605

Val Tyr Gly Trp Gly Tyr Thr Gly Leu Ile Asn Tyr Asp Gly Leu Leu
    610                 615                 620

Arg Val Ala His Leu Tyr Ile Met Gly Asn Glu Lys Cys Ser Gln His
625                 630                 635                 640

His Arg Gly Lys Val Thr Leu Asn Glu Ser Glu Ile Cys Ala Gly Ala
                645                 650                 655

Glu Lys Ile Gly Ser Gly Pro Cys Glu Gly Asp Tyr Gly Gly Pro Leu
            660                 665                 670

Val Cys Glu Gln His Lys Met Arg Met Val Leu Gly Val Ile Val Pro
        675                 680                 685

Gly Arg Gly Cys Ala Ile Pro Asn Arg Pro Gly Ile Phe Val Arg Val
    690                 695                 700

Ala Tyr Tyr Ala Lys Trp Ile His Lys Ile Ile Leu Thr Tyr Lys Val
705                 710                 715                 720

Pro Gln Ser


<210> SEQ ID NO 2
<211> LENGTH: 728
<212> TYPE: PRT
<213> ORGANISM: Homo sapiens

<400> SEQUENCE: 2

Met Trp Val Thr Lys Leu Leu Pro Ala Leu Leu Leu Gln His Val Leu
1               5                   10                  15
```

```
Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
```

```
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725


<210> SEQ ID NO 3
<211> LENGTH: 290
<212> TYPE: PRT
<213> ORGANISM: Homo sapiens

<400> SEQUENCE: 3

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80
```

```
Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Glu Thr
    290


<210> SEQ ID NO 4
<211> LENGTH: 296
<212> TYPE: PRT
<213> ORGANISM: Homo sapiens

<400> SEQUENCE: 4

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160
```

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Asn Met
        275                 280                 285

Arg Asp Ile Thr Trp Ala Leu Asn
    290                 295

<210> SEQ ID NO 5
<211> LENGTH: 285
<212> TYPE: PRT
<213> ORGANISM: Homo sapiens

<400> SEQUENCE: 5

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Tyr Arg Gly Lys Asp Leu Gln Glu Asn Tyr Cys Arg Asn Pro Arg
                165                 170                 175

Gly Glu Glu Gly Gly Pro Trp Cys Phe Thr Ser Asn Pro Glu Val Arg
            180                 185                 190

Tyr Glu Val Cys Asp Ile Pro Gln Cys Ser Glu Val Glu Cys Met Thr
        195                 200                 205

Cys Asn Gly Glu Ser Tyr Arg Gly Leu Met Asp His Thr Glu Ser Gly
    210                 215                 220

Lys Ile Cys Gln Arg Trp Asp His Gln Thr Pro His Arg His Lys Phe

```
225                 230                 235                 240

Leu Pro Glu Arg Tyr Pro Asp Lys Gly Phe Asp Asp Asn Tyr Cys Arg
                245                 250                 255

Asn Pro Asp Gly Gln Pro Arg Pro Trp Cys Tyr Thr Leu Asp Pro His
            260                 265                 270

Thr Arg Trp Glu Tyr Cys Ala Ile Lys Thr Cys Glu Thr
        275                 280                 285


<210> SEQ ID NO 6
<211> LENGTH: 210
<212> TYPE: PRT
<213> ORGANISM: Homo sapiens

<400> SEQUENCE: 6

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Gly Lys
    210


<210> SEQ ID NO 7
<211> LENGTH: 728
<212> TYPE: PRT
<213> ORGANISM: Artificial Sequence
<220> FEATURE:
<223> OTHER INFORMATION: HGF Variant

<400> SEQUENCE: 7

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45
```

```
Thr Leu Ile Lys Ile Asp Pro Ala Leu Glu Ile Lys Thr Lys Lys Ala
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Ile Gly Lys Gly Arg Ser Tyr Arg Gly Thr Val Ser Ile Thr Lys
    130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460
```

Pro Ile Ser Arg Cys Glu Gly Asp Thr Thr Pro Thr Ile Val Asn Leu
465 470 475 480

Asp His Pro Val Ile Ser Cys Ala Lys Thr Lys Gln Leu Arg Val Val
485 490 495

Asn Gly Ile Pro Thr Arg Thr Asn Ile Gly Trp Met Val Ser Leu Arg
500 505 510

Tyr Arg Asn Lys His Ile Cys Gly Gly Ser Leu Ile Lys Glu Ser Trp
515 520 525

Val Leu Thr Ala Arg Gln Cys Phe Pro Ser Arg Asp Leu Lys Asp Tyr
530 535 540

Glu Ala Trp Leu Gly Ile His Asp Val His Gly Arg Gly Asp Glu Lys
545 550 555 560

Cys Lys Gln Val Leu Asn Val Ser Gln Leu Val Tyr Gly Pro Glu Gly
565 570 575

Ser Asp Leu Val Leu Met Lys Leu Ala Arg Pro Ala Val Leu Asp Asp
580 585 590

Phe Val Ser Thr Ile Asp Leu Pro Asn Tyr Gly Cys Thr Ile Pro Glu
595 600 605

Lys Thr Ser Cys Ser Val Tyr Gly Trp Gly Tyr Thr Gly Leu Ile Asn
610 615 620

Tyr Asp Gly Leu Leu Arg Val Ala His Leu Tyr Ile Met Gly Asn Glu
625 630 635 640

Lys Cys Ser Gln His His Arg Gly Lys Val Thr Leu Asn Glu Ser Glu
645 650 655

Ile Cys Ala Gly Ala Glu Lys Ile Gly Ser Gly Pro Cys Glu Gly Asp
660 665 670

Tyr Gly Gly Pro Leu Val Cys Glu Gln His Lys Met Arg Met Val Leu
675 680 685

Gly Val Ile Val Pro Gly Arg Gly Cys Ala Ile Pro Asn Arg Pro Gly
690 695 700

Ile Phe Val Arg Val Ala Tyr Tyr Ala Lys Trp Ile His Lys Ile Ile
705 710 715 720

Leu Thr Tyr Lys Val Pro Gln Ser
725

<210> SEQ ID NO 8
<211> LENGTH: 728
<212> TYPE: PRT
<213> ORGANISM: Artificial Sequence
<220> FEATURE:
<223> OTHER INFORMATION: HGF Variant

<400> SEQUENCE: 8

Met Trp Val Thr Lys Leu Leu Pro Ala Leu Leu Leu Gln His Val Leu
1 5 10 15

Leu His Leu Leu Leu Leu Pro Ile Ala Ile Pro Tyr Ala Glu Gly Gln
20 25 30

Arg Lys Arg Arg Asn Thr Ile His Glu Phe Lys Lys Ser Ala Lys Thr
35 40 45

Thr Leu Ile Lys Ile Asp Pro Ala Leu Lys Ile Lys Thr Glu Lys Ala
50 55 60

Asn Thr Ala Asp Gln Cys Ala Asn Arg Cys Ile Arg Asn Lys Gly Leu
65 70 75 80

Pro Phe Thr Cys Lys Ala Phe Val Phe Asp Lys Ala Arg Lys Arg Cys
85 90 95

-continued

```
Leu Trp Phe Pro Val Asn Ser Met Ser Ser Gly Val Lys Lys Glu Phe
            100                 105                 110

Gly His Glu Phe Asp Leu Tyr Glu Asn Lys Asp Tyr Thr Arg Asn Cys
        115                 120                 125

Ile Val Gly Asn Gly Arg Ser Tyr Arg Gly Thr Val Ser Thr Thr Lys
    130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
```

```
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725


<210> SEQ ID NO 9
<211> LENGTH: 728
<212> TYPE: PRT
<213> ORGANISM: Artificial Sequence
<220> FEATURE:
<223> OTHER INFORMATION: HGF Variant

<400> SEQUENCE: 9

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Val Gly Asn Gly Arg Ser Tyr Arg Gly Thr Val Ser Ile Thr Lys
    130                 135                 140

Ser Gly Ile Glu Cys Gln Pro Trp Ser Ala Met Ile Pro His Glu His
```

-continued

```
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575
```

```
Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725


<210> SEQ ID NO 10
<211> LENGTH: 728
<212> TYPE: PRT
<213> ORGANISM: Artificial Sequence
<220> FEATURE:
<223> OTHER INFORMATION: HGF Variant

<400> SEQUENCE: 10

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Lys Gly Gln
            20                  25                  30

Gly Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asp Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Val Gly Asn Gly Arg Ser Tyr Arg Gly Thr Val Ser Val Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205
```

-continued

```
Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620
```

Tyr Asp Gly Leu Leu Arg Val Ala His Leu Tyr Ile Met Gly Asn Glu
625 630 635 640

Lys Cys Ser Gln His His Arg Gly Lys Val Thr Leu Asn Glu Ser Glu
645 650 655

Ile Cys Ala Gly Ala Glu Lys Ile Gly Ser Gly Pro Cys Glu Gly Asp
660 665 670

Tyr Gly Gly Pro Leu Val Cys Glu Gln His Lys Met Arg Met Val Leu
675 680 685

Gly Val Ile Val Pro Gly Arg Gly Cys Ala Ile Pro Asn Arg Pro Gly
690 695 700

Ile Phe Val Arg Val Ala Tyr Tyr Ala Lys Trp Ile His Lys Ile Ile
705 710 715 720

Leu Thr Tyr Lys Val Pro Gln Ser
725

<210> SEQ ID NO 11
<211> LENGTH: 728
<212> TYPE: PRT
<213> ORGANISM: Artificial Sequence
<220> FEATURE:
<223> OTHER INFORMATION: HGF Variant

<400> SEQUENCE: 11

Met Trp Val Thr Lys Leu Leu Pro Ala Leu Leu Leu Gln His Val Leu
1 5 10 15

Leu His Leu Leu Leu Leu Pro Ile Ala Ile Pro Tyr Ala Glu Gly Gln
20 25 30

Arg Lys Arg Arg Asn Ala Ile His Glu Phe Lys Lys Ser Ala Lys Ala
35 40 45

Thr Leu Ile Lys Ile Asp Pro Ala Leu Lys Ile Lys Thr Glu Lys Ala
50 55 60

Asn Thr Ala Asp Gln Cys Ala Asn Arg Cys Thr Arg Ser Lys Gly Leu
65 70 75 80

Pro Phe Thr Cys Lys Ala Phe Val Phe Asp Lys Ala Arg Lys Arg Cys
85 90 95

Leu Trp Phe Pro Phe Asn Ser Met Ser Ser Gly Val Lys Lys Glu Phe
100 105 110

Gly His Glu Phe Asp Leu Tyr Glu Asn Lys Asp Tyr Ile Arg Asp Cys
115 120 125

Ile Val Gly Asn Gly Arg Ser Tyr Arg Gly Thr Val Ser Ile Thr Lys
130 135 140

Ser Gly Ile Glu Cys Gln Pro Trp Ser Ser Met Ile Pro His Glu His
145 150 155 160

Ser Phe Leu Pro Ser Ser Tyr Arg Gly Glu Asp Leu Gln Glu Asn Tyr
165 170 175

Cys Arg Asn Pro Trp Gly Glu Glu Gly Gly Pro Trp Cys Tyr Thr Ser
180 185 190

Asp Pro Glu Val Arg Tyr Glu Val Cys Asp Ile Pro Gln Cys Ser Glu
195 200 205

Val Glu Cys Met Thr Cys Asn Gly Glu Ser Tyr Arg Gly Leu Met Asp
210 215 220

His Thr Glu Ser Gly Lys Ile Cys Gln Arg Trp Asp His Gln Thr Pro
225 230 235 240

His Arg His Lys Phe Leu Pro Glu Arg Tyr Pro Asp Lys Gly Phe Asp
245 250 255

```
Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
```

```
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725


<210> SEQ ID NO 12
<211> LENGTH: 728
<212> TYPE: PRT
<213> ORGANISM: Artificial Sequence
<220> FEATURE:
<223> OTHER INFORMATION: HGF Variant

<400> SEQUENCE: 12

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Thr Arg Asn Cys
        115                 120                 125

Ile Val Gly Asn Gly Arg Ser Tyr Arg Gly Thr Val Ser Ile Thr Lys
    130                 135                 140

Ser Gly Ile Glu Cys Gln Pro Trp Ser Ala Met Ile Pro His Glu His
145                 150                 155                 160

Ser Phe Leu Pro Ser Ser Tyr Gln Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
```

```
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725
```

<210> SEQ ID NO 13
<211> LENGTH: 728
<212> TYPE: PRT
<213> ORGANISM: Artificial Sequence
<220> FEATURE:
<223> OTHER INFORMATION: HGF Variant

<400> SEQUENCE: 13

Met Trp Val Thr Lys Leu Leu Pro Ala Leu Leu Leu Gln His Val Leu
1 5 10 15

Leu His Leu Leu Leu Leu Pro Ile Ala Ile Pro Tyr Ala Glu Gly Gln
20 25 30

Arg Lys Arg Arg Asn Thr Ile His Glu Phe Lys Lys Ser Ala Lys Thr
35 40 45

Thr Leu Ile Lys Ile Asp Pro Ala Leu Lys Ile Lys Thr Lys Lys Val
50 55 60

Asn Thr Ala Asp Gln Cys Ala Asn Arg Cys Thr Arg Asn Lys Gly Leu
65 70 75 80

Pro Phe Thr Cys Lys Ala Phe Val Phe Asp Lys Ala Arg Lys Gln Cys
85 90 95

Leu Trp Phe Pro Phe Asn Ser Met Ser Ser Gly Val Lys Lys Glu Phe
100 105 110

Gly His Glu Phe Asp Leu Tyr Glu Asn Lys Asp Tyr Ile Arg Asn Cys
115 120 125

Ile Ile Gly Lys Gly Arg Ser Tyr Lys Gly Thr Val Ser Ile Thr Lys
130 135 140

Ser Gly Ile Lys Cys Gln Pro Trp Ser Ser Met Ile Pro His Glu His
145 150 155 160

Ser Phe Leu Pro Ser Ser Tyr Arg Gly Lys Asp Leu Gln Glu Asn Tyr
165 170 175

Cys Arg Asn Pro Arg Gly Glu Glu Gly Gly Pro Trp Cys Phe Thr Ser
180 185 190

Asn Pro Glu Val Arg Tyr Glu Val Cys Asp Ile Pro Gln Cys Ser Glu
195 200 205

Val Glu Cys Met Thr Cys Asn Gly Glu Ser Tyr Arg Gly Leu Met Asp
210 215 220

His Thr Glu Ser Gly Lys Ile Cys Gln Arg Trp Asp His Gln Thr Pro
225 230 235 240

His Arg His Lys Phe Leu Pro Glu Arg Tyr Pro Asp Lys Gly Phe Asp
245 250 255

Asp Asn Tyr Cys Arg Asn Pro Asp Gly Gln Pro Arg Pro Trp Cys Tyr
260 265 270

Thr Leu Asp Pro His Thr Arg Trp Glu Tyr Cys Ala Ile Lys Thr Cys
275 280 285

Ala Asp Asn Thr Met Asn Asp Thr Asp Val Pro Leu Glu Thr Thr Glu
290 295 300

Cys Ile Gln Gly Gln Gly Glu Gly Tyr Arg Gly Thr Val Asn Thr Ile
305 310 315 320

Trp Asn Gly Ile Pro Cys Gln Arg Trp Asp Ser Gln Tyr Pro His Glu
325 330 335

His Asp Met Thr Pro Glu Asn Phe Lys Cys Lys Asp Leu Arg Glu Asn
340 345 350

Tyr Cys Arg Asn Pro Asp Gly Ser Glu Ser Pro Trp Cys Phe Thr Thr
355 360 365

```
Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725
```

<210> SEQ ID NO 14
<211> LENGTH: 728
<212> TYPE: PRT
<213> ORGANISM: Artificial Sequence
<220> FEATURE:
<223> OTHER INFORMATION: HGF Variant

<400> SEQUENCE: 14

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asp Ala Ile His Glu Cys Lys Arg Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Asn Lys Gly Leu
65                  70                  75                  80

Pro Ser Thr Cys Lys Ala Phe Val Phe Asp Lys Ala Arg Lys Arg Arg
                85                  90                  95

Leu Arg Phe Pro Phe Asn Ser Met Ser Ser Gly Val Lys Lys Glu Phe
            100                 105                 110

Gly His Glu Phe Asp Leu Tyr Glu Asn Lys Asp Tyr Thr Arg Asn Cys
        115                 120                 125

Ile Val Gly Lys Gly Arg Ser Tyr Arg Gly Thr Val Ser Thr Thr Lys
    130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415
```

```
Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725


<210> SEQ ID NO 15
<211> LENGTH: 728
<212> TYPE: PRT
<213> ORGANISM: Artificial Sequence
<220> FEATURE:
<223> OTHER INFORMATION: HGF Variant

<400> SEQUENCE: 15

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Gly Lys Arg Arg Asn Thr Ile His Glu Phe Lys Lys Ser Ala Lys Thr
        35                  40                  45
```

-continued

```
Thr Leu Ile Lys Ile Asp Pro Ala Leu Lys Ile Lys Thr Glu Lys Val
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Ile Gly Arg Gly Arg Ser Tyr Arg Gly Thr Val Ser Ile Thr Lys
    130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
```

```
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725


<210> SEQ ID NO 16
<211> LENGTH: 728
<212> TYPE: PRT
<213> ORGANISM: Artificial Sequence
<220> FEATURE:
<223> OTHER INFORMATION: HGF Variant

<400> SEQUENCE: 16

Met Trp Val Thr Lys Leu Leu Pro Ala Leu Leu Leu Gln His Val Leu
1               5                   10                  15

Leu His Leu Leu Leu Leu Pro Ile Ala Ile Pro His Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
```

```
            100                 105                 110

Gly His Glu Phe Asp Leu Tyr Glu Asn Lys Asp Tyr Thr Arg Asn Cys
        115                 120                 125

Ile Val Gly Asn Gly Arg Ser Tyr Arg Gly Thr Val Ser Thr Thr Lys
    130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525
```

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 17
<211> LENGTH: 728
<212> TYPE: PRT
<213> ORGANISM: Artificial Sequence
<220> FEATURE:
<223> OTHER INFORMATION: HGF Variant

<400> SEQUENCE: 17

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Arg Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Ile Gly Asn Gly Arg Ser Tyr Arg Gly Thr Val Ser Val Thr Lys
    130                 135                 140

Ser Gly Ile Lys Cys Gln Pro Trp Ser Ala Met Ile Pro His Glu His
145                 150                 155                 160

```
Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575
```

```
Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725


<210> SEQ ID NO 18
<211> LENGTH: 728
<212> TYPE: PRT
<213> ORGANISM: Artificial Sequence
<220> FEATURE:
<223> OTHER INFORMATION: HGF Variant

<400> SEQUENCE: 18

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Val Gly Asn Gly Arg Ser Tyr Arg Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205
```

```
Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
```

625 630 635 640

Lys Cys Ser Gln His His Arg Gly Lys Val Thr Leu Asn Glu Ser Glu
645 650 655

Ile Cys Ala Gly Ala Glu Lys Ile Gly Ser Gly Pro Cys Glu Gly Asp
660 665 670

Tyr Gly Gly Pro Leu Val Cys Glu Gln His Lys Met Arg Met Val Leu
675 680 685

Gly Val Ile Val Pro Gly Arg Gly Cys Ala Ile Pro Asn Arg Pro Gly
690 695 700

Ile Phe Val Arg Val Ala Tyr Tyr Ala Lys Trp Ile His Lys Ile Ile
705 710 715 720

Leu Thr Tyr Lys Val Pro Gln Ser
725

<210> SEQ ID NO 19
<211> LENGTH: 728
<212> TYPE: PRT
<213> ORGANISM: Artificial Sequence
<220> FEATURE:
<223> OTHER INFORMATION: HGF Variant

<400> SEQUENCE: 19

Met Trp Val Thr Lys Leu Leu Pro Ala Leu Leu Leu Gln His Val Leu
1 5 10 15

Leu His Leu Leu Leu Leu Pro Ile Ala Ile Pro Tyr Ala Glu Gly Gln
20 25 30

Arg Lys Arg Arg Asn Thr Ile His Glu Phe Lys Lys Ser Val Lys Thr
35 40 45

Thr Leu Ile Lys Ile Asp Pro Ala Leu Lys Ile Lys Thr Glu Lys Ala
50 55 60

Asn Thr Ala Asp Gln Cys Ala Asn Arg Cys Thr Arg Ser Lys Gly Leu
65 70 75 80

Pro Phe Thr Cys Lys Ala Phe Val Phe Asp Lys Ala Arg Lys Arg Cys
85 90 95

Leu Trp Phe Pro Val Asn Ser Met Ser Ser Gly Val Lys Lys Glu Ser
100 105 110

Gly His Glu Phe Asp Leu Tyr Glu Asn Lys Asp Tyr Ile Arg Asp Cys
115 120 125

Ile Val Gly Asn Gly Arg Ser Tyr Arg Gly Thr Val Ser Thr Thr Lys
130 135 140

Ser Gly Ile Lys Cys Gln Pro Trp Ser Ala Met Ile Pro His Glu His
145 150 155 160

Ser Phe Leu Pro Ser Ser Tyr Arg Gly Glu Asp Leu Arg Glu Asn Tyr
165 170 175

Cys Arg Asn Pro Arg Gly Glu Glu Gly Gly Pro Trp Cys Tyr Thr Ser
180 185 190

Asp Pro Glu Val Arg Tyr Glu Val Cys Asp Ile Pro Gln Cys Ser Glu
195 200 205

Val Glu Cys Met Thr Cys Asn Gly Glu Ser Tyr Arg Gly Leu Met Asp
210 215 220

His Thr Glu Ser Gly Lys Ile Cys Gln Arg Trp Asp His Gln Thr Pro
225 230 235 240

His Arg His Lys Phe Leu Pro Glu Arg Tyr Pro Asp Lys Gly Phe Asp
245 250 255

Asp Asn Tyr Cys Arg Asn Pro Asp Gly Gln Pro Arg Pro Trp Cys Tyr

```
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685
```

Gly Val Ile Val Pro Gly Arg Gly Cys Ala Ile Pro Asn Arg Pro Gly
690 695 700

Ile Phe Val Arg Val Ala Tyr Tyr Ala Lys Trp Ile His Lys Ile Ile
705 710 715 720

Leu Thr Tyr Lys Val Pro Gln Ser
725

<210> SEQ ID NO 20
<211> LENGTH: 728
<212> TYPE: PRT
<213> ORGANISM: Artificial Sequence
<220> FEATURE:
<223> OTHER INFORMATION: HGF Variant

<400> SEQUENCE: 20

Met Trp Val Thr Lys Leu Leu Pro Ala Leu Leu Leu Gln His Val Leu
1 5 10 15

Leu His Leu Leu Leu Leu Pro Ile Ala Ile Pro Tyr Ala Glu Gly Gln
20 25 30

Arg Lys Arg Arg Asn Thr Ile His Glu Phe Lys Lys Ser Ala Lys Thr
35 40 45

Thr Leu Ile Lys Ile Asp Pro Ala Leu Lys Ile Lys Thr Glu Lys Ala
50 55 60

Asn Thr Ala Asp Gln Cys Ala Asn Arg Cys Thr Arg Ser Lys Gly Leu
65 70 75 80

Pro Phe Thr Cys Lys Ala Phe Val Phe Asp Lys Ala Arg Lys Arg Cys
85 90 95

Leu Trp Phe Pro Phe Asn Ser Met Ser Ser Gly Val Lys Lys Glu Phe
100 105 110

Gly His Glu Phe Asp Leu Tyr Glu Asn Lys Asp Tyr Ile Arg Asp Cys
115 120 125

Ile Val Gly Asn Gly Arg Ser Tyr Arg Gly Thr Val Ser Ile Thr Lys
130 135 140

Ser Gly Ile Lys Cys Gln Pro Trp Ser Ser Met Ile Pro His Glu His
145 150 155 160

Ser Phe Leu Pro Ser Ser Tyr Arg Gly Glu Asp Leu Arg Glu Asn Tyr
165 170 175

Cys Arg Asn Pro Trp Gly Glu Glu Gly Gly Pro Trp Cys Tyr Thr Ser
180 185 190

Asp Pro Glu Val Arg Tyr Glu Val Cys Asp Ile Pro Gln Cys Ser Glu
195 200 205

Val Glu Cys Met Thr Cys Asn Gly Glu Ser Tyr Arg Gly Leu Met Asp
210 215 220

His Thr Glu Ser Gly Lys Ile Cys Gln Arg Trp Asp His Gln Thr Pro
225 230 235 240

His Arg His Lys Phe Leu Pro Glu Arg Tyr Pro Asp Lys Gly Phe Asp
245 250 255

Asp Asn Tyr Cys Arg Asn Pro Asp Gly Gln Pro Arg Pro Trp Cys Tyr
260 265 270

Thr Leu Asp Pro His Thr Arg Trp Glu Tyr Cys Ala Ile Lys Thr Cys
275 280 285

Ala Asp Asn Thr Met Asn Asp Thr Asp Val Pro Leu Glu Thr Thr Glu
290 295 300

Cys Ile Gln Gly Gln Gly Glu Gly Tyr Arg Gly Thr Val Asn Thr Ile
305 310 315 320

-continued

Trp Asn Gly Ile Pro Cys Gln Arg Trp Asp Ser Gln Tyr Pro His Glu
325 330 335

His Asp Met Thr Pro Glu Asn Phe Lys Cys Lys Asp Leu Arg Glu Asn
340 345 350

Tyr Cys Arg Asn Pro Asp Gly Ser Glu Ser Pro Trp Cys Phe Thr Thr
355 360 365

Asp Pro Asn Ile Arg Val Gly Tyr Cys Ser Gln Ile Pro Asn Cys Asp
370 375 380

Met Ser His Gly Gln Asp Cys Tyr Arg Gly Asn Gly Lys Asn Tyr Met
385 390 395 400

Gly Asn Leu Ser Gln Thr Arg Ser Gly Leu Thr Cys Ser Met Trp Asp
405 410 415

Lys Asn Met Glu Asp Leu His Arg His Ile Phe Trp Glu Pro Asp Ala
420 425 430

Ser Lys Leu Asn Glu Asn Tyr Cys Arg Asn Pro Asp Asp Asp Ala His
435 440 445

Gly Pro Trp Cys Tyr Thr Gly Asn Pro Leu Ile Pro Trp Asp Tyr Cys
450 455 460

Pro Ile Ser Arg Cys Glu Gly Asp Thr Thr Pro Thr Ile Val Asn Leu
465 470 475 480

Asp His Pro Val Ile Ser Cys Ala Lys Thr Lys Gln Leu Arg Val Val
485 490 495

Asn Gly Ile Pro Thr Arg Thr Asn Ile Gly Trp Met Val Ser Leu Arg
500 505 510

Tyr Arg Asn Lys His Ile Cys Gly Gly Ser Leu Ile Lys Glu Ser Trp
515 520 525

Val Leu Thr Ala Arg Gln Cys Phe Pro Ser Arg Asp Leu Lys Asp Tyr
530 535 540

Glu Ala Trp Leu Gly Ile His Asp Val His Gly Arg Gly Asp Glu Lys
545 550 555 560

Cys Lys Gln Val Leu Asn Val Ser Gln Leu Val Tyr Gly Pro Glu Gly
565 570 575

Ser Asp Leu Val Leu Met Lys Leu Ala Arg Pro Ala Val Leu Asp Asp
580 585 590

Phe Val Ser Thr Ile Asp Leu Pro Asn Tyr Gly Cys Thr Ile Pro Glu
595 600 605

Lys Thr Ser Cys Ser Val Tyr Gly Trp Gly Tyr Thr Gly Leu Ile Asn
610 615 620

Tyr Asp Gly Leu Leu Arg Val Ala His Leu Tyr Ile Met Gly Asn Glu
625 630 635 640

Lys Cys Ser Gln His His Arg Gly Lys Val Thr Leu Asn Glu Ser Glu
645 650 655

Ile Cys Ala Gly Ala Glu Lys Ile Gly Ser Gly Pro Cys Glu Gly Asp
660 665 670

Tyr Gly Gly Pro Leu Val Cys Glu Gln His Lys Met Arg Met Val Leu
675 680 685

Gly Val Ile Val Pro Gly Arg Gly Cys Ala Ile Pro Asn Arg Pro Gly
690 695 700

Ile Phe Val Arg Val Ala Tyr Tyr Ala Lys Trp Ile His Lys Ile Ile
705 710 715 720

Leu Thr Tyr Lys Val Pro Gln Ser
725

<210> SEQ ID NO 21
<211> LENGTH: 728
<212> TYPE: PRT
<213> ORGANISM: Artificial Sequence
<220> FEATURE:
<223> OTHER INFORMATION: HGF Variant

<400> SEQUENCE: 21

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Arg Ile Lys Thr Glu Lys Ala
    50                  55                  60

Asn Thr Ala Asp Gln Cys Ala Asn Arg Cys Thr Arg Ser Arg Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Ile Gly Asn Gly Arg Ser Tyr Arg Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365
```

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 22
<211> LENGTH: 728
<212> TYPE: PRT
<213> ORGANISM: Artificial Sequence
<220> FEATURE:
<223> OTHER INFORMATION: HGF Variant

<400> SEQUENCE: 22

```
Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
    50                  55                  60

Asn Thr Ala Asp Gln Cys Ala Asn Arg Cys Thr Arg Ser Arg Arg Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Ile Gly Lys Gly Arg Ser Tyr Arg Gly Thr Val Ser Val Thr Lys
    130                 135                 140

Ser Gly Ile Glu Cys Gln Pro Trp Ser Ala Met Ile Pro His Glu His
145                 150                 155                 160

Ser Phe Leu Pro Ser Asn Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
```

```
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725


<210> SEQ ID NO 23
<211> LENGTH: 728
<212> TYPE: PRT
<213> ORGANISM: Artificial Sequence
<220> FEATURE:
<223> OTHER INFORMATION: HGF Variant

<400> SEQUENCE: 23

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Ala
```

```
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Val Gly Asn Gly Arg Ser Tyr Arg Gly Thr Val Ser Ile Thr Lys
    130                 135                 140

Ser Gly Ile Glu Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480
```

Asp His Pro Val Ile Ser Cys Ala Lys Thr Lys Gln Leu Arg Val Val
485 490 495

Asn Gly Ile Pro Thr Arg Thr Asn Ile Gly Trp Met Val Ser Leu Arg
500 505 510

Tyr Arg Asn Lys His Ile Cys Gly Gly Ser Leu Ile Lys Glu Ser Trp
515 520 525

Val Leu Thr Ala Arg Gln Cys Phe Pro Ser Arg Asp Leu Lys Asp Tyr
530 535 540

Glu Ala Trp Leu Gly Ile His Asp Val His Gly Arg Gly Asp Glu Lys
545 550 555 560

Cys Lys Gln Val Leu Asn Val Ser Gln Leu Val Tyr Gly Pro Glu Gly
565 570 575

Ser Asp Leu Val Leu Met Lys Leu Ala Arg Pro Ala Val Leu Asp Asp
580 585 590

Phe Val Ser Thr Ile Asp Leu Pro Asn Tyr Gly Cys Thr Ile Pro Glu
595 600 605

Lys Thr Ser Cys Ser Val Tyr Gly Trp Gly Tyr Thr Gly Leu Ile Asn
610 615 620

Tyr Asp Gly Leu Leu Arg Val Ala His Leu Tyr Ile Met Gly Asn Glu
625 630 635 640

Lys Cys Ser Gln His His Arg Gly Lys Val Thr Leu Asn Glu Ser Glu
645 650 655

Ile Cys Ala Gly Ala Glu Lys Ile Gly Ser Gly Pro Cys Glu Gly Asp
660 665 670

Tyr Gly Gly Pro Leu Val Cys Glu Gln His Lys Met Arg Met Val Leu
675 680 685

Gly Val Ile Val Pro Gly Arg Gly Cys Ala Ile Pro Asn Arg Pro Gly
690 695 700

Ile Phe Val Arg Val Ala Tyr Tyr Ala Lys Trp Ile His Lys Ile Ile
705 710 715 720

Leu Thr Tyr Lys Val Pro Gln Ser
725

<210> SEQ ID NO 24
<211> LENGTH: 728
<212> TYPE: PRT
<213> ORGANISM: Artificial Sequence
<220> FEATURE:
<223> OTHER INFORMATION: HGF Variant

<400> SEQUENCE: 24

Met Trp Val Thr Lys Leu Leu Pro Ala Leu Leu Leu Gln His Val Leu
1 5 10 15

Leu His Leu Leu Leu Leu Pro Ile Ala Ile Pro Tyr Ala Glu Gly Gln
20 25 30

Arg Lys Arg Arg Asn Thr Ile His Glu Phe Lys Lys Ser Ala Lys Thr
35 40 45

Thr Leu Ile Lys Ile Asp Pro Ala Leu Lys Ile Lys Thr Lys Lys Val
50 55 60

Asp Thr Ala Asp Gln Cys Ala Asn Arg Cys Thr Arg Asn Lys Gly Leu
65 70 75 80

Pro Phe Thr Cys Lys Ala Phe Val Phe Asp Lys Ala Arg Lys Arg Cys
85 90 95

Leu Trp Phe Pro Phe Asn Ser Met Ser Ser Gly Val Lys Lys Glu Phe
100 105 110

```
Gly His Glu Phe Asp Leu Tyr Glu Asn Lys Asp Tyr Ile Arg Asp Cys
        115                 120                 125

Ile Ile Gly Asn Gly Arg Ser Tyr Arg Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525
```

```
Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725


<210> SEQ ID NO 25
<211> LENGTH: 728
<212> TYPE: PRT
<213> ORGANISM: Artificial Sequence
<220> FEATURE:
<223> OTHER INFORMATION: HGF Variant

<400> SEQUENCE: 25

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Gly Lys Arg Arg Asn Thr Ile His Glu Phe Lys Lys Ser Ala Lys Thr
        35                  40                  45

Thr Leu Ile Lys Ile Asp Pro Ala Leu Arg Ile Lys Thr Glu Lys Ala
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Ala Tyr Ile Arg Asp Cys
        115                 120                 125

Ile Ile Gly Arg Gly Arg Asn Tyr Arg Gly Thr Val Ser Ile Thr Lys
    130                 135                 140

Ser Gly Ile Lys Cys Gln Pro Trp Ser Ala Met Ile Pro His Glu His
145                 150                 155                 160
```

```
Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
```

580 585 590

Phe Val Ser Thr Ile Asp Leu Pro Asn Tyr Gly Cys Thr Ile Pro Glu
595 600 605

Lys Thr Ser Cys Ser Val Tyr Gly Trp Gly Tyr Thr Gly Leu Ile Asn
610 615 620

Tyr Asp Gly Leu Leu Arg Val Ala His Leu Tyr Ile Met Gly Asn Glu
625 630 635 640

Lys Cys Ser Gln His His Arg Gly Lys Val Thr Leu Asn Glu Ser Glu
645 650 655

Ile Cys Ala Gly Ala Glu Lys Ile Gly Ser Gly Pro Cys Glu Gly Asp
660 665 670

Tyr Gly Gly Pro Leu Val Cys Glu Gln His Lys Met Arg Met Val Leu
675 680 685

Gly Val Ile Val Pro Gly Arg Gly Cys Ala Ile Pro Asn Arg Pro Gly
690 695 700

Ile Phe Val Arg Val Ala Tyr Tyr Ala Lys Trp Ile His Lys Ile Ile
705 710 715 720

Leu Thr Tyr Lys Val Pro Gln Ser
725

<210> SEQ ID NO 26
<211> LENGTH: 728
<212> TYPE: PRT
<213> ORGANISM: Artificial Sequence
<220> FEATURE:
<223> OTHER INFORMATION: HGF Variant

<400> SEQUENCE: 26

Met Trp Val Thr Lys Leu Leu Pro Ala Leu Leu Leu Gln His Val Leu
1 5 10 15

Leu His Leu Leu Leu Leu Pro Ile Ala Ile Pro Tyr Ala Lys Gly Gln
20 25 30

Arg Lys Arg Arg Asn Thr Ile His Glu Phe Lys Lys Ser Ala Lys Thr
35 40 45

Thr Leu Ile Lys Ile Asp Pro Ala Leu Glu Ile Lys Thr Glu Lys Val
50 55 60

Asn Thr Ala Asp Gln Cys Ala Asn Arg Cys Ile Arg Asn Lys Gly Leu
65 70 75 80

Pro Phe Thr Cys Lys Ala Phe Val Phe Asp Lys Ala Arg Lys Arg Cys
85 90 95

Leu Trp Phe Pro Phe Asn Ser Met Ser Ser Gly Val Lys Lys Glu Phe
100 105 110

Gly His Glu Phe Asp Leu Tyr Glu Asn Lys Ala Tyr Ile Arg Asp Cys
115 120 125

Ile Ile Gly Arg Gly Arg Asn Tyr Arg Gly Thr Val Ser Ile Thr Lys
130 135 140

Ser Gly Ile Lys Cys Gln Pro Trp Ser Ala Met Ile Pro His Glu His
145 150 155 160

Ser Phe Leu Pro Ser Ser Tyr Arg Gly Glu Asp Leu Arg Glu Asn Tyr
165 170 175

Cys Arg Asn Pro Arg Gly Glu Glu Gly Gly Pro Trp Cys Tyr Thr Ser
180 185 190

Asp Pro Glu Val Arg Tyr Glu Val Cys Asp Ile Pro Gln Cys Ser Glu
195 200 205

Val Glu Cys Met Thr Cys Asn Gly Glu Ser Tyr Arg Gly Leu Met Asp

```
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640
```

```
Lys Cys Ser Gln His His Arg Gly Lys Val Thr Leu Asn Glu Ser Glu
            645                 650                 655

Ile Cys Ala Gly Ala Glu Lys Ile Gly Ser Gly Pro Cys Glu Gly Asp
        660                 665                 670

Tyr Gly Gly Pro Leu Val Cys Glu Gln His Lys Met Arg Met Val Leu
    675                 680                 685

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
            725


<210> SEQ ID NO 27
<211> LENGTH: 728
<212> TYPE: PRT
<213> ORGANISM: Artificial Sequence
<220> FEATURE:
<223> OTHER INFORMATION: HGF Variant

<400> SEQUENCE: 27

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Gly Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Glu Lys Val
    50                  55                  60

Asn Thr Ala Asp Gln Cys Ala Asn Arg Cys Thr Arg Ser Lys Gly Leu
65                  70                  75                  80

Pro Phe Thr Cys Lys Ala Phe Val Phe Asp Lys Ala Arg Lys Arg Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asp Cys
        115                 120                 125

Ile Ile Gly Asn Gly Arg Ser Tyr Arg Gly Thr Val Ser Ile Thr Lys
    130                 135                 140

Ser Gly Ile Lys Cys Gln Pro Trp Ser Ala Met Ile Pro His Glu His
145                 150                 155                 160

Ser Phe Leu Pro Ser Ser Tyr Arg Gly Glu Asp Leu Arg Glu Asn Tyr
                165                 170                 175

Cys Arg Asn Pro Arg Gly Glu Glu Gly Gly Pro Trp Cys Tyr Thr Ser
            180                 185                 190

Asp Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270
```

```
Thr Leu Asp Pro His Thr Arg Trp Glu Tyr Cys Ala Ile Lys Thr Cys
        275                 280                 285

Ala Asp Asn Thr Met Asn Asp Thr Asp Val Pro Leu Glu Thr Thr Glu
    290                 295                 300

Cys Ile Gln Gly Gln Gly Glu Gly Tyr Arg Gly Thr Val Asn Thr Ile
305                 310                 315                 320

Trp Asn Gly Ile Pro Cys Gln Arg Trp Asp Ser Gln Tyr Pro His Glu
                325                 330                 335

His Asp Met Thr Pro Glu Asn Phe Lys Cys Lys Asp Leu Arg Glu Asn
            340                 345                 350

Tyr Cys Arg Asn Pro Asp Gly Ser Glu Ser Pro Trp Cys Phe Thr Thr
        355                 360                 365

Asp Pro Asn Ile Arg Val Gly Tyr Cys Ser Gln Ile Pro Asn Cys Asp
    370                 375                 380

Met Ser His Gly Gln Asp Cys Tyr Arg Gly Asn Gly Lys Asn Tyr Met
385                 390                 395                 400

Gly Asn Leu Ser Gln Thr Arg Ser Gly Leu Thr Cys Ser Met Trp Asp
                405                 410                 415

Lys Asn Met Glu Asp Leu His Arg His Ile Phe Trp Glu Pro Asp Ala
            420                 425                 430

Ser Lys Leu Asn Glu Asn Tyr Cys Arg Asn Pro Asp Asp Asp Ala His
        435                 440                 445

Gly Pro Trp Cys Tyr Thr Gly Asn Pro Leu Ile Pro Trp Asp Tyr Cys
    450                 455                 460

Pro Ile Ser Arg Cys Glu Gly Asp Thr Thr Pro Thr Ile Val Asn Leu
465                 470                 475                 480

Asp His Pro Val Ile Ser Cys Ala Lys Thr Lys Gln Leu Arg Val Val
                485                 490                 495

Asn Gly Ile Pro Thr Arg Thr Asn Ile Gly Trp Met Val Ser Leu Arg
            500                 505                 510

Tyr Arg Asn Lys His Ile Cys Gly Gly Ser Leu Ile Lys Glu Ser Trp
        515                 520                 525

Val Leu Thr Ala Arg Gln Cys Phe Pro Ser Arg Asp Leu Lys Asp Tyr
    530                 535                 540

Glu Ala Trp Leu Gly Ile His Asp Val His Gly Arg Gly Asp Glu Lys
545                 550                 555                 560

Cys Lys Gln Val Leu Asn Val Ser Gln Leu Val Tyr Gly Pro Glu Gly
                565                 570                 575

Ser Asp Leu Val Leu Met Lys Leu Ala Arg Pro Ala Val Leu Asp Asp
            580                 585                 590

Phe Val Ser Thr Ile Asp Leu Pro Asn Tyr Gly Cys Thr Ile Pro Glu
        595                 600                 605

Lys Thr Ser Cys Ser Val Tyr Gly Trp Gly Tyr Thr Gly Leu Ile Asn
    610                 615                 620

Tyr Asp Gly Leu Leu Arg Val Ala His Leu Tyr Ile Met Gly Asn Glu
625                 630                 635                 640

Lys Cys Ser Gln His His Arg Gly Lys Val Thr Leu Asn Glu Ser Glu
                645                 650                 655

Ile Cys Ala Gly Ala Glu Lys Ile Gly Ser Gly Pro Cys Glu Gly Asp
            660                 665                 670

Tyr Gly Gly Pro Leu Val Cys Glu Gln His Lys Met Arg Met Val Leu
        675                 680                 685
```

Gly Val Ile Val Pro Gly Arg Gly Cys Ala Ile Pro Asn Arg Pro Gly
    690                 695                 700

Ile Phe Val Arg Val Ala Tyr Tyr Ala Lys Trp Ile His Lys Ile Ile
705                 710                 715                 720

Leu Thr Tyr Lys Val Pro Gln Ser
                725

<210> SEQ ID NO 28
<211> LENGTH: 140
<212> TYPE: PRT
<213> ORGANISM: Homo sapiens

<400> SEQUENCE: 28

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140

<210> SEQ ID NO 29
<211> LENGTH: 140
<212> TYPE: PRT
<213> ORGANISM: Artificial Sequence
<220> FEATURE:
<223> OTHER INFORMATION: FGF1 Variant

<400> SEQUENCE: 29

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asn Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Arg Phe Leu Pro Leu Pro Val Ser Ser Asp 130 135 140

<210> SEQ ID NO 30
<211> LENGTH: 140
<212> TYPE: PRT
<213> ORGANISM: Artificial Sequence
<220> FEATURE:
<223> OTHER INFORMATION: FGF1 Variant

<400> SEQUENCE: 30

```
Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Pro His Ile Gln Leu Gln Leu Ile Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn Gly Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Leu Phe Leu Pro Leu Pro Val Ser Ser Asp
    130                 135                 140
```

<210> SEQ ID NO 31
<211> LENGTH: 140
<212> TYPE: PRT
<213> ORGANISM: Artificial Sequence
<220> FEATURE:
<223> OTHER INFORMATION: FGF1 Variant

<400> SEQUENCE: 31

```
Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asn Gly Thr Val Asp
            20                  25                  30

Gly Thr Arg Asp Arg Ser Asp Pro His Ile Gln Leu Gln Leu Ile Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn Gly Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Arg Phe Leu Pro Leu Pro Val Ser Ser Asp
    130                 135                 140
```

<210> SEQ ID NO 32
<211> LENGTH: 140

```
<212> TYPE: PRT
<213> ORGANISM: Artificial Sequence
<220> FEATURE:
<223> OTHER INFORMATION: FGF1 Variant

<400> SEQUENCE: 32

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Arg Phe Leu Pro Leu Pro Val Ser Ser Asp
    130                 135                 140


<210> SEQ ID NO 33
<211> LENGTH: 140
<212> TYPE: PRT
<213> ORGANISM: Artificial Sequence
<220> FEATURE:
<223> OTHER INFORMATION: FGF1 Variant

<400> SEQUENCE: 33

Phe Asn Leu Pro Pro Gly Asn Tyr Lys Lys Pro Lys Leu Leu Tyr Cys
1               5                   10                  15

Ser Asn Gly Gly His Phe Leu Arg Ile Leu Pro Asp Gly Thr Val Asp
            20                  25                  30

Gly Thr Arg Asp Arg Ser Asp Gln His Ile Gln Leu Gln Leu Ser Ala
        35                  40                  45

Glu Ser Val Gly Glu Val Tyr Ile Lys Ser Thr Glu Thr Gly Gln Tyr
    50                  55                  60

Leu Ala Met Asp Thr Asp Gly Leu Leu Tyr Gly Ser Gln Thr Pro Asn
65                  70                  75                  80

Glu Glu Cys Leu Phe Leu Glu Arg Leu Glu Glu Asn His Tyr Asn Thr
                85                  90                  95

Tyr Ile Ser Lys Lys His Ala Glu Lys Asn Trp Phe Val Gly Leu Lys
            100                 105                 110

Lys Asn Gly Ser Cys Lys Arg Gly Pro Arg Thr His Tyr Gly Gln Lys
        115                 120                 125

Ala Ile Lys Phe Leu Pro Leu Pro Val Ser Ser Asp
    130                 135                 140


<210> SEQ ID NO 34
<211> LENGTH: 31
<212> TYPE: PRT
<213> ORGANISM: Homo sapiens

<400> SEQUENCE: 34
```

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly
            20                  25                  30

<210> SEQ ID NO 35
<211> LENGTH: 692
<212> TYPE: PRT
<213> ORGANISM: Homo sapiens

<400> SEQUENCE: 35

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Tyr Arg Gly Lys Asp Leu Gln Glu Asn Tyr Cys Arg Asn Pro
    130                 135                 140

Arg Gly Glu Glu Gly Gly Pro Trp Cys Phe Thr Ser Asn Pro Glu Val
145                 150                 155                 160

Arg Tyr Glu Val Cys Asp Ile Pro Gln Cys Ser Glu Val Glu Cys Met
                165                 170                 175

Thr Cys Asn Gly Glu Ser Tyr Arg Gly Leu Met Asp His Thr Glu Ser
            180                 185                 190

Gly Lys Ile Cys Gln Arg Trp Asp His Gln Thr Pro His Arg His Lys
        195                 200                 205

Phe Leu Pro Glu Arg Tyr Pro Asp Lys Gly Phe Asp Asp Asn Tyr Cys
    210                 215                 220

Arg Asn Pro Asp Gly Gln Pro Arg Pro Trp Cys Tyr Thr Leu Asp Pro
225                 230                 235                 240

His Thr Arg Trp Glu Tyr Cys Ala Ile Lys Thr Cys Ala Asp Asn Thr
                245                 250                 255

Met Asn Asp Thr Asp Val Pro Leu Glu Thr Thr Glu Cys Ile Gln Gly
            260                 265                 270

Gln Gly Glu Gly Tyr Arg Gly Thr Val Asn Thr Ile Trp Asn Gly Ile
        275                 280                 285

Pro Cys Gln Arg Trp Asp Ser Gln Tyr Pro His Glu His Asp Met Thr
    290                 295                 300

Pro Glu Asn Phe Lys Cys Lys Asp Leu Arg Glu Asn Tyr Cys Arg Asn
305                 310                 315                 320

Pro Asp Gly Ser Glu Ser Pro Trp Cys Phe Thr Thr Asp Pro Asn Ile
                325                 330                 335

Arg Val Gly Tyr Cys Ser Gln Ile Pro Asn Cys Asp Met Ser His Gly
            340                 345                 350

```
Gln Asp Cys Tyr Arg Gly Asn Gly Lys Asn Tyr Met Gly Asn Leu Ser
        355                 360                 365

Gln Thr Arg Ser Gly Leu Thr Cys Ser Met Trp Asp Lys Asn Met Glu
    370                 375                 380

Asp Leu His Arg His Ile Phe Trp Glu Pro Asp Ala Ser Lys Leu Asn
385                 390                 395                 400

Glu Asn Tyr Cys Arg Asn Pro Asp Asp Asp Ala His Gly Pro Trp Cys
                405                 410                 415

Tyr Thr Gly Asn Pro Leu Ile Pro Trp Asp Tyr Cys Pro Ile Ser Arg
            420                 425                 430

Cys Glu Gly Asp Thr Thr Pro Thr Ile Val Asn Leu Asp His Pro Val
        435                 440                 445

Ile Ser Cys Ala Lys Thr Lys Gln Leu Arg Val Val Asn Gly Ile Pro
    450                 455                 460

Thr Arg Thr Asn Ile Gly Trp Met Val Ser Leu Arg Tyr Arg Asn Lys
465                 470                 475                 480

His Ile Cys Gly Gly Ser Leu Ile Lys Glu Ser Trp Val Leu Thr Ala
                485                 490                 495

Arg Gln Cys Phe Pro Ser Arg Asp Leu Lys Asp Tyr Glu Ala Trp Leu
            500                 505                 510

Gly Ile His Asp Val His Gly Arg Gly Asp Glu Lys Cys Lys Gln Val
        515                 520                 525

Leu Asn Val Ser Gln Leu Val Tyr Gly Pro Glu Gly Ser Asp Leu Val
    530                 535                 540

Leu Met Lys Leu Ala Arg Pro Ala Val Leu Asp Asp Phe Val Ser Thr
545                 550                 555                 560

Ile Asp Leu Pro Asn Tyr Gly Cys Thr Ile Pro Glu Lys Thr Ser Cys
                565                 570                 575

Ser Val Tyr Gly Trp Gly Tyr Thr Gly Leu Ile Asn Tyr Asp Gly Leu
            580                 585                 590

Leu Arg Val Ala His Leu Tyr Ile Met Gly Asn Glu Lys Cys Ser Gln
        595                 600                 605

His His Arg Gly Lys Val Thr Leu Asn Glu Ser Glu Ile Cys Ala Gly
    610                 615                 620

Ala Glu Lys Ile Gly Ser Gly Pro Cys Glu Gly Asp Tyr Gly Gly Pro
625                 630                 635                 640

Leu Val Cys Glu Gln His Lys Met Arg Met Val Leu Gly Val Ile Val
                645                 650                 655

Pro Gly Arg Gly Cys Ala Ile Pro Asn Arg Pro Gly Ile Phe Val Arg
            660                 665                 670

Val Ala Tyr Tyr Ala Lys Trp Ile His Lys Ile Ile Leu Thr Tyr Lys
        675                 680                 685

Val Pro Gln Ser
    690


<210> SEQ ID NO 36
<211> LENGTH: 458
<212> TYPE: PRT
<213> ORGANISM: Homo sapiens

<400> SEQUENCE: 36

Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
```

-continued

```
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Tyr Arg Gly Lys Asp Leu Gln Glu Asn Tyr Cys Arg Asn Pro
    130                 135                 140

Arg Gly Glu Glu Gly Gly Pro Trp Cys Phe Thr Ser Asn Pro Glu Val
145                 150                 155                 160

Arg Tyr Glu Val Cys Asp Ile Pro Gln Cys Ser Glu Val Glu Cys Met
                165                 170                 175

Thr Cys Asn Gly Glu Ser Tyr Arg Gly Leu Met Asp His Thr Glu Ser
            180                 185                 190

Gly Lys Ile Cys Gln Arg Trp Asp His Gln Thr Pro His Arg His Lys
        195                 200                 205

Phe Leu Pro Glu Arg Tyr Pro Asp Lys Gly Phe Asp Asp Asn Tyr Cys
    210                 215                 220

Arg Asn Pro Asp Gly Gln Pro Arg Pro Trp Cys Tyr Thr Leu Asp Pro
225                 230                 235                 240

His Thr Arg Trp Glu Tyr Cys Ala Ile Lys Thr Cys Ala Asp Asn Thr
                245                 250                 255

Met Asn Asp Thr Asp Val Pro Leu Glu Thr Thr Glu Cys Ile Gln Gly
            260                 265                 270

Gln Gly Glu Gly Tyr Arg Gly Thr Val Asn Thr Ile Trp Asn Gly Ile
        275                 280                 285

Pro Cys Gln Arg Trp Asp Ser Gln Tyr Pro His Glu His Asp Met Thr
    290                 295                 300

Pro Glu Asn Phe Lys Cys Lys Asp Leu Arg Glu Asn Tyr Cys Arg Asn
305                 310                 315                 320

Pro Asp Gly Ser Glu Ser Pro Trp Cys Phe Thr Thr Asp Pro Asn Ile
                325                 330                 335

Arg Val Gly Tyr Cys Ser Gln Ile Pro Asn Cys Asp Met Ser His Gly
            340                 345                 350

Gln Asp Cys Tyr Arg Gly Asn Gly Lys Asn Tyr Met Gly Asn Leu Ser
        355                 360                 365

Gln Thr Arg Ser Gly Leu Thr Cys Ser Met Trp Asp Lys Asn Met Glu
    370                 375                 380

Asp Leu His Arg His Ile Phe Trp Glu Pro Asp Ala Ser Lys Leu Asn
385                 390                 395                 400

Glu Asn Tyr Cys Arg Asn Pro Asp Asp Asp Ala His Gly Pro Trp Cys
                405                 410                 415

Tyr Thr Gly Asn Pro Leu Ile Pro Trp Asp Tyr Cys Pro Ile Ser Arg
            420                 425                 430

Cys Glu Gly Asp Thr Thr Pro Thr Ile Val Asn Leu Asp His Pro Val
        435                 440                 445
```

```
Ile Ser Cys Ala Lys Thr Lys Gln Leu Arg
    450                 455


<210> SEQ ID NO 37
<211> LENGTH: 234
<212> TYPE: PRT
<213> ORGANISM: Homo sapiens

<400> SEQUENCE: 37

Val Val Asn Gly Ile Pro Thr Arg Thr Asn Ile Gly Trp Met Val Ser
1               5                   10                  15

Leu Arg Tyr Arg Asn Lys His Ile Cys Gly Gly Ser Leu Ile Lys Glu
            20                  25                  30

Ser Trp Val Leu Thr Ala Arg Gln Cys Phe Pro Ser Arg Asp Leu Lys
        35                  40                  45

Asp Tyr Glu Ala Trp Leu Gly Ile His Asp Val His Gly Arg Gly Asp
    50                  55                  60

Glu Lys Cys Lys Gln Val Leu Asn Val Ser Gln Leu Val Tyr Gly Pro
65                  70                  75                  80

Glu Gly Ser Asp Leu Val Leu Met Lys Leu Ala Arg Pro Ala Val Leu
                85                  90                  95

Asp Asp Phe Val Ser Thr Ile Asp Leu Pro Asn Tyr Gly Cys Thr Ile
            100                 105                 110

Pro Glu Lys Thr Ser Cys Ser Val Tyr Gly Trp Gly Tyr Thr Gly Leu
        115                 120                 125

Ile Asn Tyr Asp Gly Leu Leu Arg Val Ala His Leu Tyr Ile Met Gly
    130                 135                 140

Asn Glu Lys Cys Ser Gln His His Arg Gly Lys Val Thr Leu Asn Glu
145                 150                 155                 160

Ser Glu Ile Cys Ala Gly Ala Glu Lys Ile Gly Ser Gly Pro Cys Glu
                165                 170                 175

Gly Asp Tyr Gly Gly Pro Leu Val Cys Glu Gln His Lys Met Arg Met
            180                 185                 190

Val Leu Gly Val Ile Val Pro Gly Arg Gly Cys Ala Ile Pro Asn Arg
        195                 200                 205

Pro Gly Ile Phe Val Arg Val Ala Tyr Tyr Ala Lys Trp Ile His Lys
    210                 215                 220

Ile Ile Leu Thr Tyr Lys Val Pro Gln Ser
225                 230


<210> SEQ ID NO 38
<211> LENGTH: 5
<212> TYPE: PRT
<213> ORGANISM: Homo sapiens

<400> SEQUENCE: 38

Ser Phe Leu Pro Ser
1               5
```